US012721942B2

(12) United States Patent
Rosen et al.

(10) Patent No.: US 12,721,942 B2
(45) Date of Patent: Sep. 1, 2026

(54) SURGICAL DRAINS AND SYSTEMS AND METHODS FOR USING SAME

(71) Applicant: Raydiant Oximetry, Inc., San Ramon, CA (US)

(72) Inventors: Mark Andrew Rosen, Piedmont, CA (US); Russell DeLonzor, San Ramon, CA (US); Neil Padharia Ray, Sacramento, CA (US); Jeffrey Hernandez, Livermore, CA (US)

(73) Assignee: Raydiant Oximetry, Inc., San Ramon, CA (US)

( * ) Notice: Subject to any disclaimer, the term of this patent is extended or adjusted under 35 U.S.C. 154(b) by 0 days.

(21) Appl. No.: 18/756,713

(22) Filed: Jun. 27, 2024

(65) Prior Publication Data

US 2024/0342359 A1 Oct. 17, 2024

Related U.S. Application Data

(63) Continuation of application No. PCT/US2024/010578, filed on Jan. 5, 2024.

(Continued)

(51) Int. Cl.

| | |
|---|---|
| ***A61M 1/00*** | (2006.01) |
| ***A61M 25/00*** | (2006.01) |
| ***A61M 25/01*** | (2006.01) |

(52) U.S. Cl.

CPC ................ *A61M 1/90* (2021.05); *A61M 1/87* (2021.05); *A61M 25/007* (2013.01);

(Continued)

(58) Field of Classification Search

CPC ............ A61B 17/42; A61B 2017/4216; A61B 2017/12004; A61B 2017/306;

(Continued)

(56) References Cited

U.S. PATENT DOCUMENTS

| | | | | |
|---|---|---|---|---|
| 3,312,222 A * | 4/1967 | Dwyer | A61M 29/00 606/198 |
| 3,640,281 A * | 2/1972 | Robertson | A61M 25/06 604/500 |

(Continued)

FOREIGN PATENT DOCUMENTS

GB 2607028 11/2022

OTHER PUBLICATIONS

Raydiant Oximetry, Inc.; International Application No. PCT/US2024/010578 filed Jan. 5, 2024; International Search Report and Written Opinion; ISA/US; Jul. 16, 2024; 14 pp.

(Continued)

*Primary Examiner* — Adam Marcetich

(74) *Attorney, Agent, or Firm* — Resonance IP Law, PC

(57) ABSTRACT

Surgical drains may include a tube, a drainage component, and an positioning mechanism positioned between them. The positioning mechanism may include a shaft configured to encircle a junction between the tube and the drainage component and a plurality of extensions that extend from the shaft. The drainage component may have a plurality of holes sized and configured to allow fluid, solids, and/or gas to pass therethrough, enter a lumen of the drainage component, and be communicated to a lumen of the tube for evacuation from a hollow organ and/or tissue in which the surgical drain is placed. On some occasions, the surgical drain may be placed within a uterine cavity via a hysterotomy following pelvic surgery and may be used to evacuate blood and other fluids from the uterine cavity and/or contract the uterus following caesarian delivery of a fetus.

8 Claims, 48 Drawing Sheets

Related U.S. Application Data

(60) Provisional application No. 63/456,419, filed on Mar. 31, 2023, provisional application No. 63/437,590, filed on Jan. 6, 2023.

(52) U.S. Cl.
CPC .......... *A61M 25/0102* (2013.01); *A61M 1/71* (2021.05); *A61M 2205/13* (2013.01); *A61M 2205/3379* (2013.01); *A61M 2205/582* (2013.01); *A61M 2205/584* (2013.01); *A61M 2210/1433* (2013.01)

(58) Field of Classification Search
CPC .......... A61B 2217/005; A61B 17/4241; A61B 2017/00561; A61M 2210/1433; A61M 1/916; A61M 1/71; A61M 1/84; A61M 1/90
See application file for complete search history.

(56) References Cited

U.S. PATENT DOCUMENTS

| | | | | |
|---|---|---|---|---|
| 3,920,023 | A * | 11/1975 | Dye | A61M 25/06 604/506 |
| 4,684,369 | A * | 8/1987 | Wildemeersch | A61M 27/00 604/272 |
| 5,112,310 | A * | 5/1992 | Grobe | A61J 15/0038 604/105 |
| 5,209,754 | A * | 5/1993 | Ahluwalia | A61B 17/4241 606/1 |
| 6,039,714 | A * | 3/2000 | Cracauer | A61J 15/0038 604/174 |
| 8,715,244 | B2 | 5/2014 | Prechtel et al. | |
| 9,125,686 | B2 | 9/2015 | Norred et al. | |
| 10,064,651 | B2 | 9/2018 | Norred et al. | |
| 10,729,464 | B1 * | 8/2020 | Booher, Sr. | A61F 6/08 |
| 11,103,377 | B1 | 8/2021 | Weston | |
| 11,241,254 | B2 | 2/2022 | Norred et al. | |
| 11,291,473 | B2 | 4/2022 | Norred et al. | |
| 11,849,971 | B1 * | 12/2023 | Hemmanur | A61M 1/87 |
| 2001/0025155 | A1 * | 9/2001 | Yoon | A61M 25/1011 604/1 |
| 2005/0288722 | A1 * | 12/2005 | Eigler | A61N 1/3629 607/9 |
| 2008/0045924 | A1 * | 2/2008 | Cox | A61B 17/42 604/515 |
| 2008/0125692 | A1 * | 5/2008 | Feemster | A61F 6/08 604/15 |
| 2008/0243116 | A1 * | 10/2008 | Anderson | A61N 1/06 606/41 |
| 2009/0043284 | A1 * | 2/2009 | Ogle | A61N 1/06 604/523 |
| 2009/0143713 | A1 * | 6/2009 | Van Dam | A61B 17/11 604/9 |
| 2009/0149716 | A1 | 6/2009 | Diao et al. | |
| 2010/0106152 | A1 * | 4/2010 | Truckai | A61B 18/14 606/33 |
| 2011/0259344 | A1 * | 10/2011 | Ahluwalia | A61B 17/4241 128/834 |
| 2011/0313359 | A1 * | 12/2011 | Cohen | A61J 15/0057 604/175 |
| 2013/0211385 | A1 | 8/2013 | Lazarus | |
| 2013/0245637 | A1 | 9/2013 | Norred et al. | |
| 2014/0121583 | A1 | 5/2014 | Duncan et al. | |
| 2014/0257322 | A1 * | 9/2014 | Batchelor | A61B 17/4241 606/119 |
| 2015/0127016 | A1 * | 5/2015 | Sauer | A61B 17/4241 606/119 |
| 2015/0265456 | A1 * | 9/2015 | Booher, Sr. | A61F 6/08 128/836 |
| 2016/0143816 | A1 * | 5/2016 | Benuri-Silbiger | A61J 15/003 604/175 |
| 2017/0035949 | A1 * | 2/2017 | Loske | A61M 1/75 |
| 2017/0281231 | A1 * | 10/2017 | Langell | A61B 17/4241 |
| 2018/0055523 | A1 * | 3/2018 | Bair | A61M 1/84 |
| 2018/0360494 | A1 * | 12/2018 | Melsheimer | A61B 17/1204 |
| 2019/0038315 | A1 * | 2/2019 | Prior | A61B 17/42 |
| 2019/0059947 | A1 | 2/2019 | Bunch et al. | |
| 2019/0216504 | A1 | 7/2019 | Norred et al. | |
| 2020/0093498 | A1 * | 3/2020 | Roberts | A61B 17/12099 |
| 2020/0352602 | A1 | 11/2020 | Norred et al. | |
| 2020/0397667 | A1 * | 12/2020 | Zamnegar | A61J 15/0026 |
| 2021/0137725 | A1 * | 5/2021 | Shaviv | A61F 5/4553 |
| 2021/0260346 | A1 | 8/2021 | Moon | |
| 2022/0022916 | A1 | 1/2022 | Uchida | |
| 2022/0175420 | A1 | 6/2022 | Norred et al. | |
| 2022/0240982 | A1 * | 8/2022 | Norred | A61B 17/1204 |
| 2023/0131497 | A1 | 4/2023 | Huelsen | |
| 2023/0277822 | A1 * | 9/2023 | Morehead | A61M 31/00 604/28 |
| 2023/0320753 | A1 * | 10/2023 | Cobb | A61B 17/42 |
| 2023/0414254 | A1 * | 12/2023 | Radl | A61M 1/87 |
| 2025/0009390 | A1 * | 1/2025 | Cobb | A61M 25/04 |

OTHER PUBLICATIONS

Hofmeyr, GJ et al.; Novel suction tube uterine tamponade for treating intractable postpartum haemorrhage: description of technique and report of three cases; BJOG 2020; 127:1280-1283.

Panicker, T. N. Vasudeva; Panicker's Vacuum Suction Haemostatic Device for Treating Post-Partum Haemorrhage; The Journal of Obstetrics and Gynecology of India (Mar.-Apr. 2017) 67(2):150-151; DOI 10.1007/s13224-017-0963-x.

Cebekhulu, Sylvia N. et al.; Suction Tube Uterine Tamponade for treatment of refractory postpartum hemorrhage: Internal feasibility and acceptability pilot of a randomized clinical trial; International Federation of Gynecology and Obstetrics; 2021;00:1-7.

Hofmeyr, G. Justus et al.; Randomized feasibility study of suction-tube uterine tamponade for postpartum hemorrhage; Int J Gynecol Obstet 2019; 146: 339-343.

Ram, Hemmanur Samrtha; Comment on "Panicker's Vacuum Suction Hemostatic Device for Treating Postpartum Hemorrhage"; The Journal of Obstetrics and Gynecology of India (Nov.-Dec. 2017) 67(6):454-455 DOI 10.1007/s13224-017-1026-z.

Haslinger, Christian et al.; Vacuum-Induced Tamponade for Treatment of Postpartum Hemorrhage; (Obstet Gynecol 2021;138:361-5) Doi: 10.1097/AOG.0000000000004510; vol. 138, No. 3, Sep. 2021.

Makhija, Bela et al.; Suction and Evacuation for Management of Postpartum Hemorrhage; International Journal of Women's Health and Reproduction Sciences; vol. 2, No. 5, Autumn 2014, 278-280.

Purwosunu, Yuditiya et al.; Control of Postpartum Hemorrhage Using Vacuum-Induced Uterine Tamponade; (Obstet Gynecol 2016;128:33-6) DOI: 10.1097/AOG.0000000000001473; vol. 128, No. 1, Jul. 2016.

Abraham C. Bakri balloon placement in the successful management of postpartum hemorrhage in a bicornuate uterus: A case report. Int J Surg Case Rep. 2017;31:218-220. doi: 10.1016/j.ijscr.2017.01.055. Epub Jan. 24, 2017. PMID: 28189983; PMCID: PMC5302184.

ACOG Committee on Practice Bulletins-Obstetrics. Practice Bulletin No. 183: Postpartum Hemorrhage. Obstet Gynecol. Oct. 2017; 130(4):e168-e186. doi: 10.1097/AOG.0000000000002351. PMID: 28937571.

ACOG Committee Opinion, No. 794. Quantitative Blood Loss in Obstetric Hemorrhage. Obstet Gynecol. Dec. 2019; 134(6):e150-e156. doi: 10.1097/AOG.0000000000003564. PMID: 31764759.

Atallah F, Goffman D. Improving Healthcare Responses to Obstetric Hemorrhage: Strategies to Mitigate Risk. Risk Manag Healthc Policy. Jan. 21, 2020; 13:35-42. doi: 10.2147/RMHP.S179632. PMID: 32021518; PMCID: PMC6982439.

Balki M, Wong CA. Refractory uterine atony: still a problem after all these years. Int J Obstet Anesth. Nov. 2021;48:103207. doi: 10.1016/j.ijoa.2021.103207. Epub Jul. 21, 2021. PMID: 34391025.

Bateman BT, Huybrechts KF, Hernandez-Diaz S, Liu J, Ecker JL, Avorn J. Methylergonovine maleate and the risk of myocardial ischemia and infarction. Am J Obstet Gynecol. Nov. 2013;209(5):459.e1-459.e13. doi: 10.1016/j.ajog.2013.07.001. Epub Jul. 11, 2013. PMID: 23850529; PMCID: PMC4103983.

(56) References Cited

OTHER PUBLICATIONS

Blaha J, Bartošová T. Epidemiology and definition of PPH worldwide. Best Pract Res Clin Anaesthesiol. Dec. 2022;36(3-4):325-339. doi: 10.1016/j.bpa.2022.11.001. Epub Nov. 13, 2022. PMID: 36513428.

Bryant A, Mhyre JM, Leffert LR, Hoban RA, Yakoob MY, Bateman BT. The association of maternal race and ethnicity and the risk of postpartum hemorrhage. Anesth Analg. Nov. 2012; 115(5):1127-36. doi: 10.1213/ANE.0b013e3182691e62. Epub Aug. 10, 2012. PMID: 22886840.

Butwick A, Lyell D, Goodnough L. How do I manage severe postpartum hemorrhage? Transfusion. May 2020;60(5):897-907. doi: 10.1111/trf.15794. Epub Apr. 22, 2020. PMID: 32319687.

Callaghan WM, Kuklina EV, Berg CJ. Trends in postpartum hemorrhage: United States, 1994-2006. Am J Obstet Gynecol. Apr. 2010;202(4):353.e1-6. doi: 10.1016/j.ajog.2010.01.011. PMID: 20350642.

Case 3:25-cv-00392; Plaintiff Raydiant Oximetry, Inc.'s Certification of Conflicts and Interested Entities or Persons filed Jan. 1, 2025.

Case 3:25-cv-00392; Plaintiff Raydiant Oximetry, Inc.'s Civil Cover Sheet filed Jan. 1, 2025.

Case 3:25-cv-00392; Plaintiff Raydiant Oximetry, Inc.'s Report on the Filing or Determination of an Action Regarding a Patent or Trademark filed Jan. 1, 2025.

Case 3:25-cv-00392; Plaintiff Raydiant Oximetry, Inc.'s Summons in a Civil Action filed Jan. 1, 2025.

Cebekhulu SN, Abdul H, Batting J, Chauke L, Dlakavu F, Fawcus S, Govender L, Majeke B, Mbongozi X, Singata-Madliki M, Middleton K, Mlandu P, Naidoo P, Ndaba S, Soma-Pillay P, Spence T, Ntambua SC, Hofmeyr J. "Suction Tube Uterine Tamponade" for treatment of refractory postpartum hemorrhage: Internal feasibility and acceptability pilot of a randomized clinical trial. Int J Gynaecol Obstet. Oct. 4, 2021. doi: 10.1002/ijgo.13963. Epub ahead of print. PMID: 34605016.

D'Alton ME, Rood KM, Smid MC, Simhan HN, Skupski DW, Subramaniam A, Gibson KS, Rosen T, Clark SM, Dudley D, Iqbal SN, Paglia MJ, Duzyj CM, Chien EK, Gibbins KJ, Wine KD, Bentum NAA, Kominiarek MA, Tuuli MG, Goffman D. Intrauterine Vacuum-Induced Hemorrhage-Control Device for Rapid Treatment of Postpartum Hemorrhage. Obstet Gynecol. Nov. 2020; 136(5):882-891. doi: 10.1097/AOG.0000000000004138. PMID: 32909970; PMCID: PMC7575019.

Davey MA, Flood M, Pollock W, Cullinane F, McDonald S. Risk factors for severe postpartum haemorrhage: A population-based retrospective cohort study. Aust N Z J Obstet Gynaecol. Aug. 2020;60(4):522-532. doi: 10.1111/ajo.13099. Epub Nov. 22, 2019. PMID: 31758550.

Evensen A, Anderson JM, Fontaine P. Postpartum Hemorrhage: Prevention and Treatment. Am Fam Physician. Apr. 1, 2017;95(7):442-449. PMID: 28409600.

Feduniw S, Warzecha D, Szymusik I, Wielgos M. Epidemiology, prevention and management of early postpartum hemorrhage—a systematic review. Ginekol Pol. 2020;91(1):38-44. doi: 10.5603/GP.2020.0009. PMID: 32039467.

Fonseca A, Ayres de Campos D. Maternal morbidity and mortality due to placenta accreta spectrum disorders. Best Pract Res Clin Obstet Gynaecol. Apr. 2021;72:84-91. doi: 10.1016/j.bpobgyn.2020.07.011. Epub Jul. 20, 2020. PMID: 32778495.

Gyamfi-Bannerman C, Srinivas SK, Wright JD, Goffman D, Siddiq Z, D'Alton ME, Friedman AM. Postpartum hemorrhage outcomes and race. Am J Obstet Gynecol. Aug. 2018;219(2):185.e1-185.e10. doi: 10.1016/j.ajog.2018.04.052. Epub May 9, 2018. PMID: 29752934.

Haslinger C, Weber K, Zimmermann R. Vacuum-Induced Tamponade for Treatment of Postpartum Hemorrhage. Obstet Gynecol. Sep. 1, 2021;138(3):361-365. doi: 10.1097/AOG.0000000000004510. PMID: 34352848; PMCID: PMC8366764.

Hawkins JL. Obstetric Hemorrhage. Anesthesiol Clin. Dec. 2020;38(4):839-858. doi: 10.1016/j.anclin.2020.08.010. Epub Oct. 15, 2020. PMID: 33127031.

Hofmeyr GJ, Middleton K, Singata-Madliki M. Randomized feasibility study of suction-tube uterine tamponade for postpartum hemorrhage. Int J Gynaecol Obstet. Sep. 2019; 146(3):339-343. doi: 10.1002/ijgo.12889. Epub Jul. 8, 2019. PMID: 31206652.

Hofmeyr GJ, Singata-Madliki M. Novel suction tube uterine tamponade for treating intractable postpartum haemorrhage: description of technique and report of three cases. BJOG. Sep. 2020; 127(10):1280-1283. doi: 10.1111/1471-0528.16169. Epub Mar. 9, 2020. PMID: 32043686.

Kerschen GW, Hoyt K, Johnson E, Patel S. Eclampsia with RCVS: Postpartum seizure provoked by methergine. Pregnancy Hypertens. Mar. 2022;27:131-133. doi: 10.1016/j.preghy.2022.01.002. Epub Jan. 15, 2022. PMID: 35063759; PMCID: PMC8858862.

Kershaw CM, Khalid M, McGowan MR, Ingram K, Leethongdee S, Wax G, Scaramuzzi RJ. The anatomy of the sheep cervix and its influence on the transcervical passage of an inseminating pipette into the uterine lumen. Theriogenology. Sep. 15, 2005;64(5):1225-35. doi: 10.1016/j.theriogenology.2005.02.017. PMID: 15904956.

Knoll W, Phelan R, Hopman WM, Ho AM, Cenkowski M, Mizubuti GB, Ghasemlou N, Klar G. Retrospective Review of Time to Uterotonic Administration and Maternal Outcomes After Postpartum Hemorrhage. J Obstet Gynaecol Can. May 2022; 44(5):490-495. doi: 10.1016/j.jogc.2021.11.011. Epub Nov. 26, 2021. PMID: 34844004.

Kuklina EV, Meikle SF, Jamieson DJ, Whiteman MK, Barfield WD, Hillis SD, Posner SF. Severe obstetric morbidity in the United States: 1998-2005. Obstet Gynecol. Feb. 2009; 113(2 Pt 1):293-9. doi: 10.1097/AOG.0b013e3181954e5b. PMID: 19155897; PMCID: PMC2743391.

Langesaeter E, Rosseland LA, Stubhaug A. Hemodynamic effects of oxytocin during cesarean delivery. Int J Gynaecol Obstet. 2006;95:46-47. https://doi.org/10.1016/j.ijgo.2006.05.032.

Liabsuetrakul T, Peeyananjarassri K. Mechanical dilatation of the cervix during elective caeserean section before the onset of labour for reducing postoperative morbidity. Cochrane Database Syst Rev. Aug. 10, 2018;8(8):CD008019. doi: 10.1002/14651858.CD008019.pub3. PMID: 30096215; PMCID: PMC6513223.

Makhija B, Haritwal A, Arora M, Agrawal D. Suction and Evacuation for Management of Postpartum Hemorrhage. International Journal of Women's Health and Reproduction Sciences. vol. 2, No. 5, 2014, 278-280. DOI: 10.15296/ijwhr.2014.44.

Panicker TN. Panicker's Vacuum Suction Haemostatic Device for Treating Post-Partum Haemorrhage. J Obstet Gynaecol India. Apr. 2017;67(2):150-151. doi: 10.1007/s13224-017-0963-x. Epub Mar. 1, 2017. PMID: 28405125; PMCID: PMC5371527.

Pavord S, Maybury H. How I treat postpartum hemorrhage. Blood. Apr. 30, 2015;125(18):2759-70. doi: 10.1182/blood-2014-10-512608. Epub Mar. 13, 2015. PMID: 25769619.

Pillarisetty LS, Thai T, Mannem M, Bandaru SK. Postpartum Hemorrhage: Use of Bakri Balloon During Cesarean Delivery, a Case Report and Review. J Clin Gynecol Obstet 2019:8(2):57-61.

Purwosunu Y, Sarkoen W, Arulkumaran S, Segnitz J. Control of Postpartum Hemorrhage Using Vacuum-Induced Uterine Tamponade. Obstet Gynecol. Jul. 2016; 128(1):33-36. doi: 10.1097/AOG.0000000000001473. PMID: 27275795.

Ram SH, Ram SHS, Ram SS, Panicker V. Vacuum retraction of uterus for the management of atonic postpartum hemorrhage. IOSR J Dent Med Sci (IOSR-JDMS). 2014; e-ISSN: 2279-0853, p-ISSN: 2279-0861. vol. 13, Issue 11 Ver. II, http://www.iosrjournals.org/iosr-jdms/papers/Vol13-issue11/Version-3/D0131131519.pdf.

Rath WH. Postpartum hemorrhage—update on problems of definitions and diagnosis. Acta Obstet Gynecol Scand. May 2011;90(5):421-8. doi: 10.1111/j.1600-0412.2011.01107.x. PMID: 21332452.

Rodriguez MI, Jensen JT, Gregory K, Bullard M, Longo P, Heidel J, Edelman A. A novel tamponade agent for management of post partum hemorrhage: adaptation of the Xstat mini-sponge applicator for obstetric use. BMC Pregnancy Childbirth. Jun. 13, 2017;17(1):187. doi: 10.1186/s12884-017-1373-x. PMID: 28610569; PMCID: PMC5470216.

Shields LE, Smalarz K, Reffigee L, Mugg S, Burdumy TJ, Propst M. Comprehensive maternal hemorrhage protocols improve patient safety and reduce utilization of blood products. Am J Obstet

(56) References Cited

OTHER PUBLICATIONS

Gynecol. Oct. 2011;205(4):368.e1-8. doi: 10.1016/j.ajog.2011.06.084. Epub Jun. 29, 2011. PMID: 22083059.
Suarez S, Conde-Agudelo A, Borovac-Pinheiro A, Suarez-Rebling D, Eckardt M, Theron G, Burke TF. Uterine balloon tamponade for the treatment of postpartum hemorrhage: a systematic review and meta-analysis. Am J Obstet Gynecol. Apr. 2020; 222(4):293.e1-293.e52. doi: 10.1016/j.ajog.2019.11.1287. Epub Jan. 6, 2020. PMID: 31917139.
Svanström MC, Biber B, Hanes M, Johansson G, Näslund U, Bålfors EM. Signs of myocardial ischaemia after injection of oxytocin: a randomized double-blind comparison of oxytocin and methylergometrine during Caesarean section. Br JAnaesth. 2008; 100:683-689.
Vallera C, Choi LO, Cha CM, Hong RW. Uterotonic medications: oxytocin, methylergonovine, carboprost, misoprostol. Anesthesiol Clin. 2017;35:207-219. https://doi.org/10.1016/j.anclin.2017.01.007.
Wright CE, Chauhan SP, Abuhamad AZ. Bakri balloon in the management of postpartum hemorrhage: a review. Am J Perinatol. Nov. 2014;31(11):957-64. doi: 10.1055/s-0034-1372422. Epub Apr. 4, 2014. PMID: 24705972.
Ko MJ, Lim CY. General considerations for sample size estimation in animal study. Korean J Anesthesiol. Feb. 2021;74(1):23-29. doi: 10.4097/kja.20662. Epub Jan. 26, 2021. PMID: 33535728; PMCID: PMC7862939.
Trost SL, Beauregard J, Njie F, et al. Pregnancy-Related Deaths: Data from Maternal Mortality Review Committees in 36 US States, 2017-2019. Atlanta, GA: Centers for Disease Control and Prevention, US Department of Health and Human Services; 2022.

* cited by examiner

100

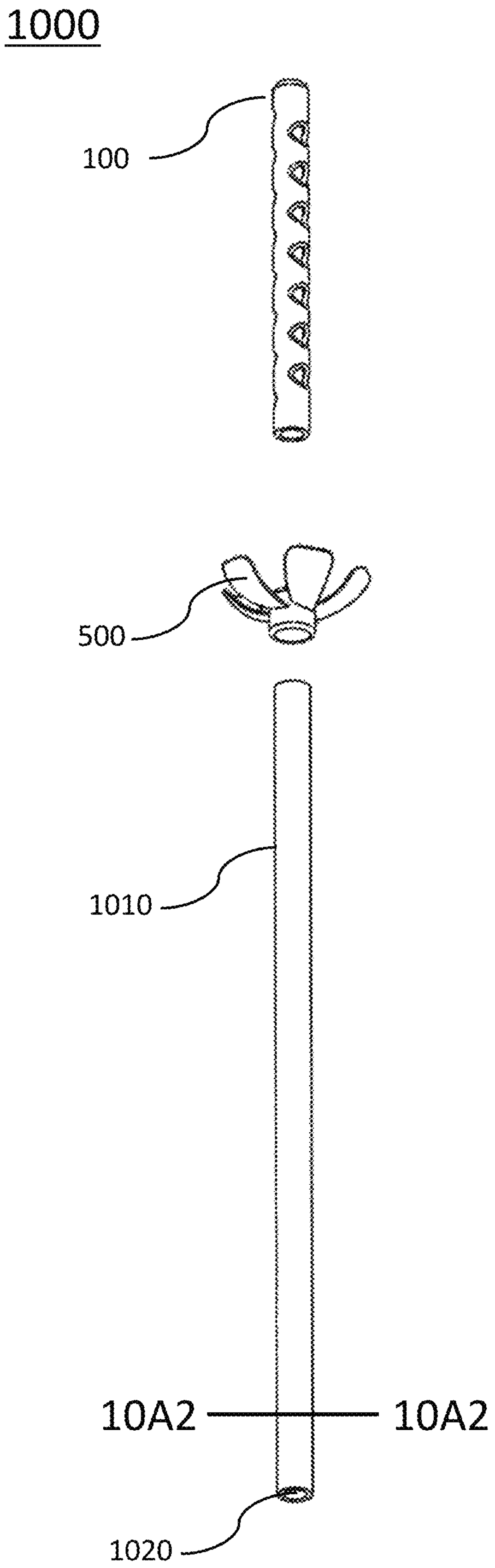
FIG. 10A1
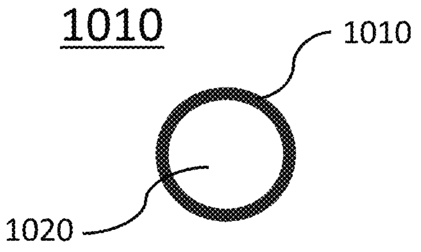
Section 10A2-10A2
FIG. 10A2

1700

1900

SURGICAL DRAINS AND SYSTEMS AND METHODS FOR USING SAME

RELATED APPLICATIONS

This application is a Continuation of International Application Number PCT/US2024/010578, filed 5 Jan. 2024 and entitled "Surgical Drains and Systems and Methods for using Same, which is a of NON-PROVISIONAL of, and claims priority to U.S. Provisional Patent Application No. 63/437,590, filed 6 Jan. 2023 and entitled Systems, Devices, and Methods For Applying Negative Pressure To a Hollow Organ, Draining A Hollow Organ, and Monitoring Blood Loss" and U.S. Provisional Patent Application No. 63/456,419, filed 31 Mar. 2023 and entitled "Systems, Devices, and Methods for Applying Negative Pressure to a Hollow Organ, Draining a Hollow Organ, and Monitoring Blood Loss From a Hollow Organ," both of which are incorporated by reference herein.

BACKGROUND

Blood vessels within and/or adjacent to hollow organs may hemorrhage in response to, for example, trauma or surgery. In particular, blood vessels within a uterus may remain open and/or bleeding following delivery of a fetus, and, in some cases, postpartum hemorrhage may occur when the uterus bleeds more than 1000 mL of blood within the first 24 hours following caesarean delivery of a child. Often, the condition is caused when the woman's uterus fails to contract postpartum, which leaves blood vessels within the uterus open, so they continue to bleed. Postpartum hemorrhage may lead to a significant loss of blood from, and in extreme cases death of, the woman.

Traditionally, it is difficult to diagnose and/or determine the amount of postpartum hemorrhage because it is difficult to determine or measure the volume of postpartum blood-loss, as there are inadequate means to capture the blood and accurately measure it. This is further complicated by blood pooling in the uterine cavity over time. This pooled blood may be held in place via, for example, a blood clot that forms at the base of the uterus and covers the opening to the cervical canal so that the woman may be bleeding internally (occult blood loss) with no vaginal bleeding to alert medical staff that postpartum hemorrhage may be occurring.

SUMMARY

Disclosed herein are surgical drains, systems that include surgical drains, and methods of draining fluid (e.g., blood, urine, etc.) from tissue (e.g., breast, lung, abdomen) and/or an organ such as a hollow organ (e.g., a uterus, bladder, or stomach). The surgical drains may include a tube, a drainage component, and an positioning mechanism. The tube may have a first end, a second end, and a tube lumen. The first end may be configured to couple to a source of suction such as a vacuum pump or wall suction, a fluid collection container (e.g., bag or cannister), passive drain, and/or other fluid collection tool (e.g., gauze, fabric, maxi pad, and/or bandage). Systems for draining a hollow organ and/or tissue may include surgical drains as described herein, a fluid collection device, and/or a source of suction (e.g., wall suction, bulb drain, and/or a vacuum pump).

The drainage component may include a drain lumen in communication with the tube lumen and a plurality of drainage holes sized that may, for example, be linearly arranged along a top and a bottom of the drainage component and configured to allow fluid to enter the drain lumen and be communicated to the tube lumen. The drainage component may be positioned proximate to and/or coupled to the second end of the tube. In some embodiments, each of the plurality of drainage holes may be the same size. Alternatively, one or more drainage holes of the plurality of drainage holes may be of different sizes. For example, the plurality of drainage holes may include a first set of drainage holes proximate to the positioning mechanism that may be of a larger than a size of a second set of drainage holes of the plurality of drainage holes that may be positioned further away from the positioning mechanism.

The drainage component may be configured to extend into (e.g., stand up within) a cavity of a hollow organ without touching, or minimally touching, a sidewall, or interior surface, of the hollow organ. When negative pressure is applied to the drainage component via, for example, a source of suction in communication with the tube lumen, this negative pressure may be communicated to the hollow organ so that, for example, a volume of the hollow organ contracts and/or fluid is evacuated from the hollow organ.

The positioning mechanism may include a shaft configured to encircle a junction between the tube and the drainage component and a plurality of extensions that extend from the shaft. The extensions may be configured to articulate between an open, or unfolded, configuration and a closed, or folded, configuration in response to force exerted thereon as may occur when, for example, the surgical drain is pushed and/or pulled through an opening (e.g., natural orifice or surgical opening) or canal (e.g., cervical canal, vaginal canal, urethra, etc.) with an internal diameter smaller than an external diameter of the positioning mechanism and/or one or more extensions thereof. In some embodiments, this articulation may be facilitated by a hinge and/or a living hinge positioned at an intersection of the shaft and one or more of the extensions. In some embodiments, such as when the attachment mechanism is molded in one piece, the hinge may be in the form of a notch and/or may be a portion of an extension positioned proximate to the shaft that has a narrower width than a remainder of the extension.

One or more extensions of the plurality of extensions may have a uniform width along its length. Additionally, or alternatively, one or more extensions of the plurality of extensions may have a curved shape along its width. Additionally, or alternatively, one or more extensions of the plurality of extensions may have a tapered width along its length so that a width of the one or more extensions is narrower at a joint between the respective extension and the shaft. In some embodiments, the plurality of extensions may include a set of small extensions and a set of large extensions that may be interleaved with one another.

In some embodiments, the positioning mechanism may be sized, positioned, and configured to be positioned proximate to a patient's internal cervical os when the surgical drain is inserted into and/or positioned within a uterus of the patient via a surgical opening in the uterus and the tube may be sized and configured to extend along the patient's vaginal canal so that the first end may be positioned outside the vagina. Additionally, or alternatively, the positioning mechanism may be sized, positioned, and configured to provide tactile feedback to a user, the tactile feedback indicating when the positioning mechanism may be positioned proximate to a patient's cervix when the surgical drain may be inserted into a uterus of the patient via a surgical opening in the uterus and the tube may be sized and configured to extend along the patient's endocervical canal so that the first end may be positioned outside the vagina when coupled to the source of suction. Additionally, or alternatively, the positioning mechanism may be sized, positioned, and configured to provide visual feedback to a user and/or may be configured to be easily viewable in a surgical field because the positioning mechanism may be a color known to visually contrast with blood, such as blue, yellow, neon yellow, and/or neon orange.

In some embodiments, the surgical drain may further include a removable stylet with a stiffening member, or extension, and a tip positioned proximate to the first end of the tube. The stiffening member may be configured, sized, and positioned to reside within the tube lumen of the tube and, in some embodiments, a portion of the drainage component and add stiffness to the surgical drain, which may prevent deformation (e.g., kinking, bunching, folding, etc.) of the surgical drain while it is inserted into the patient's hollow organ and/or tissue for use. The tip may be coupled to (e.g., over-molded onto, chemically and/or heat bonded to, etc.) the stiffening member. Once the first end of the tube has exited the body, a clinician may pull on the tip to extract the stylet from the tube lumen, thereby opening the tube lumen so that fluids that enter the drainage component may travel through, and exit, the tube lumen. In some embodiments, the first end of the tube may be coupled to a source of suction that may apply negative pressure to the tube, and by extension, the drainage component and hollow organ and/or tissue. This negative pressure may act to contract the hollow organ thereby applying tamponade to blood vessels (e.g., open or bleeding blood vessels of the hollow organ, which may act to assist with the closing of blood vessels within the hollow organ (thereby reducing blood flow therefrom into the hollow organ) and/or facilitate restoration of tone to the hollow organ. Additionally, or alternatively, the first end of the tube may be coupled to a volumetric measuring device (e.g., a bag or canister) to measure a volume of fluid being drained from the hollow organ via the surgical drain.

Methods for using a surgical drain, placing a surgical drain within a hollow organ such as a uterus, treating post-partum hemorrhage, and/or draining a hollow organ as disclosed herein may include guiding a first end of a tube of a surgical drain as shown and described herein through a hysterotomy, uterine cavity, cervical canal, and vaginal canal of a patient until an positioning mechanism of the surgical drain is positioned within the uterine cavity of the patient proximate to the patient's cervix and/or an internal cervical os of the patient. When the positioning mechanism is so positioned, a drainage component of the surgical drain may extend into a cavity of the uterus and the first end of the tube may extends through an introitus of the patient. The first end of the tube may be coupled to, for example, a source of suction configured to apply negative pressure to the surgical drain and, by extension, the uterine cavity. On some occasions, a portion of the tube extending from the patient's introitus may be secured (e.g., tape) to patient's leg prior to or after coupling the first end of the tube to a source of suction. In some embodiments, the hysterotomy may be surgically closed prior to application of suction to the surgical drain.

On some occasions, a removable stylet may be resident within a portion of the tube lumen and may be configured and/or arranged to assist with guiding the first end of the tube through the hysterotomy, uterine cavity, cervical canal, and vaginal canal of the patient. Once the surgical drain is properly in place, the stylet may be removed from the tube via, for example, grasping and pulling the tip away from the first end of the tube. Once the stylet is removed from the tube lumen, tube and drain lumens may facilitate evacuation of fluids and/or gas from the uterus and away from the body.

When use of the surgical drain is complete, the surgical drain may be extracted from the uterus by, for example, pulling the first end of the tube until the entire surgical drain exits the introitus of the patient.

Methods for evacuating fluid from a uterus of a patient, applying suction tamponade to a patient's uterus and/or preventing post-partum hemorrhage following child delivery via caesarian section may include placing a surgical drain as, for example, shown and described herein, in the patient's body so that a drainage component of the surgical drain extends into a uterine cavity of the patient and a portion of a tube of the surgical drain extends through a cervical canal and a vaginal canal of the patient, wherein the drainage component includes a drain lumen in communication with a tube lumen and the drainage component includes at least one opening configured to allow fluid to enter the drainage lumen to be evacuated from the uterus via the tube lumen. The surgical drain may be placed within the patient's uterus via, for example, a hysterotomy.

Additionally, or alternatively, a first end of a surgical drain may be inserted into the patient's uterus via a surgical opening therein and the first end of the surgical drain may be guided through the patient's uterine cavity, cervical canal, and vaginal canal until the first end of the surgical drain exits an introitus of the patient and a second end of the surgical drain extends into the uterine cavity of the patient, thereby allowing blood to drain from the patient's uterus.

In some embodiments, the surgical drain may include an positioning mechanism and may be placed within the patient so that the positioning mechanism is positioned proximate to an internal cervical os of the patient. The positioning mechanism may be configured to provide tactile feedback to a clinician placing the surgical drain within the patient's uterus so that, for example, the clinician can feel when the positioning mechanism is proximate to the internal cervical os. At times, the positioning mechanism may include one or more extensions that may extend approximately perpendicularly from the tube. The one or more extensions may be configured to between a folded and unfolded configuration in response to force exerted thereon as, for example, a surgical drain including an positioning mechanism travels through a hysterotomy, cervical canal, and/or vaginal canal so that the surgical drain with the positioning mechanism may be atraumatically placed and/or moved within the patient's body.

In some embodiments, the first end of the tube may be coupled to a source of suction and negative pressure may be applied to the tube using the source of suction. This negative pressure may be communicated to the uterine cavity via the tube lumen, drain lumen, and drainage hole(s) and may act to, for example, contract the uterine cavity (i.e., apply suction tamponade) and/or pull fluid from the uterine cavity into the drainage hole(s), through the drain lumen and the tube lumen and out of the patient's body and, on some occasions, into a collection device such as a canister, volumetric bag, gauze, etc. On some occasions, a volume of fluid and/or blood evacuated from the patient's uterus and present in the collection device may be measured to, for example, determine a volume of blood loss, a rate of blood loss and/or whether or not an intervention (e.g., blood transfusion) or extraction of the surgical drain is required or desired. When the surgical drain is no longer needed (e.g., once the patient's bleeding has sufficiently slowed or stopped), the surgical drain may be from the patient's uterus via, for example, pulling the surgical drain through the patient's cervical canal, vaginal canal, and out of the patient's introitus.

BRIEF DESCRIPTION OF THE DRAWINGS

The present invention is illustrated by way of example, and not limitation, in the figures of the accompanying drawings in which:

FIG. 10A1 is a schematic diagram of an exploded view of a first exemplary surgical drain, in accordance with some embodiments of the present invention;

FIG. 10A2 is schematic diagram of a cross-section view of a portion of first exemplary surgical drain, in accordance with some embodiments of the present invention;

Figure 1A:
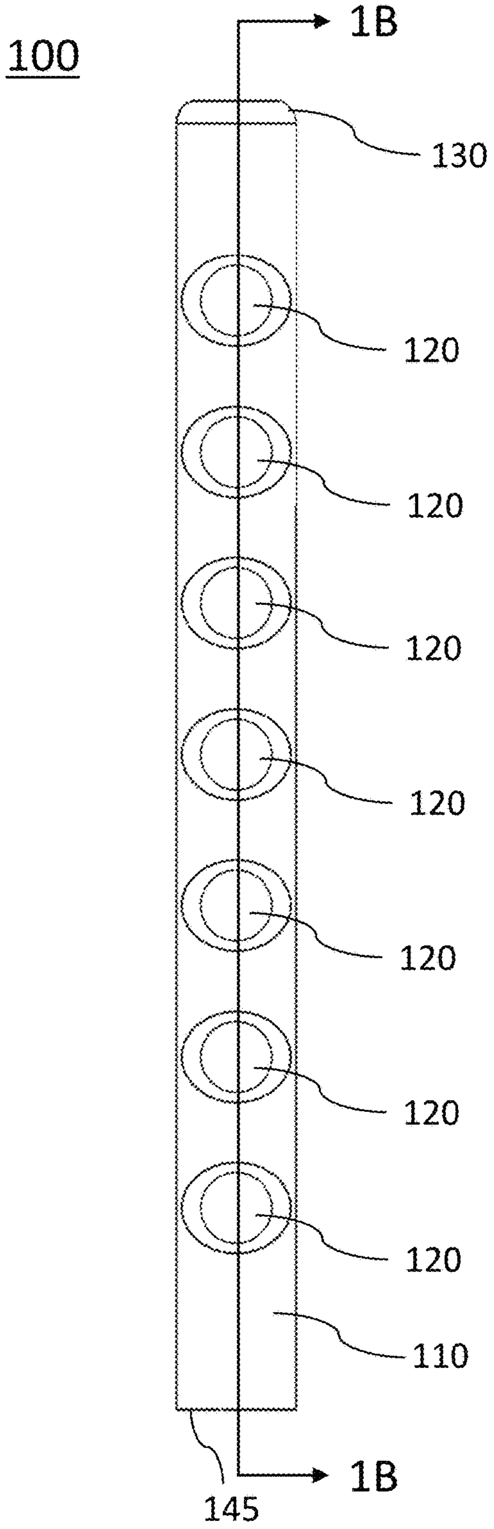
FIG. 1A is a schematic diagrams that illustrate various views of a first drainage component that may be used with a surgical drain, in accordance with some embodiments of the present invention.

Throughout the drawings, the same reference numerals, and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

Written Description

The surgical drains systems, devices, and methods disclosed herein are configured to apply negative pressure to internal surfaces of a hollow organ such as a uterus, stomach, or bladder in order to, for example, contract the hollow organ so that, for example, the hollow organ achieves a preferred size and/or blood vessels that may be open, or bleeding into the hollow organ, are constricted which may assist with, for example, staunching the bleeding and/or clot formation within the hollow organ so that hemorrhaging may be reduced and/or stopped.

The systems, devices, and methods disclosed herein may also be configured to evacuate, or drain, fluid (e.g., blood or urine), solids (e.g., blood clots or tissue fragments) and/or gas from a hollow organ and/or tissue following, for example, childbirth, child delivery via caesarean section, endoscopic surgery (e.g., tumor removal) and/or open surgery (e.g., a hysterotomy). At times, the fluid and/or material drained, or evacuated, from a hollow organ and/or tissue may be collected (e.g., using a metered collection bag and/or vessel with approximate volumetric markers) so that, for example, a quantity of fluid and/or material evacuated from the hollow organ and/or tissue may be quantified to determine, for example, how much blood the patient may have lost, which may be used by a clinician to determine whether the patient needs medical attention and/or an intervention (e.g., a blood transfusion or cauterization of a blood vessel within the hollow organ and/or tissue). Additionally, or alternatively, the fluid and/or material drained, or evacuated, from a hollow organ and/or tissue may be examined to, for example, determine how many blood clots are present in the evacuated fluid/material and/or the size of the blood clots present in the evacuated fluid and/or material. In some embodiments, a flow rate of fluid or blood being evacuated from the hollow organ and/or tissue may be measured and/or evaluated to ascertain whether, for example, the patient is bleeding at a rate that may require medical attention and/or an intervention (e.g., a blood transfusion or cauterization of a blood vessel within the hollow organ and/or tissue).

In some instances, relative sizes and/or proportions of surgical drain components disclosed herein may be adjusted based upon the clinical need and application. For example, a tube for a surgical drain configured for use with evacuating fluid, gas, and/or material from a stomach via the esophagus may be longer than a tube used to evacuate a bladder via a surgical opening.

The systems and devices disclosed herein may be referred to as surgical drains. Each of the surgical drains disclosed herein include a tube, an positioning mechanism, and a drainage component. The tube and drainage component may each include a lumen that are in communication with one another. The drainage component is configured to be placed within the hollow organ and/or tissue and evacuate fluid, gas, and/or solids from the hollow organ and/or tissue via one or more holes or openings present in the drainage component. The holes may be configured to have a smooth, or flat, profile to enable an atraumatic extraction of a surgical drain from the hollow organ and/or tissue. In some cases, drainage component holes may be of varying sizes to, for example, accommodate passage of clots that may be expected to form or collect at, or near, a lower portion of the hollow organ and/or tissue (e.g., proximate to the cervix) due to gravity. When fluids, gas, and/or solids enter one or more drainage holes of a drainage component, they may travel (via, e.g., suction and/or gravity) to the drainage component lumen and the tube lumen for eventual evacuation from the patient's body.

In some embodiments, the drainage components may include two linearly arranged sets of holes, or openings, that may be offset from one another by, for example, 180 degrees. Alternatively, the drainage components may include three linearly arranged sets of holes, or openings, that may be offset from one another by, for example, 120 degrees. Alternatively, the drainage components may include plurality of holes, or openings, that are arranged in a circumferential, spiral, and/or random pattern around the drainage component. In some embodiments, the holes within the drainage component may be arranged so that the structural integrity and/or columnal strength of the drainage component is maintained and/or meets minimum requirements. In some cases, the holes may be configured and/or arranged within a drainage component so that it aligns with a frontal plane of the hollow organ (e.g., uterus) and/or tissue so that, for example, when the hollow organ contracts in response to negative pressure applied thereto via the surgical drain, interior tissue of the hollow organ may not enter and/or be pulled proximate to the holes, which may occlude the holes and/or prevent drainage therefrom. In some embodiments, an orientation of a drainage component may be adjustable so that, for example, it may be rotated by a clinician so that the drainage holes are pointed to a preferred portion of the hollow organ and/or tissue, such as an incision site.

A tube of the surgical drains disclosed herein may be configured to extend through a portion of the body that is not a hollow organ (e.g., cervical canal, vaginal canal, esophagus, or surgical opening in, for example, the abdomen when the organ is a bladder or stomach) and couple the drainage component to a source of negative pressure (i.e., a vacuum pump) that may suck gas, fluid, and/or solids into one or more holes of the drainage component for eventual evacuation from the hollow organ via the drainage component lumen and the tube lumen.

The positioning mechanisms disclosed herein may be configured to translate between an open and a closed, or collapsed, configuration. When in an open, or unfolded, configuration, the positioning mechanisms disclosed herein may be configured to hold a drainage component in a preferred position and/or orientation (e.g., fully inserted therein or positioned along a length of the hollow organ and/or tissue) within the hollow organ and/or tissue. For example, when a surgical drain (or drainage component thereof) is positioned within a uterus, the positioning mechanism may be positioned proximate to the internal cervical os, which may provide visual (e.g., extensions are spread out over and/or partially cover the internal cervical os) and/or tactile (e.g., pushback from the cervix) feedback to a clinician inserting the surgical drain, which may help guide insertion of the surgical drain and/or indicate that the surgical drain is in a proper position within the uterine cavity. At times, the positioning mechanism may also prevent the drainage component from undesirably sliding into the cervical and/or vaginal canal. Additionally, or alternatively, the positioning mechanisms disclosed herein may be configured to reduce movement of the surgical drain, or components thereof, when the drainage component is positioned within the hollow organ and/or tissue. This may reduce irritation and tissue damage that may be caused by movement of the surgical drain when positioned and/or used within a hollow organ and/or tissue and/or tissue of the patient. At times, the positioning mechanism may be weighted to, for example, use gravity to hold the positioning mechanism at a lowest point of the hollow organ and/or tissue.

When transitioning to a closed state, components (e.g., extensions) of an positioning mechanism may be configured to bend, fold, or collapse, to reduce the cross-sectional area of the extensions/positioning mechanism. For example, in some embodiments, one or more components of an positioning mechanism may fold, or translate, toward the drainage component so that a diameter of the positioning mechanism is reduced to achieve a streamlined profile for the surgical drain, which may reduce trauma caused to tissue when the surgical drain is extracted from the patient's hollow organ and/or tissue (e.g., pulled through the cervix). In many embodiments, the positioning mechanism may translate to a collapsed state that has a relatively smooth or ridge-free exterior surface thereby assisting with extraction of the surgical drain and reducing trauma to surrounding tissue with the surgical drain is extracted.

Oftentimes, the surgical drains disclosed herein may be inserted into and/or placed within a hollow organ and/or tissue and/or tissue via a surgical incision therein and a portion of the surgical drain may be arranged to extend away from the hollow organ and/or tissue and exit the body via, for example, a natural orifice (e.g., vagina or urethra) and/or surgically-made opening, thereby providing an exit channel for draining fluid away from the hollow organ and/or tissue following, for example, surgery or trauma. For example, a surgical drain may be placed within a uterine cavity via a uterine incision (hysterotomy) at the conclusion of pelvic surgery following, for example, childbirth via caesarian section. The surgical drain may be placed by threading it through the uterine cavity, cervical canal, vaginal canal, and out the introitus, thereby making a distal end accessible outside of the body so that, for example, it may be coupled to a suction source.

Figure 1B:
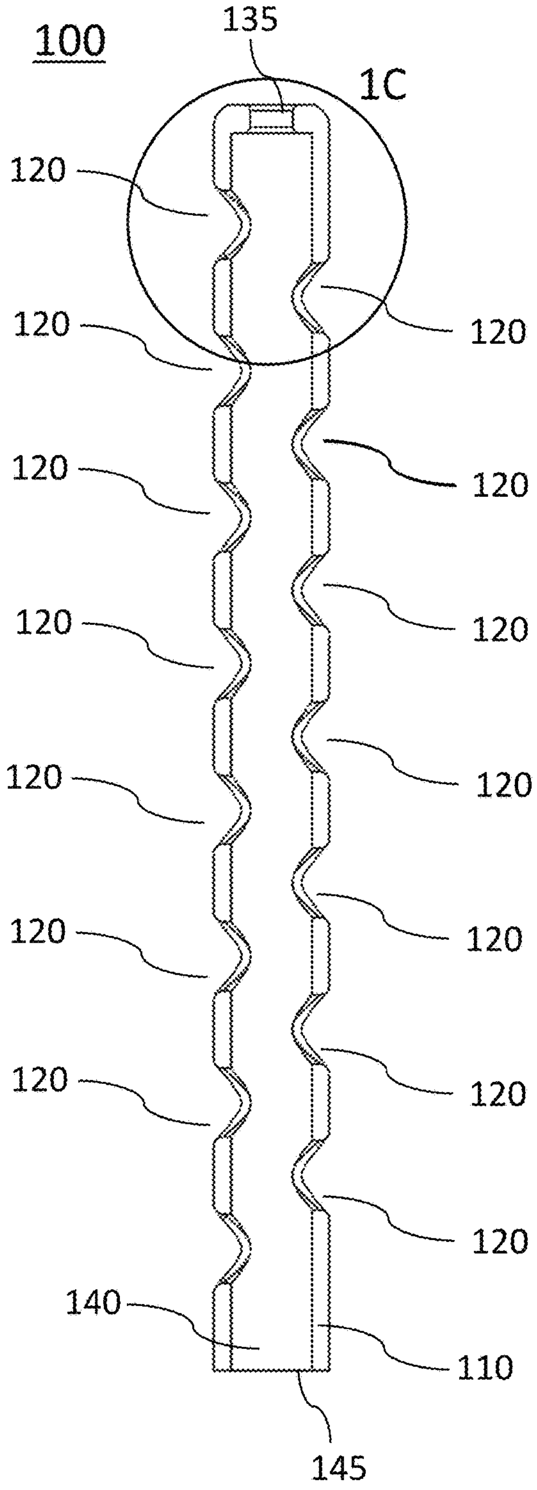
FIG. 1B is a schematic diagram of a first vertical cross-section view of the drainage component of FIG. 1A, in accordance with some embodiments of the present invention.
Figure 1C:
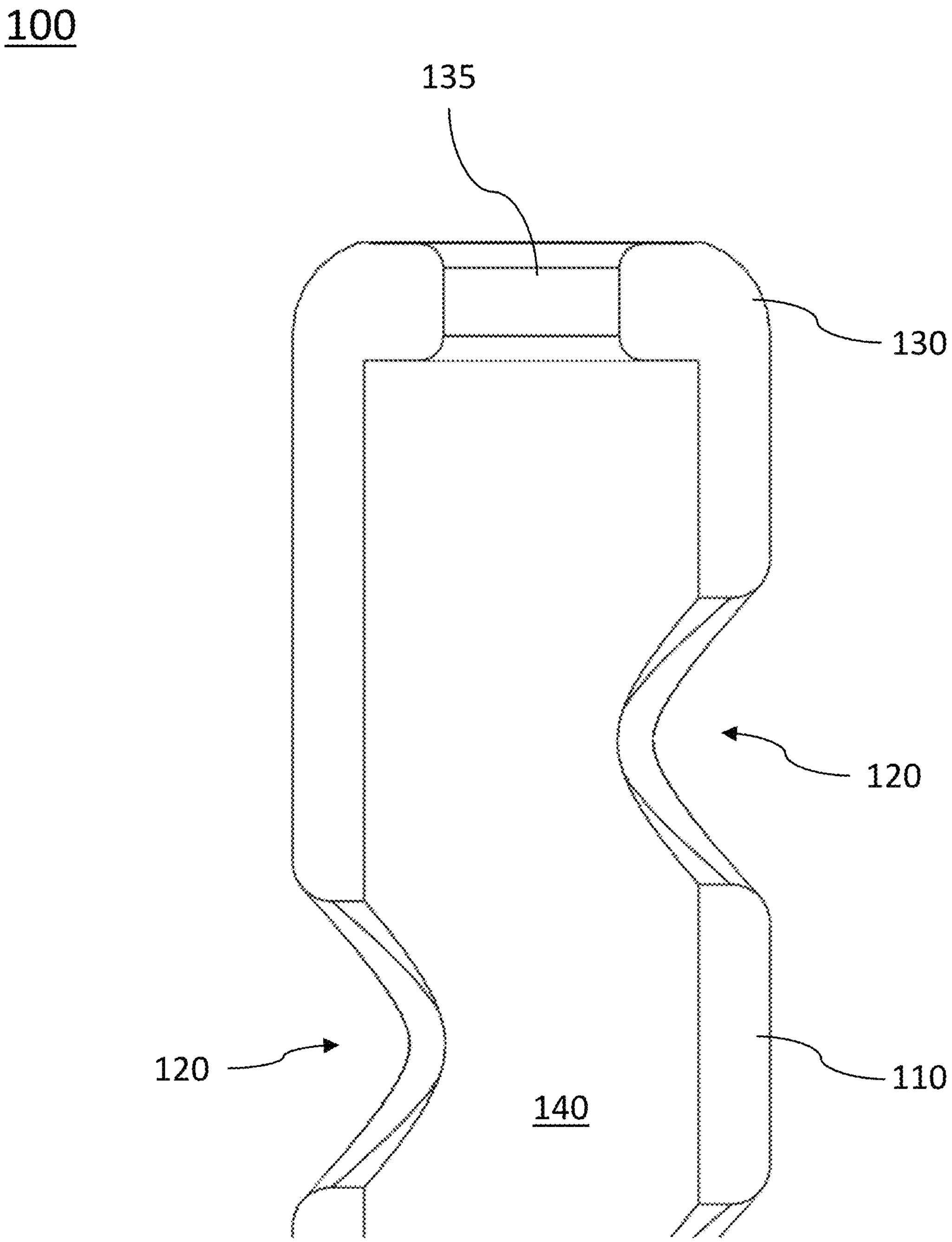
FIG. 1C is a schematic diagram of a detailed close up view of an upper portion of the cross-section of the drainage component shown in FIG. 1B, in accordance with some embodiments of the present invention.
Figure 1D:
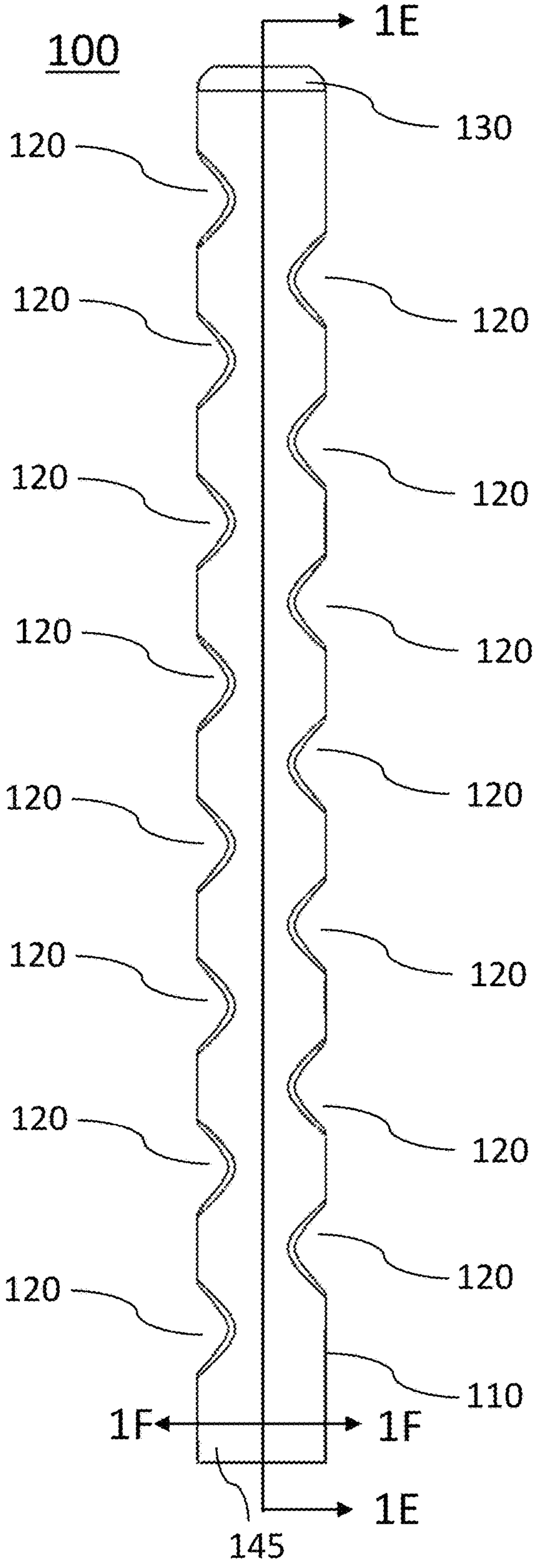
FIG. 1D is a schematic diagram of a side view of the drainage component of FIG. 1A, in accordance with some embodiments of the present invention.
Figure 1E:
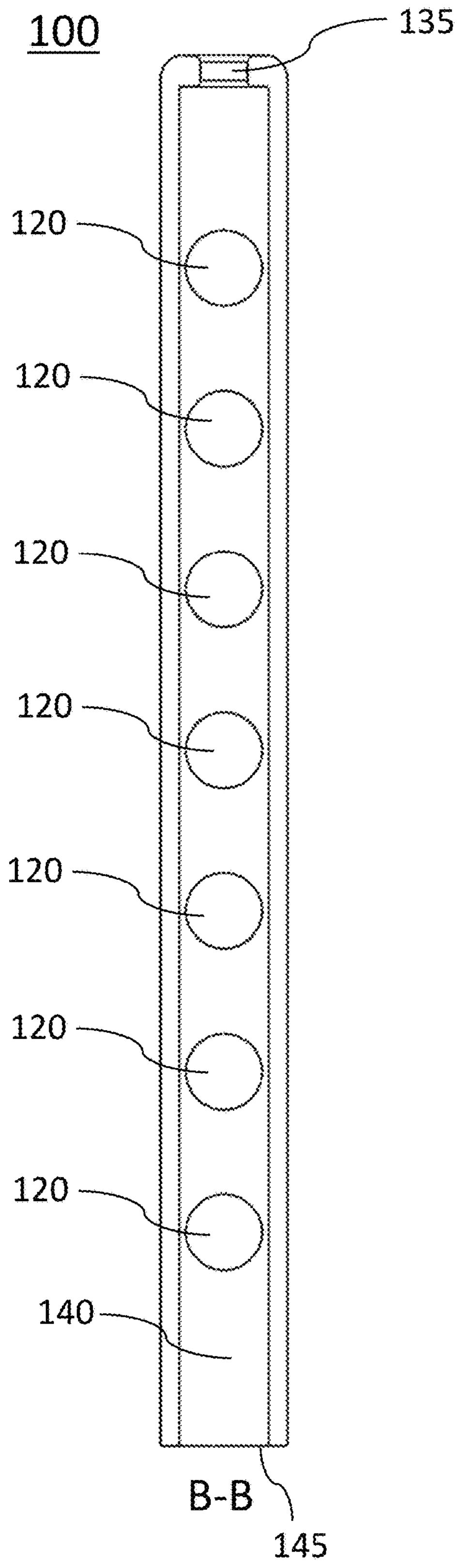
FIG. 1E is a schematic diagram of a second vertical cross-section view of the drainage component of FIG. 1A, in accordance with some embodiments of the present invention.
Figure 1F:
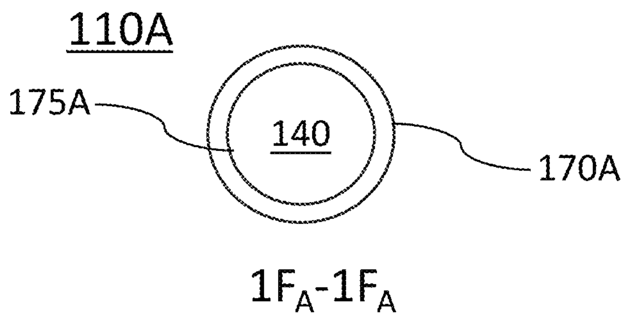
FIG. 1F is a schematic diagram of a horizontal cross-section view of drainage component of FIG. 1A with a first cross-sectional shape, in accordance with some embodiments of the present invention.
Figure 1G:
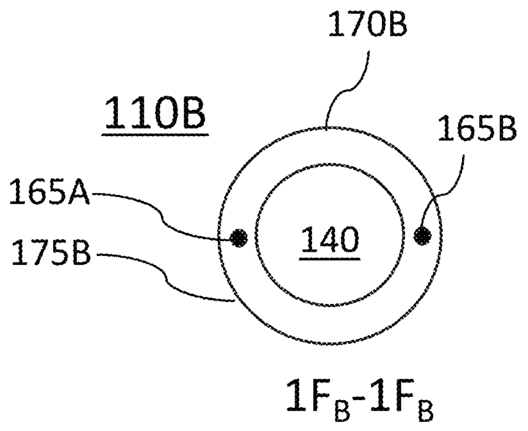
FIG. 1G is a schematic diagram of a horizontal cross-section view of drainage component of FIG. 1A with a second cross-sectional shape, in accordance with some embodiments of the present invention.
Figure 1H:
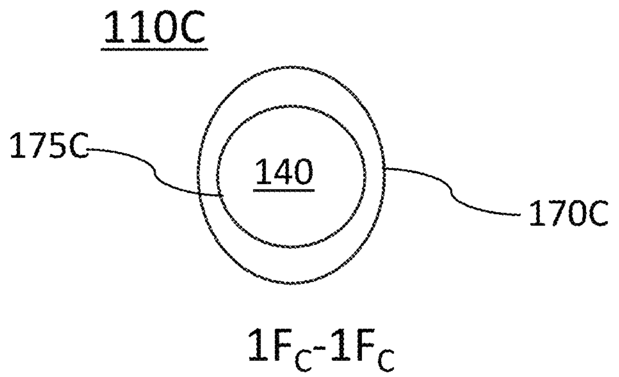
FIG. 1H is a schematic diagram of a horizontal cross-section view of drainage component of FIG. 1A with a third cross-sectional shape, in accordance with some embodiments of the present invention.
Figure 1I:
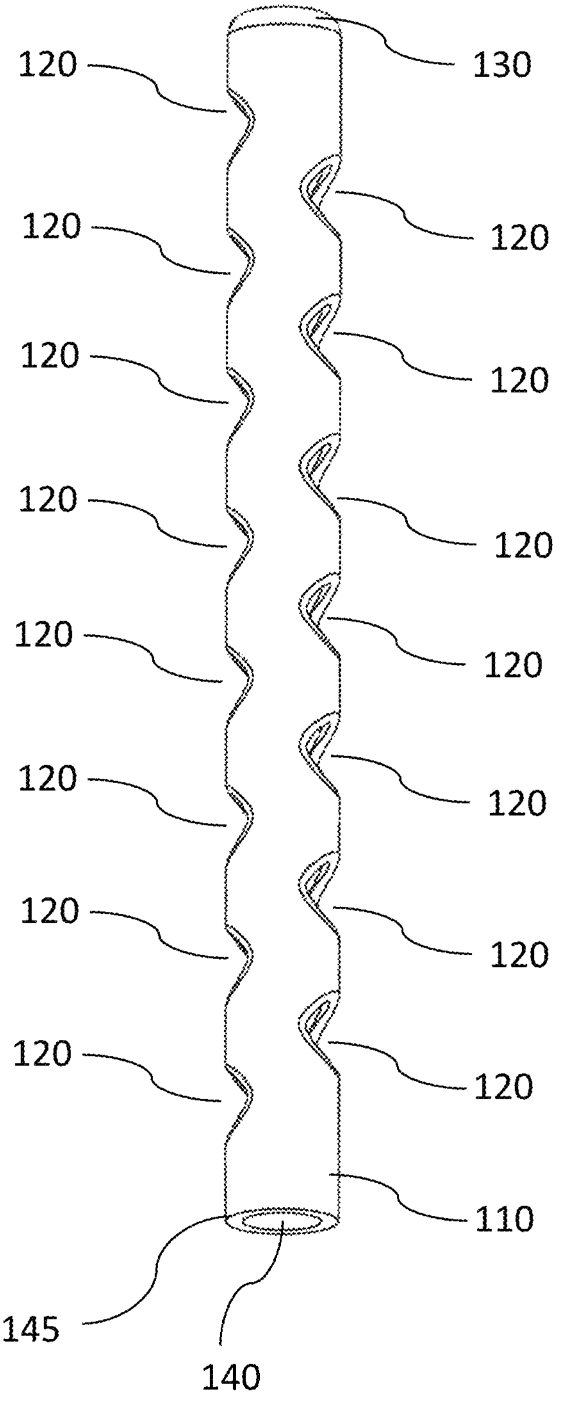
FIG. 1I is a schematic diagram of a perspective view of the drainage component of FIG. 1A, in accordance with some embodiments of the present invention.

Turning now to the figures, FIGS. 1A-1I are schematic diagrams, or renderings, that provide various views of a first drainage component 100 that may be used with a surgical drain such as the surgical drains described herein. In particular, FIG. 1A provides a top view of drainage component 100; FIG. 1B provides a vertical (as oriented FIG. 1A) cross-section of drainage component 100 taken along bisecting line 1B-1B (shown in FIG. 1A); FIG. 1C is a detailed view 1C of an upper (as oriented in FIG. 1B) portion of the cross-section of drainage component 100 shown in FIG. 1B; FIG. 1D provides a side view of drainage component 100; FIG. 1E provides a vertical (as oriented in FIG. 1D) cross-section view of drainage component 100 taken along bisecting line 1E-1E as shown in FIG. 1D; FIG. 1F provides a horizontal (as oriented in FIG. 1D) cross-section view of drainage component 100 with a first cross-sectional shape taken along bisecting line 1F-1F as shown in FIG. 1D; FIG. 1G provides a horizontal (as oriented in FIG. 1D) cross-section view of drainage component 100 with a second cross-sectional shape taken along bisecting line 1F-1F as shown in FIG. 1D; FIG. 1H provides a horizontal (as oriented in FIG. 1D) cross-section view of drainage component 100 with a third cross-sectional shape taken along bisecting line 1F-1F as shown in FIG. 1D; and FIG. 1I provides a perspective view of drainage component 100. Exemplary dimensions for first drainage components include an overall length of 50-400 mm, an overall width of 3-15 mm, and an interior diameter of 1.5-13.5 mm.

Drainage component 100 includes a body 110 in the general shape of a tube with a first end 130, an optional drain end 135 configured to be permanently or removably positioned within first end 130, an open end 145, and a central lumen 140 running the along the length of body 110. In some embodiments, drain cap 135 may be removable so that, for example, fluid and/or gas may be exchanged via lumen 140, which would be open, or exposed, following removal of drain cap 135. At times, a shape of first end 130 may be configured so that it is atraumatic (e.g., avoids poking or sucking of tissue into drainage component 100) to tissue within the hollow organ and/or tissue into which it is inserted and may have the shape of, for example, a tapered edge, a sphere, a dome, or a funnel.

Drainage component 100 also includes a plurality (in this case, fifteen) of drainage holes 120 that are open to lumen 140 so that body 110 (via drainage holes 120) may be in liquid and/or gaseous communication with lumen 140, thereby allowing gases (e.g., air) and/or liquids (e.g., blood, saline, or bodily fluids) to enter lumen 140 from a hollow organ and/or tissue in which it is placed for eventual evacuation from the hollow organ and/or tissue via, for example, application of negative pressure, or suction, to drainage component 100 and/or a device incorporating drainage component 100 as described herein. In some instances, drainage holes 120 may be beveled, or otherwise configured, to allow for passage of gas, fluid (e.g., blood), and/or material (e.g., blood clots) therethrough without causing trauma to surrounding tissue (e.g., an internal surface of a hollow organ in which a drainage component is placed).

First drainage component 100 may be configured to be flexible and/or compliant when, for example, pressure is exerted thereon so that it may, for example, bend or conform to internal geometry during insertion into a hollow organ and/or tissue and/or reside within a hollow organ and/or tissue in a manner that is atraumatic (e.g., lay within a hollow organ and/or tissue and adapt a curvature that fits within and/or adapts to a curvature of the hollow organ and/or tissue). In some embodiments, first drainage component 100 may be made from silicone or vinyl. As may be seen in FIGS. 1B, 1C, 1D, and 1G, drainage holes 120 positioned on a top of drainage component 100 may be offset (e.g., positioned between) from drainage holes 120 positioned on a bottom of drainage component 100. Offsetting drainage holes 120 in this manner may improve the overall structural integrity of drainage component 100 by allowing for flexibility, for example, in one axis, while maintaining an overall shape that doesn't fold, twist, and/or bend in a manner that may obscure one or more drainage holes 120 and/or prevent communication of gases and/or liquids via lumen 140.

FIGS. 1F-1H provide three exemplary horizontal cross-sectional shapes of body 110 along cross-section line 1F-1F shown in FIG. 1D. In particular, FIG. 1F provides a first horizontal cross-section view $1F_A$-$1F_A$, of a first example of a drainage component body 110A with an interior wall 175A and an exterior wall 170A that are substantially circular in shape with lumen 140 being positioned in an approximate center of the horizontal cross-section of FIG. 1F and being defined by a size and shape of interior wall 175A. FIG. 1G provides a second horizontal cross-section view $1F_B$-$1F_B$, of a second example of drainage component body 110B with an interior wall 175B and an exterior wall 170B that are substantially circular in shape with lumen 140 being positioned in an approximate center of the horizontal cross-section of FIG. 1G and being defined by a size and shape of interior wall 175B. In addition, second exemplary body 110B includes a first and a second stiffening components 165A and 165B positioned within second body 110B between exterior diameter 170B and interior diameter 175B. First and/or second stiffening components 165A or 165B may be configured and/or arranged to add stiffness and/or structural integrity to second body 110B and may be made from any material (e.g., metal, plastic, etc.) that is stiffer/more rigid than a material used to manufacture second body 110B. FIG. 1H provides a third horizontal cross-section view along cross-section line $1F_c$-$1F_c$ of a third exemplary drainage component body 110B that has an exterior surface/diameter 170C that is substantially elliptical in shape and an interior diameter 175C that is substantially circular in shape so that a width of third body 110C is thicker (e.g., 0.1-2 mm) on a top and a bottom (as oriented in FIG. 1H) than on the left and right sides of third body 110C as shown. This elliptical profile, or cross-sectional shape, of body 110C may provide, for example, increased stiffness and/or rigidity for drainage component 100 along its length. Additionally, or alternatively, the elliptical profile, or cross-sectional shape, of body 110C may provide preferential flexibility along one axis of body 110C. At times, an elliptically shaped drainage component, such as third body 110C, may be configured to have a circular cross-section proximate to a coupling, or joint between, the drainage component and another component of a surgical drain (e.g., a tube or positioning mechanism) as shown and discussed herein so that its outer and/or inner diameter may be joined and/or matched a component to which it is coupled.

In some embodiments, a size and/or shape of a drainage holes provided by a drainage component may vary within a particular drainage component, with larger drainage holes being less likely to become clogged or otherwise occluded with, for example, blood clots or tissue. For example, in some embodiments one or more drainage holes proximate to an end cap of a drainage component may be larger than drainage holes proximate to an open end of drainage component. Alternatively, one or more drainage holes proximate to an end cap of a drainage component may be smaller than drainage holes proximate to an open end of drainage component. In some embodiments, larger drainage holes of a drainage component such as the drainage components disclosed herein may be positioned within the drainage component so they correspond to an expected position within a hollow organ and/or tissue where blood clots may form and/or congregate (e.g., due to gravity or other factors) such as at the base of a hollow organ and/or tissue (e.g., proximate to a subject's internal cervical os). Additionally, or alternatively, in embodiments where a surgical drain and/or drainage component is configured to be positioned in a hollow organ and/or tissue following surgery, larger drainage holes may be positioned within a drainage component to correspond to an approximate expected position of the incision site so that, for example, negative pressure, or suction, applied to a lumen of the drainage component may be maximized at locations proximate to the surgical incision in order to, for example, contract the tissue proximate to the incision site to a greater degree than tissue not as proximate to the incision site, which may help hold the incision together and/or drain away fluids from the incision site.

Figure 2A:
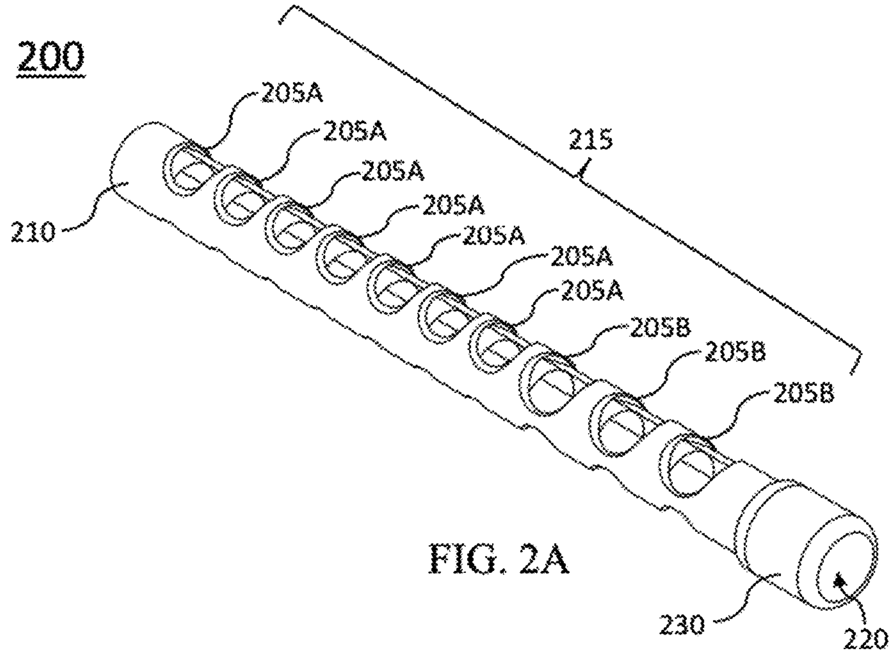
FIG. 2A is a schematic diagram of a top-perspective view of a second drainage component that may be used with a surgical drain, in accordance with some embodiments of the present invention.
Figure 2B:
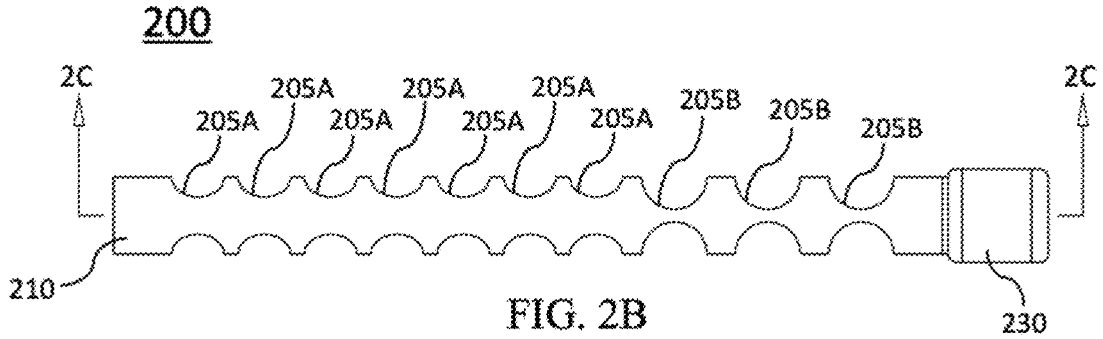
FIG. 2B is a schematic diagram of a side view of the second drainage component of FIG. 2A, in accordance with some embodiments of the present invention.
Figure 2C:
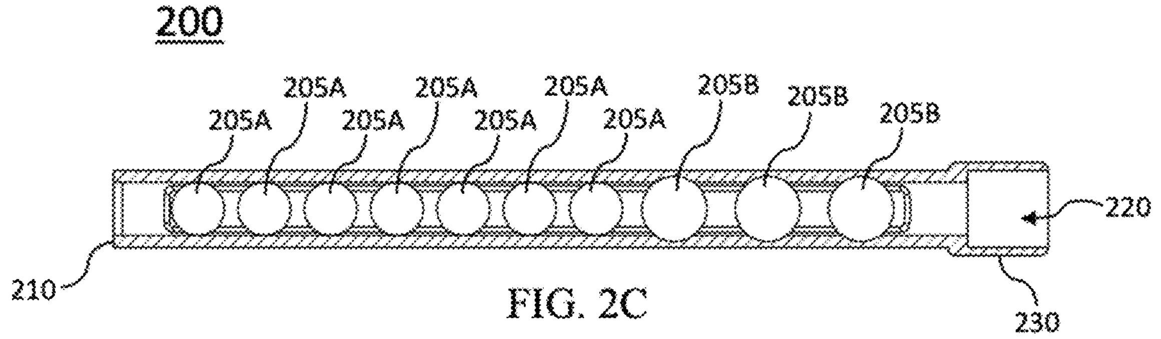
FIG. 2C is a schematic diagram of a horizontal cross-section view of the second drainage component of FIG. 2A, in accordance with some embodiments of the present invention.

FIGS. 2A-2C are schematic diagrams, or renderings, that provide various views of a second exemplary drainage component 200 that may be used with any of the surgical drains disclosed herein. In particular, FIG. 2A is a top-perspective view of second drainage component 200; FIG. 2B provides a side view of second drainage component 200; and FIG. 2C provides a horizontal (as oriented FIG. 2B) cross-section view of second drainage component 200 taken along bisecting line 2C-2C shown in FIG. 2B.

Second drainage component 200 is a hollow tube that, in many cases, may have dimensions that are similar to first drainage component 100 and/or may be configured to function and/or be flexible and/or compliant in a manner similar to first drainage component 100. Second drainage component 200 includes a main body 210, a central lumen 220, a coupling 230, and an array 215 of small drainage holes 205A and large drainage holes 205B. Coupling 230 may be sized, shaped, and/or configured to couple (usually permanently) to another component of a surgical drain, such as an positioning mechanism and/or tube as shown and described herein.

The large and small drainage holes 205A and 205B of second drainage component 200 are configured to function in a manner similar to drainage holes 120 in that each large and small drainage hole 205A and 205B are configured to allow communication and/or exchange with lumen 220 so that, for example, suction applied to second drainage component 200 may be communicated to a hollow organ and/or tissue in which second drainage component 200 is placed and/or liquid or material within the hollow organ and/or tissue may be pass through large and/or small holes 205A and 205B to be evacuated from the hollow organ and/or tissue via lumen 220.

As may be seen in FIGS. 2A-2C, second drainage component 200 includes a plurality (in this case, fourteen) of relatively small drainage holes 205A and a plurality (in this case, six) of relatively large drainage holes 205B positioned proximate to coupling 220 that are arranged on the top and bottom of second drainage component 200 in a linear fashion along the length of second drainage component 200 as shown. Positioning of large drainage holes 205B proximate to coupling 220 may, for example, facilitate increased communication between a hollow organ and/or tissue in which second drainage component 200 is placed at a location within the organ that is positioned lower within the organ/patients body where blood clots are more likely to collect.

The small and large drainage holes 205A and 205B are arranged in pairs that are positioned on opposite sides (e.g., 180 degrees apart) of main body 210 so that each pair of drainage holes 205 provides a pass through from a first side of second drainage component 200 to a second side of drainage component 200 as shown. FIG. 2B is a side view of second drainage component 200 and shows a curved shape of drainage holes 205A and 205B. FIG. 2C is provides a cross-section view along line 2C-2C, which shows how drainage holes 205A and 205B open to lumen 220.

Figure 3:
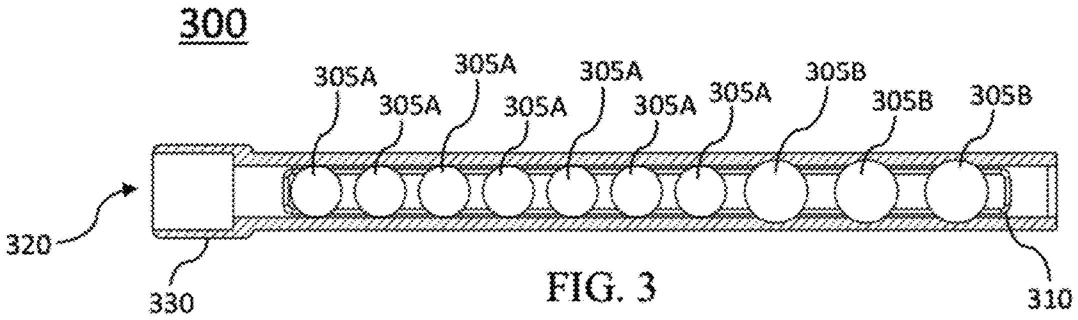
FIG. 3 is a schematic diagram of cross section of a third drainage component that may be used with a surgical drain, in accordance with some embodiments of the present invention.

FIG. 3 is a schematic diagram, or rendering, of a third exemplary drainage component 300 that may be used with any of the surgical drains disclosed herein. Third drainage component 300 is a hollow tube that, in many cases, may have dimensions that are similar to first and/or second drainage component 100 and/or 200 and/or may be configured to function and/or be flexible and/or compliant in a manner similar to first and/or second drainage component 100 and/or 200. Third drainage component 300 includes a main body 310, a central lumen 320, a coupling 330, a plurality of small drainage holes 305A and a plurality of large drainage holes 305B. Coupling 330 may be sized, shaped, and/or configured to couple (usually permanently) to another component of a surgical drain as shown and described herein.

The large and small drainage holes 305A and 305B of third drainage component 300 are configured to function in a manner similar to large and small drainage holes 205A and 205B, respectively, of second drainage component 200. Third drainage component 300 includes a plurality (in this case, fourteen) of relatively small drainage holes 305A positioned proximate to coupling 330 and a plurality (in this case, six) of relatively large drainage holes 305B. Positioning of large drainage holes 305B away to coupling 330 may facilitate increased communication between a hollow organ and/or tissue in which third drainage component 300 is placed at a location within the organ that is proximate to, for example, an incision or trauma site so that, for example, increased suction and/or tamponade may be applied to the position within the hollow organ and/or tissue proximate to the incision or trauma site to, for example, hold a sutured incision together, facilitate rapid healing, and/or evacuate of fluids from the area.

Figure 4A:
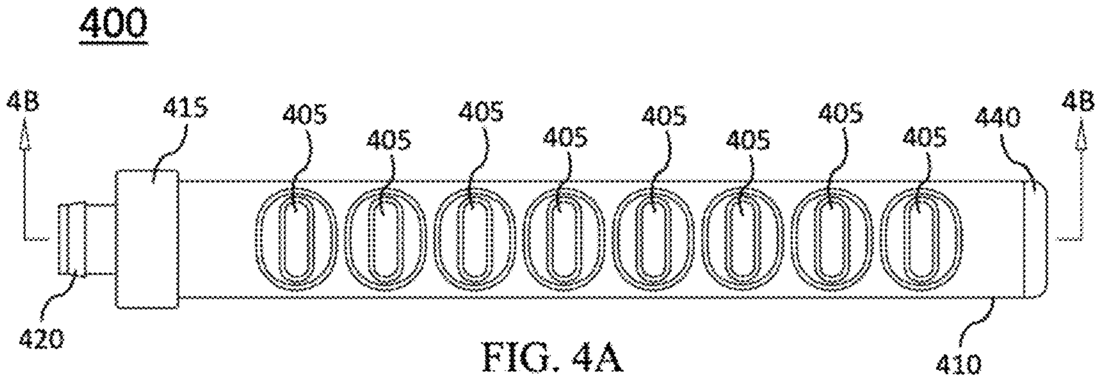
FIG. 4A is a schematic diagram of a top view of a fourth drainage component, in accordance with some embodiments of the present invention.
Figure 4B:
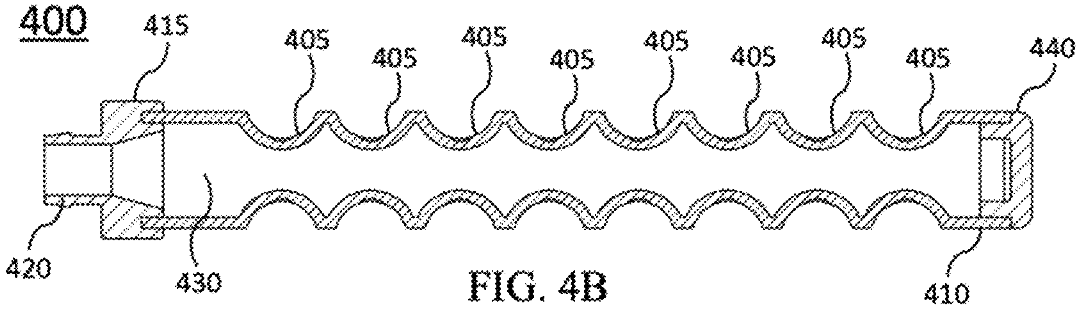
FIG. 4B is a schematic diagram of a horizontal cross-section view of the fourth drainage component of FIG. 4A, in accordance with some embodiments of the present invention.

FIGS. 4A and 4B are schematic diagrams, or renderings, that provide various views of exemplary drainage component 400 that may be used with any of the surgical drains disclosed herein. In particular, FIG. 4A is a top view of fourth drainage component 400 and FIG. 4B provides a horizontal (as oriented in FIG. 4A) cross-section view of fourth drainage component 400 taken along bisecting line 4B-4B (shown in FIG. 4A).

Fourth drainage component 400 is a hollow tube that, in many cases, may have dimensions that are similar to first and/or second drainage component 100 and/or 200 and/or may be configured to function and/or be flexible and/or compliant in a manner similar to first and/or second drainage component 100 and/or 200. Fourth drainage component 400 includes a main body 410, a central lumen 430, a coupling 415, a coupling extension 420, a removable end cap 440, and a plurality oval-shaped drainage holes 405. Coupling 415 and/or coupling extension 420 may be sized, shaped, and/or configured to couple (usually permanently) to another component of a surgical drain as shown and described herein. Sets of drainage holes 405 are positioned on the top and bottom of fourth drainage component 400 as shown in FIG. 4B.

The surgical drains disclosed herein may include one or more positioning mechanisms that may be configured to assist a clinician with placement of a surgical drain within a hollow organ and/or tissue in a desired fashion and/or at a desired, or clinically relevant, location by providing tactile and/or visual feedback indicating the positioning mechanism and, therefore, an associated surgical drain is properly placed. The positioning mechanisms may include a circularly shaped shaft with a central open area configured for insertion of, and/or affixation to, another component (e.g., tube and/or drainage component) of the surgical drain and one or more extensions that extend from the shaft in a manner similar to a propeller. The extensions may be arranged, sized, and/or configured to assist with holding a surgical drain including an positioning mechanism in place. The extensions may be configured to articulate from an open to a closed arrangement when a force is exerted thereon as may be the case when the surgical drain is removed from the hollow organ and/or tissue via a natural and/or artificial orifice (e.g., surgical opening). This articulation may be achieved via a folding of one or more extensions at, or near, a joint (e.g., a hinge or living hinge) between the one or more extensions and the shaft.

Figure 5A:
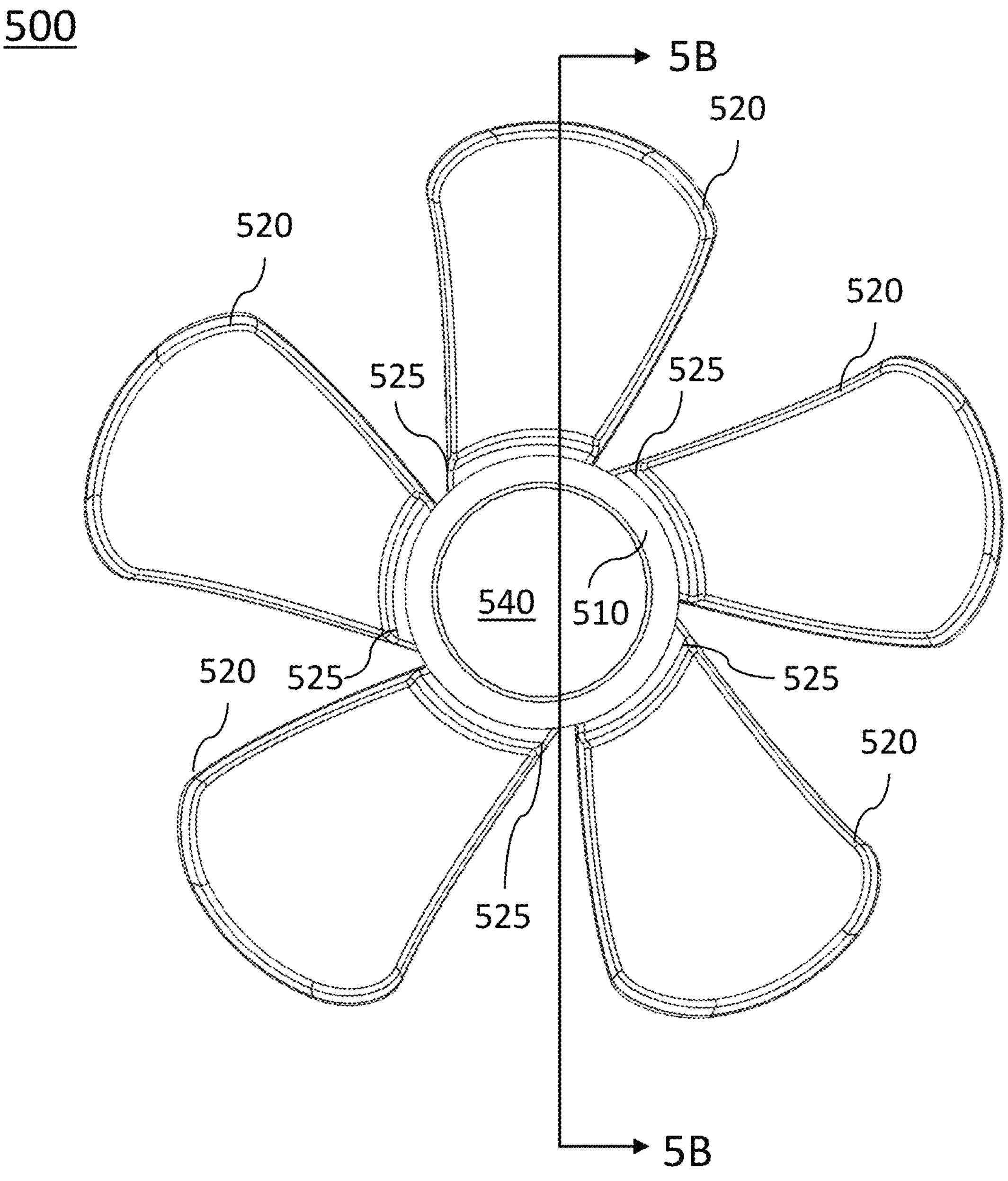
FIG. 5A is a schematic diagram of a front view of a first positioning mechanism in an unfolded, or open, configuration, in accordance with some embodiments of the present invention.
Figure 5B:
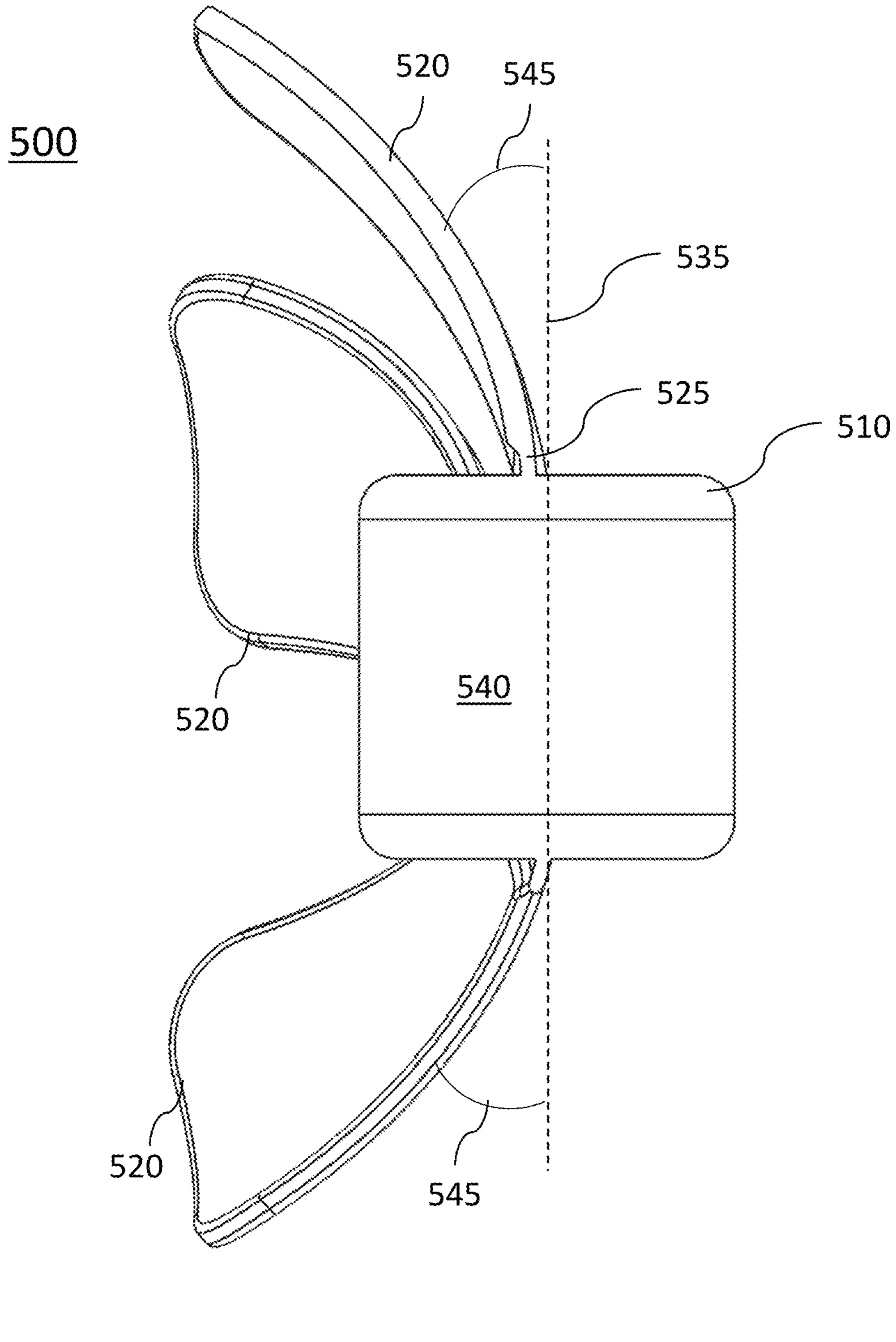
FIG. 5B is a schematic diagram of a cross-section view of the first positioning mechanism of FIG. 5A, in accordance with some embodiments of the present invention.
Figure 5C:
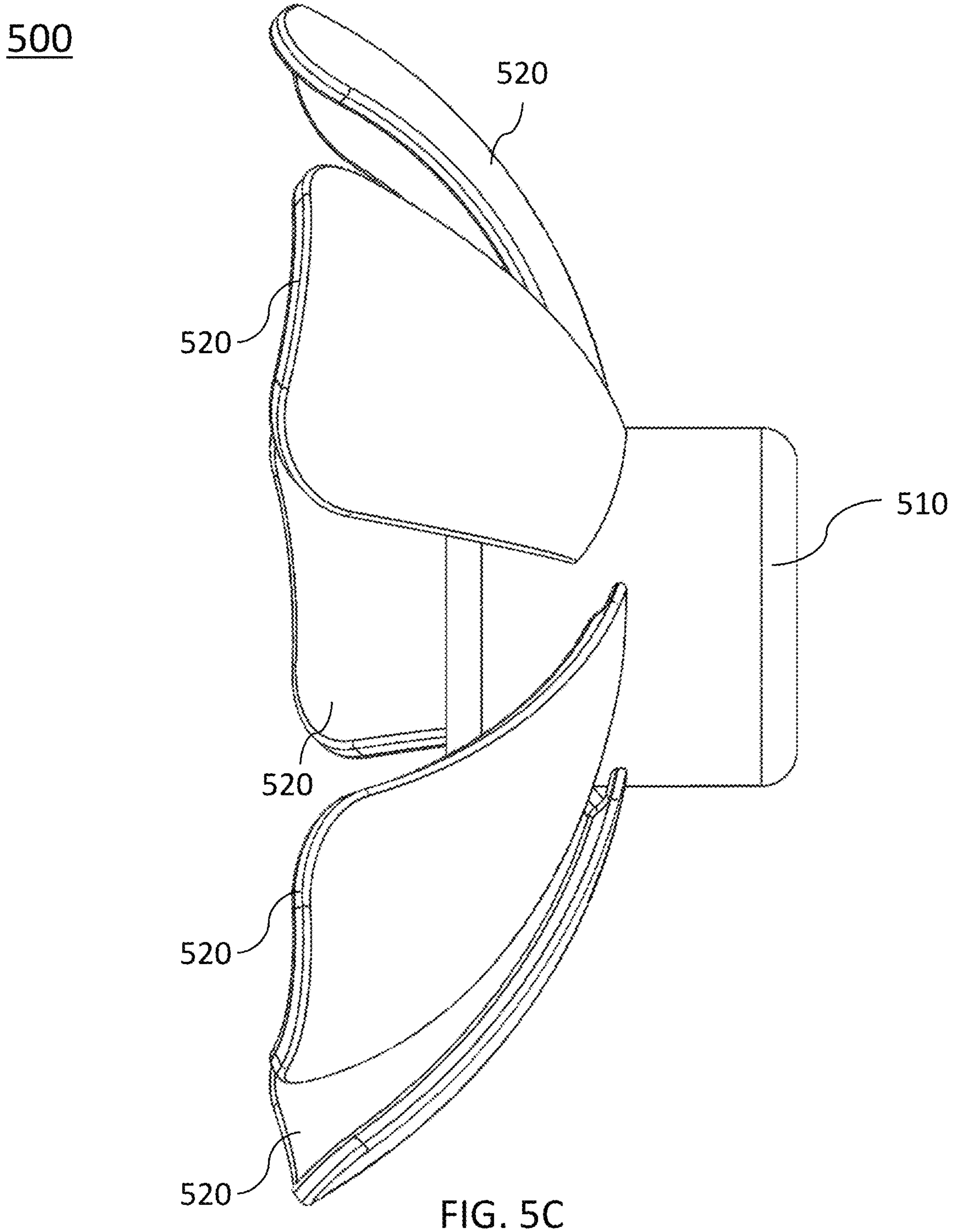
FIG. 5C is a schematic diagram of a side view of the first positioning mechanism of FIG. 5A, in accordance with some embodiments of the present invention.
Figure 5D:
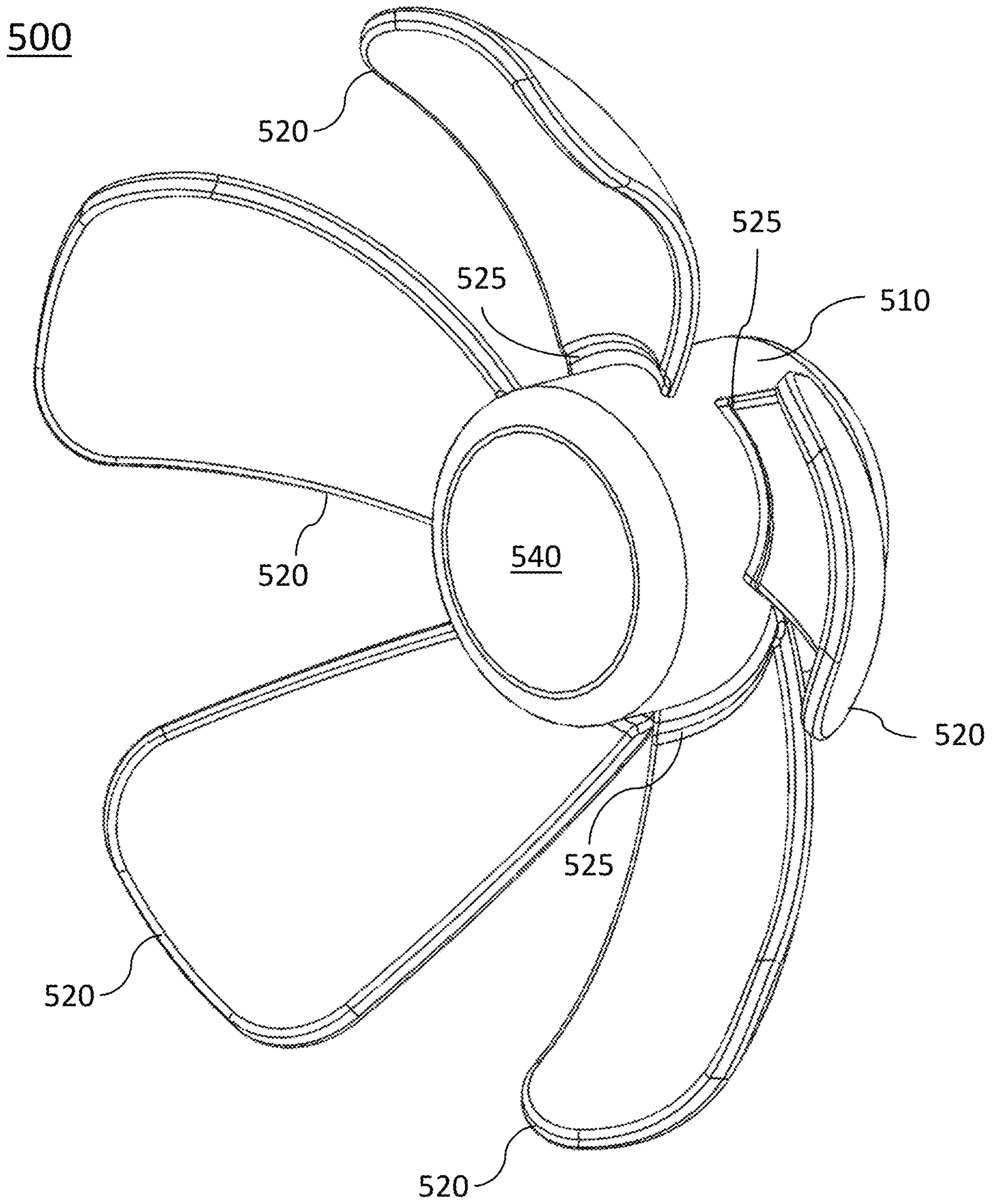
FIG. 5D is a schematic diagram of a perspective view of the first positioning mechanism of FIG. 5A, in accordance with some embodiments of the present invention.
Figure 5E:
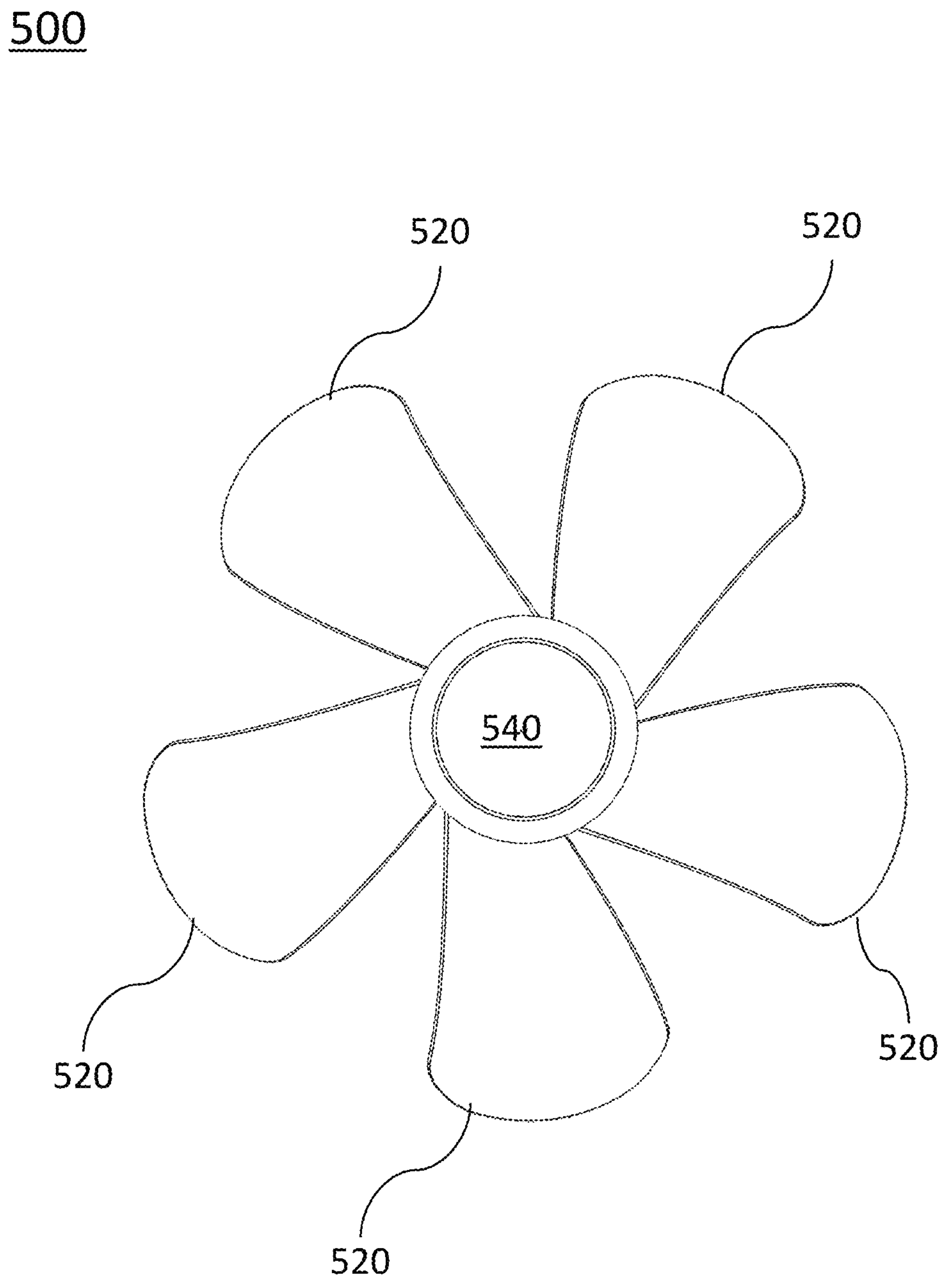
FIG. 5E is a schematic diagram of a back view of the first positioning mechanism of FIG. 5A, in accordance with some embodiments of the present invention.
Figure 5F:
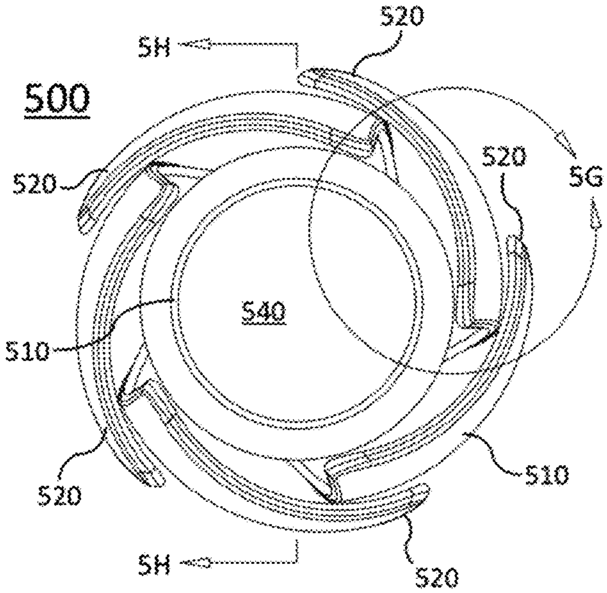
FIG. 5F is a schematic diagram of a front view of the first positioning mechanism of FIG. 5A in a folded, or closed, configuration, in accordance with some embodiments of the present invention.
Figure 5G:
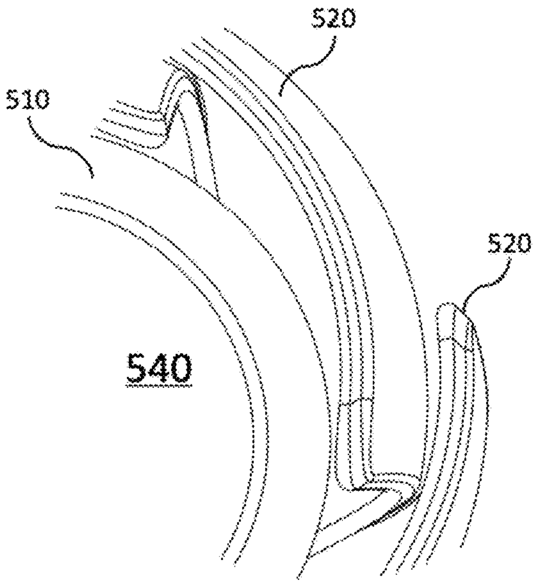
FIG. 5G is a schematic diagram of a detailed view of a portion of the first positioning mechanism of FIG. 5F, in accordance with some embodiments of the present invention.
Figure 5H:
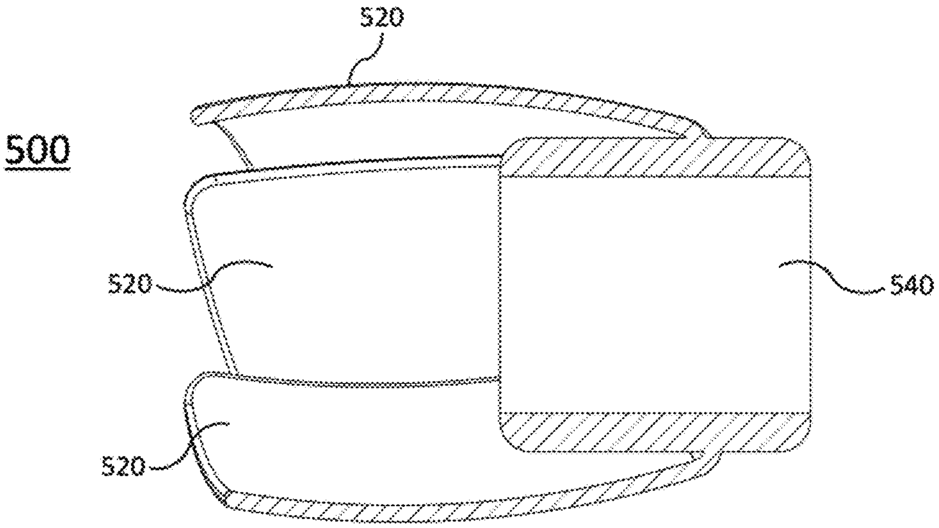
FIG. 5H is a schematic diagram of a cross-section view of the first positioning mechanism of FIG. 5F, in accordance with some embodiments of the present invention.
Figure 5I:
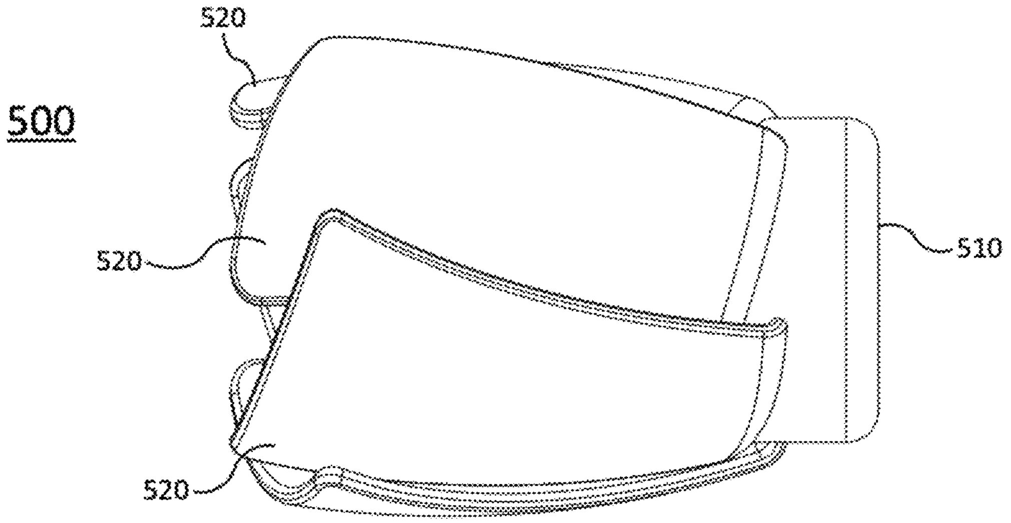
FIG. 5I is a schematic diagram of a side view of the first positioning mechanism of FIG. 5F, in accordance with some embodiments of the present invention.
Figure 5J:
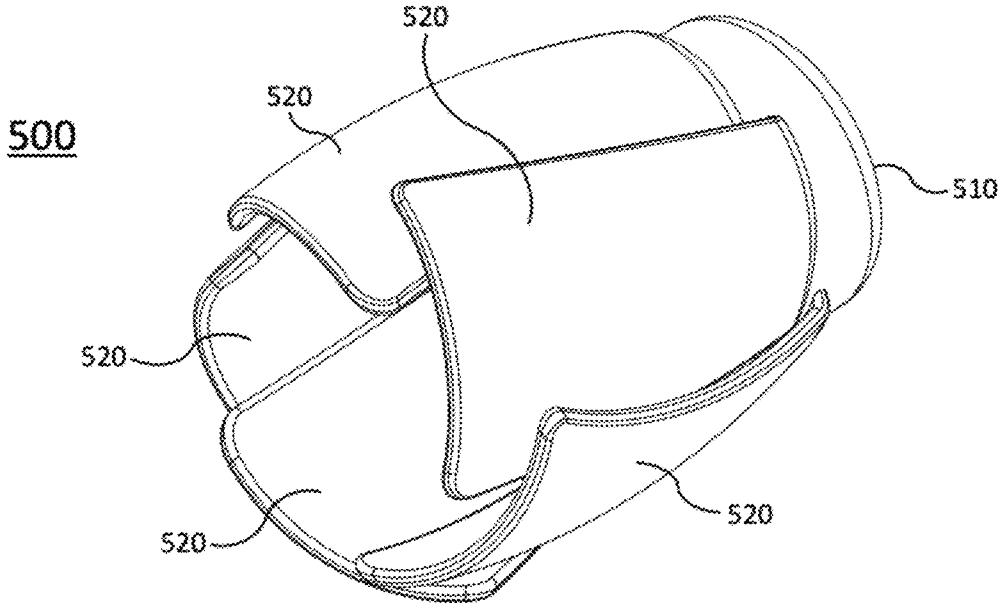
FIG. 5J is a schematic diagram of a perspective view of the first positioning mechanism of FIG. 5F, in accordance with some embodiments of the present invention.
Figure 7A:
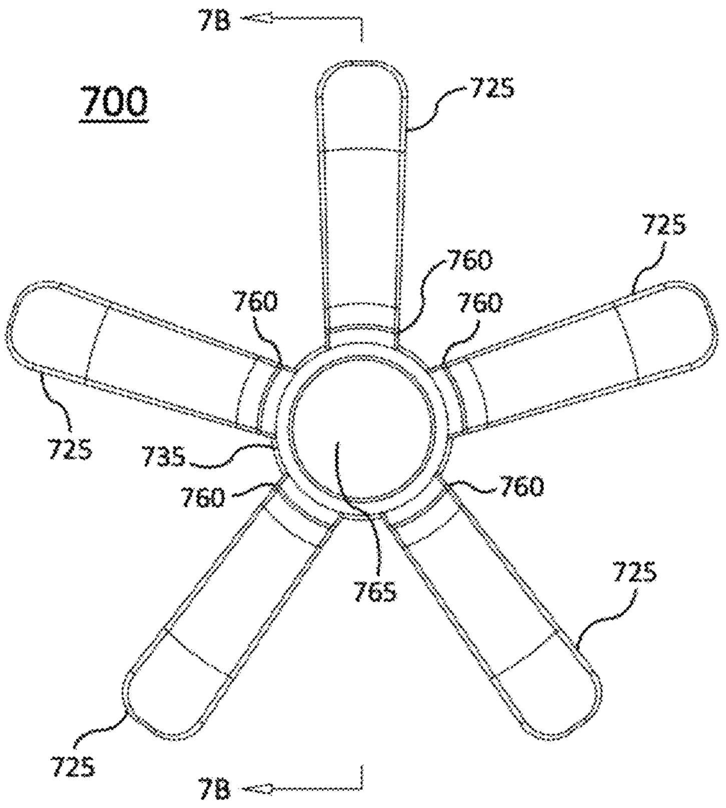
FIG. 7A is a schematic diagram of a front view of a third positioning mechanism in an open state, in accordance with some embodiments of the present invention.
Figure 7B:
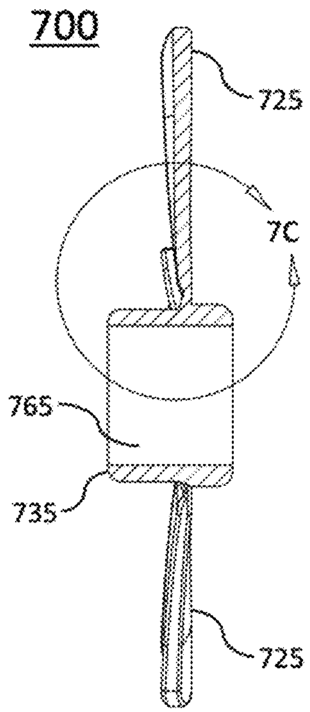
FIG. 7B is a schematic diagram of a cross-section view of the third positioning mechanism of FIG. 7A, in accordance with some embodiments of the present invention.
Figure 7C:
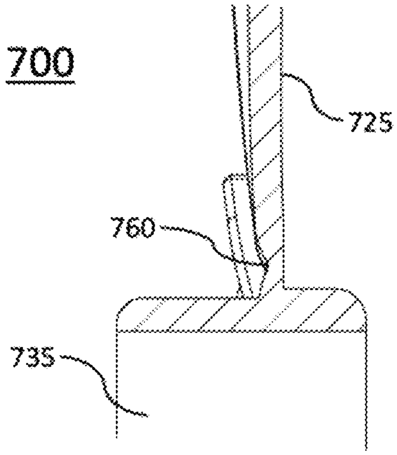
FIG. 7C is a schematic diagram of a detailed view of a portion of the third positioning mechanism of FIG. 7A, in accordance with some embodiments of the present invention.
Figure 7D:
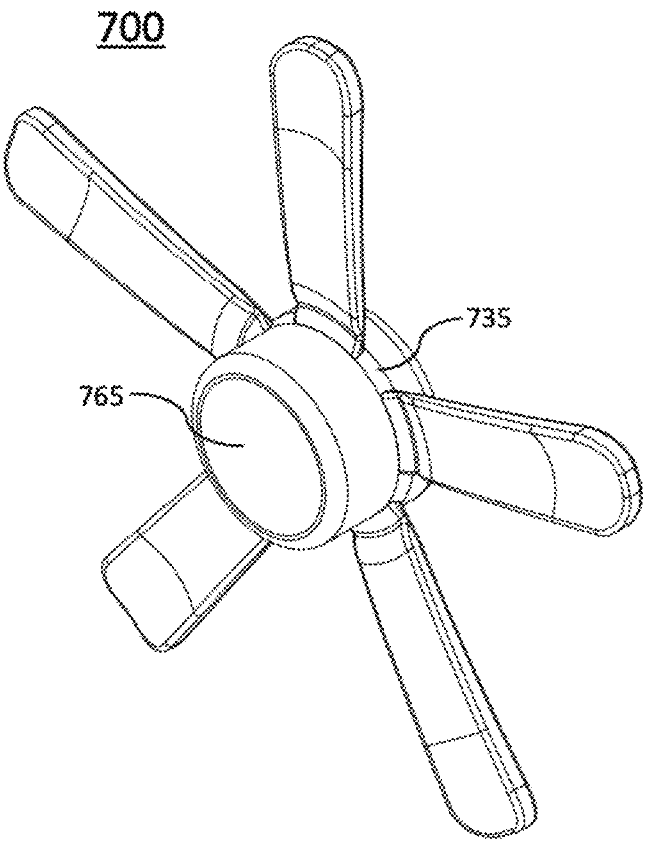
FIG. 7D is a schematic diagram of a top-perspective view of the third positioning mechanism of FIG. 7A, in accordance with some embodiments of the present invention.
Figure 7E:
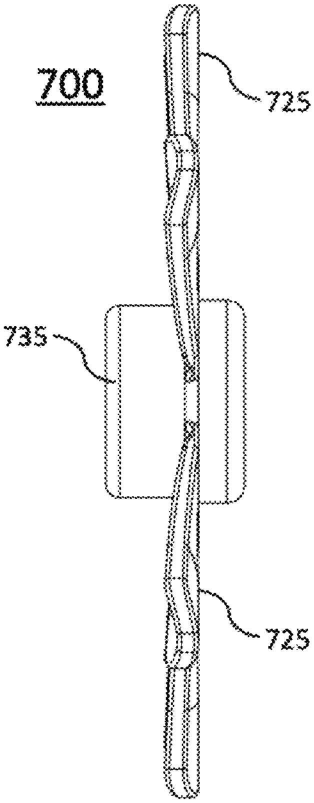
FIG. 7E is a schematic diagram of a side view of the third positioning mechanism of FIG. 7A, in accordance with some embodiments of the present invention.
Figure 8A:
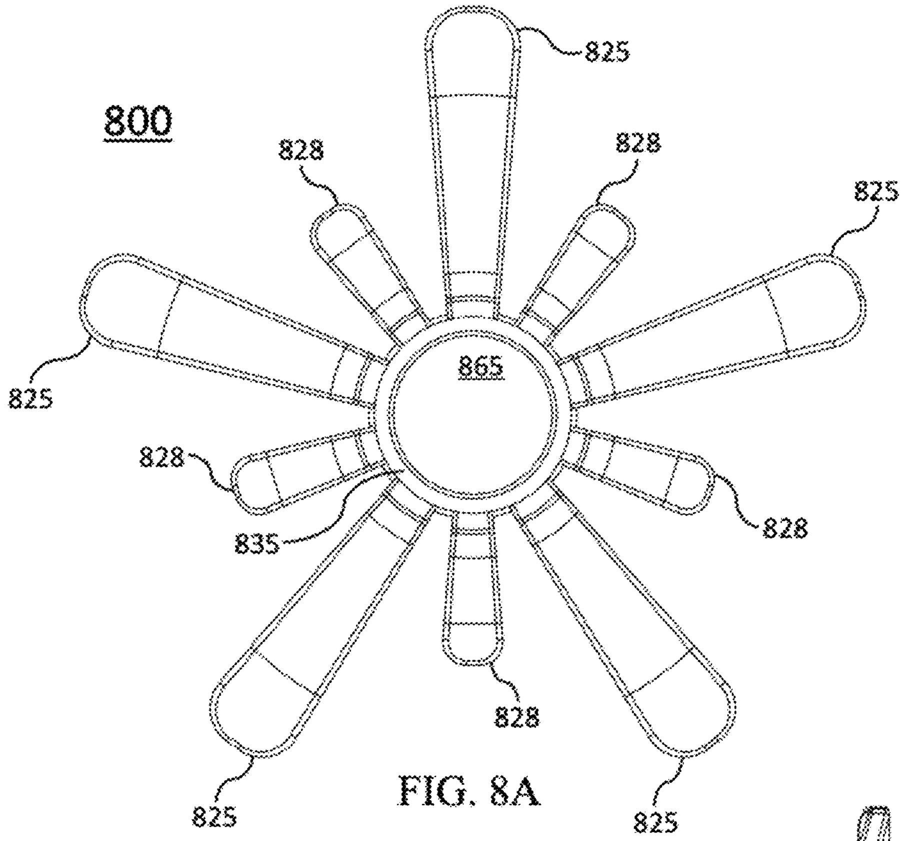
FIG. 8A is a schematic diagram of a top view of a fourth positioning mechanism, in accordance with some embodiments of the present invention.
Figure 8B:
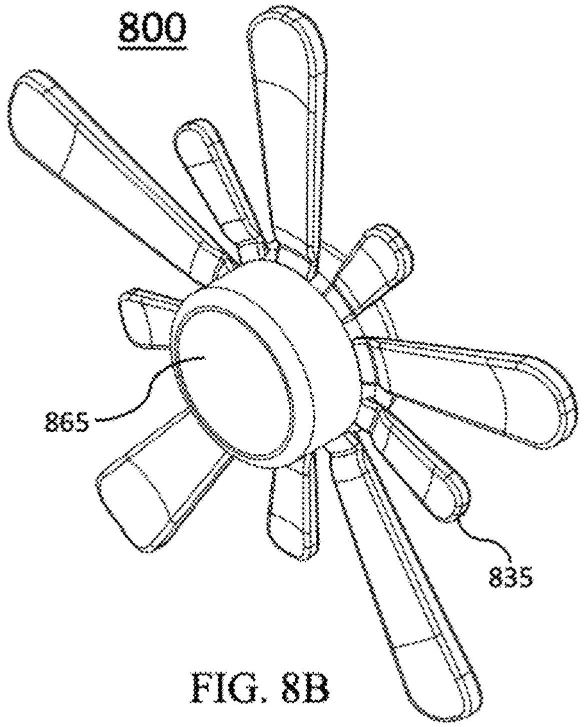
FIG. 8B is a schematic diagram of a top-perspective view of the fourth positioning mechanism of FIG. 8A, in accordance with some embodiments of the present invention.
Figure 8C:
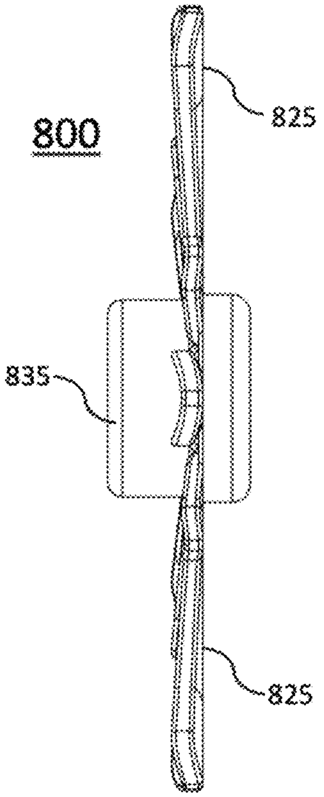
FIG. 8C is a schematic diagram of a side view of the fourth positioning mechanism of FIG. 8A, in accordance with some embodiments of the present invention.
Figure 9A:
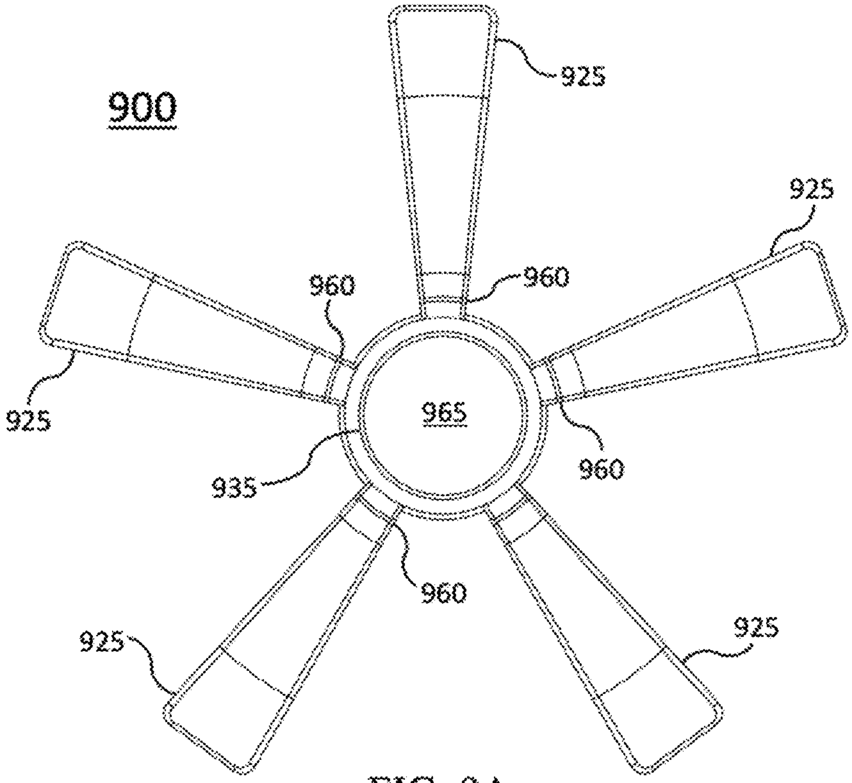
FIG. 9A is a schematic diagram of a top view of a fifth positioning mechanism, in accordance with some embodiments of the present invention.
Figure 9B:
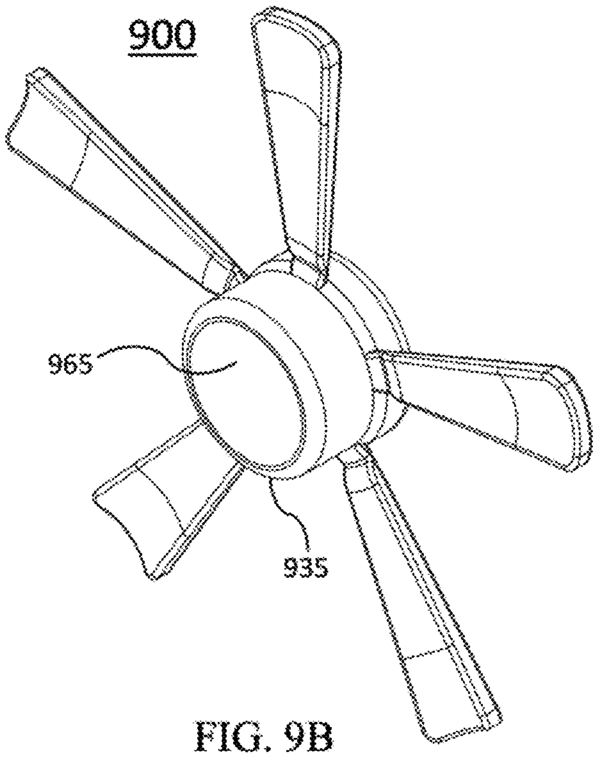
FIG. 9B is a schematic diagram of a top-perspective view of the fifth positioning mechanism of FIG. 9A, in accordance with some embodiments of the present invention.
Figure 9C:
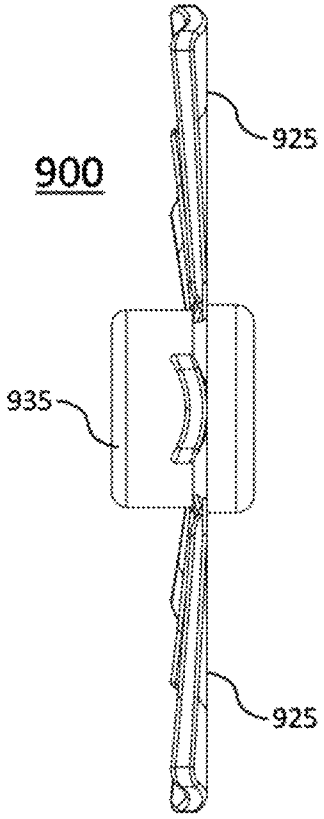
FIG. 9C is a schematic diagram of a side view of the fifth positioning mechanism of FIG. 9A, in accordance with some embodiments of the present invention.

FIGS. 5A-9C provide renderings and/or schematic diagrams of various views of different exemplary positioning mechanisms that may be used with surgical drains such as the surgical drains shown and described herein, wherein FIGS. 5A-5J provide various views of a first positioning mechanism 500; FIGS. 6A-6D provide various views of a second positioning mechanism 600; FIGS. 7A-7E provide various views of a third positioning mechanism 700; FIGS. 8A-8C provide various views of a fourth positioning mechanism 800; and FIGS. 9A-9C provide various views of a fifth positioning mechanism 900. In particular, FIG. 5A is a front view of positioning mechanism 500 in an unfolded, or open, configuration; FIG. 5B provides a cross-section view of positioning mechanism 500 in the unfolded configuration along line 5B-5B, provided by FIG. 5A; FIG. 5C is a side view of positioning mechanism 500 in the unfolded configuration; FIG. 5D is a perspective view of positioning mechanism 500 in the unfolded configuration; FIG. 5E is a back view of positioning mechanism 500 in the unfolded configuration; FIG. 5F is a front view of positioning mechanism 500 in a folded, or closed, configuration; FIG. 5G is a detailed view of region B (shown in FIG. 5F) of positioning mechanism 500 in the folded configuration; FIG. 5H is a cross-section view of positioning mechanism 500 in the folded configuration taken along bisecting line 5H-5H, which is provided by FIG. 5F; FIG. 5I is a side view of positioning mechanism 500 in the folded configuration; and FIG. 5J is a perspective view of first positioning mechanism 500 in the folded configuration.

Figure 10B:
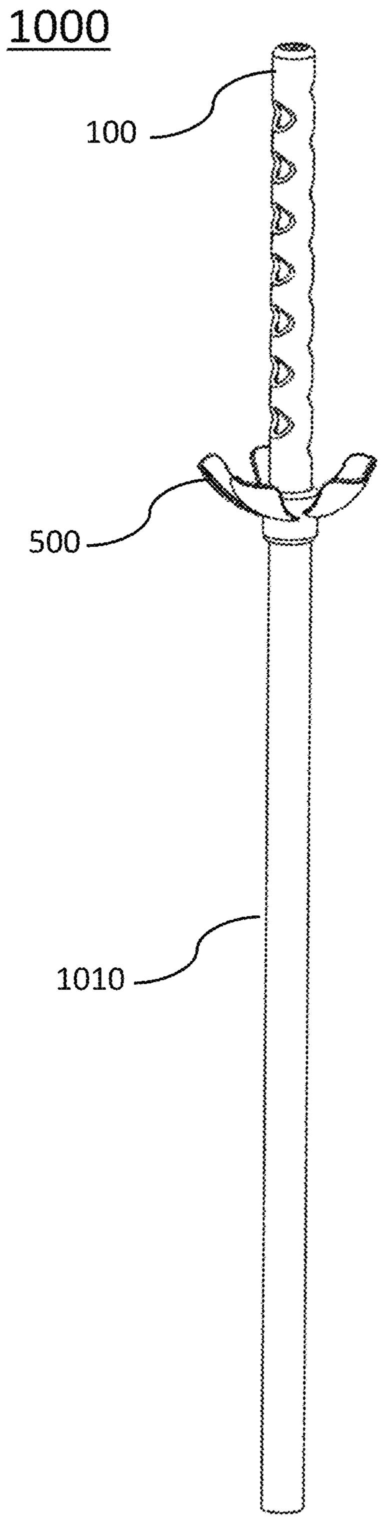
FIG. 10B is a schematic diagram of an assembled first exemplary surgical drain, in accordance with some embodiments of the present invention.

First positioning mechanism 500 includes a circular shaft 510 that encircles an opening 540 sized, arranged, and configured for cooperation with another component (e.g., a tube or drainage component) of a surgical drain as shown and described herein (see e.g., FIGS. 10A1 and 10B. First positioning mechanism 500 further includes a plurality (in this case, five) of extensions 520 that extend radially outward from shaft 510 and curve in a manner that is oriented at an angle 545 (e.g., 10-40 degrees) relative to shaft 510 as shown in, for example, FIG. 5B which has a reference line 535, which is not part of first positioning mechanism 500, that is perpendicular to shaft 510 superimposed thereon. Each of five extensions 520 may have a curvature with a radius between 0.5-4 inches. Five extensions 520 extend from shaft 510 as shown and are configured to articulate between and unfolded configuration (see e.g., FIGS. 5A-5E) and a folded configuration (see e.g., FIGS. 5F-5J) by folding toward the shaft 510 and opening 540 at a joint between shaft 510 and each extension 520. At the joint, the base of each extension 520 may be oriented at a non-perpendicular angle (as may be seen in, for example, FIG. 5C) relative to shaft 510, which may encourage uniform folding of extensions 520 as they transition from the open to closed state and vice versa.

The embodiment of first positioning mechanism 500 also includes an optional hinge 525 positioned the joint between shaft 510 and each extension 520. Each hinge 525 may be configured to facilitate the folding of a corresponding extension 520 at the joint/hinge 525 in a relatively smooth shape without bunching or twisting and minimize a profile of the collapsed assembly that may, in some instances, facilitate atraumatic extraction of first positioning mechanism 500 and/or a surgical drain that includes first positioning mechanism 500 from a hollow organ and/or tissue. Without hinges 525, extensions 520 may not fold as flat, which may result in a larger overall diameter at, for example, a junction between the extensions 520 and shaft 510. As may be seen in the cross-section view of FIG. 5B, hinge 525 may be embodied as a notch, or relatively thin region of an extension 520 positioned at a joint between the extension 520 and shaft 510. At times, hinge 525 may be configured to enable an inflection point for extension 520 so that it may articulate at hinge 525 without deforming a shape or size of extension 520. In some embodiments, hinge 525 may be a living hinge. Additionally, or alternatively, the hinge 525 and/or extensions 520 may be configured to have a shape memory so that extension 520 returns to an original, or preferred, orientation and/or shape following deformation and/or folding during, for example, insertion into and/or removal from the hollow organ and/or tissue.

A shape of each extension 520 is tapered along their length so that, when folded, a portion of a first extension 520 covers a portion of a second, adjacent, extension 520 as shown in, for example, FIGS. 5E-5I. In addition, a horizontal cross-sectional shape of extensions 520 is curved with, for example, a concave curvature configured to, for example, match or correspond to a tube diameter so that, for example, the extensions may fold in closely to the tube, thereby reducing an overall cross-sectional area of first positioning mechanism 500 so that it may be atraumatically extracted from a hollow organ and/or tissue. As may be seen in, for example, FIGS. 5C, 5D, and 5F-5J, each extension 520 may be curved along its width with, for example, a concave curvature so that, when folded (as shown in FIGS. 5F-5J), the plurality of extensions 520 may form a cylindrical shape that may, for example, fit over a component (e.g., a tube or drainage component of a surgical drain) attached to shaft 510 with a minimized external diameter and/or profile.

Figure 6A:
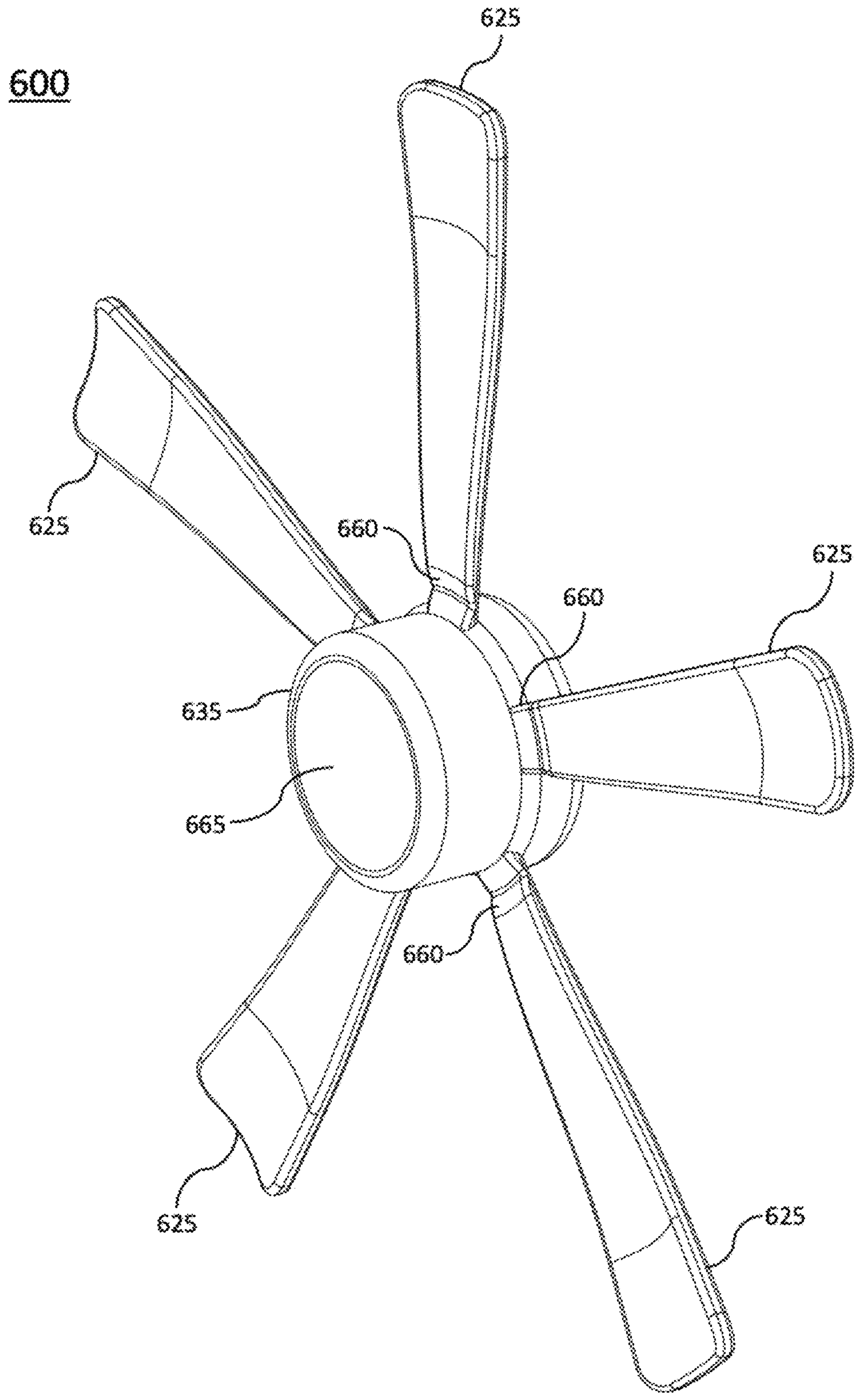
FIG. 6A is a schematic diagram of a side-perspective view of a second exemplary positioning mechanism for use with a surgical drain in an open state, in accordance with some embodiments of the present invention.
Figure 6B:
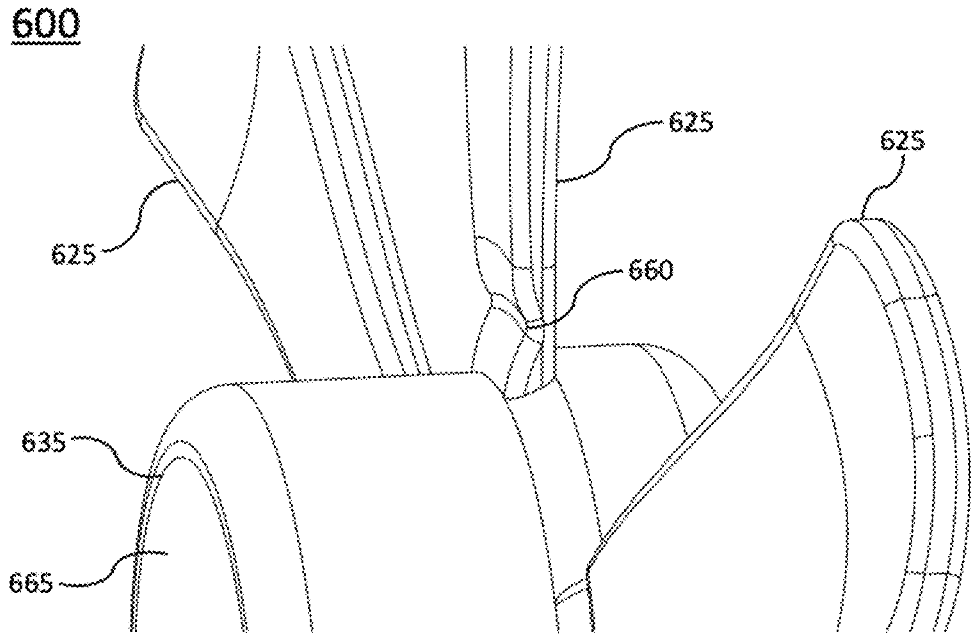
FIG. 6B is a schematic diagram of a close-up view of a portion of the second positioning mechanism in the open state, in accordance with some embodiments of the present invention.
Figure 6C:
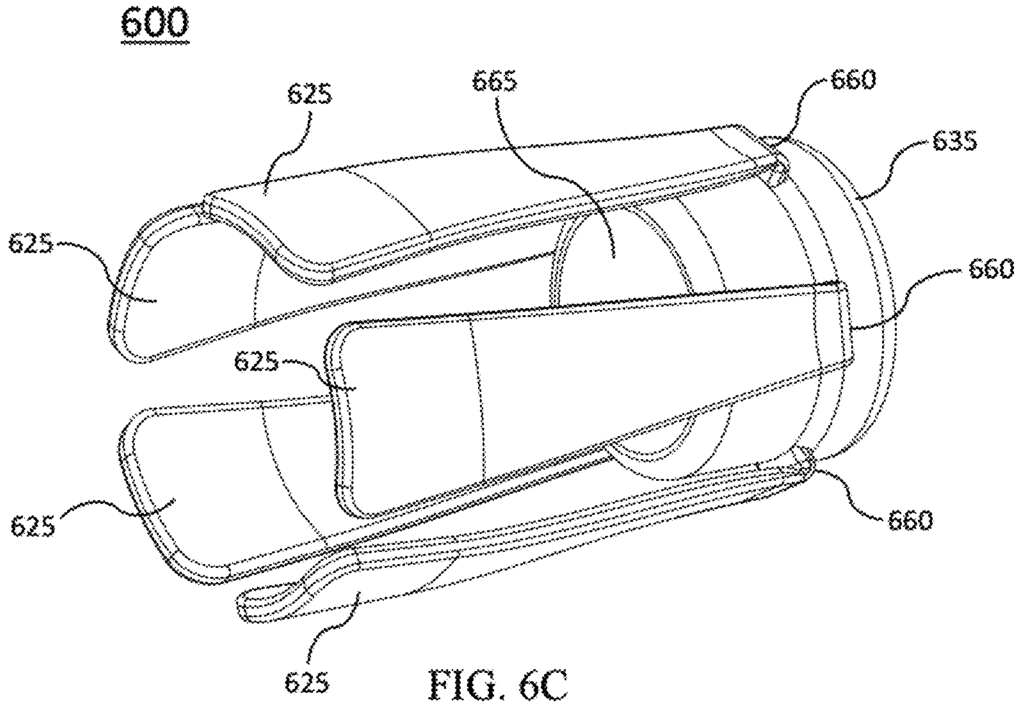
FIG. 6C is a schematic diagram of a front-perspective view of the second positioning mechanism in a closed state, in accordance with some embodiments of the present invention.
Figure 6D:
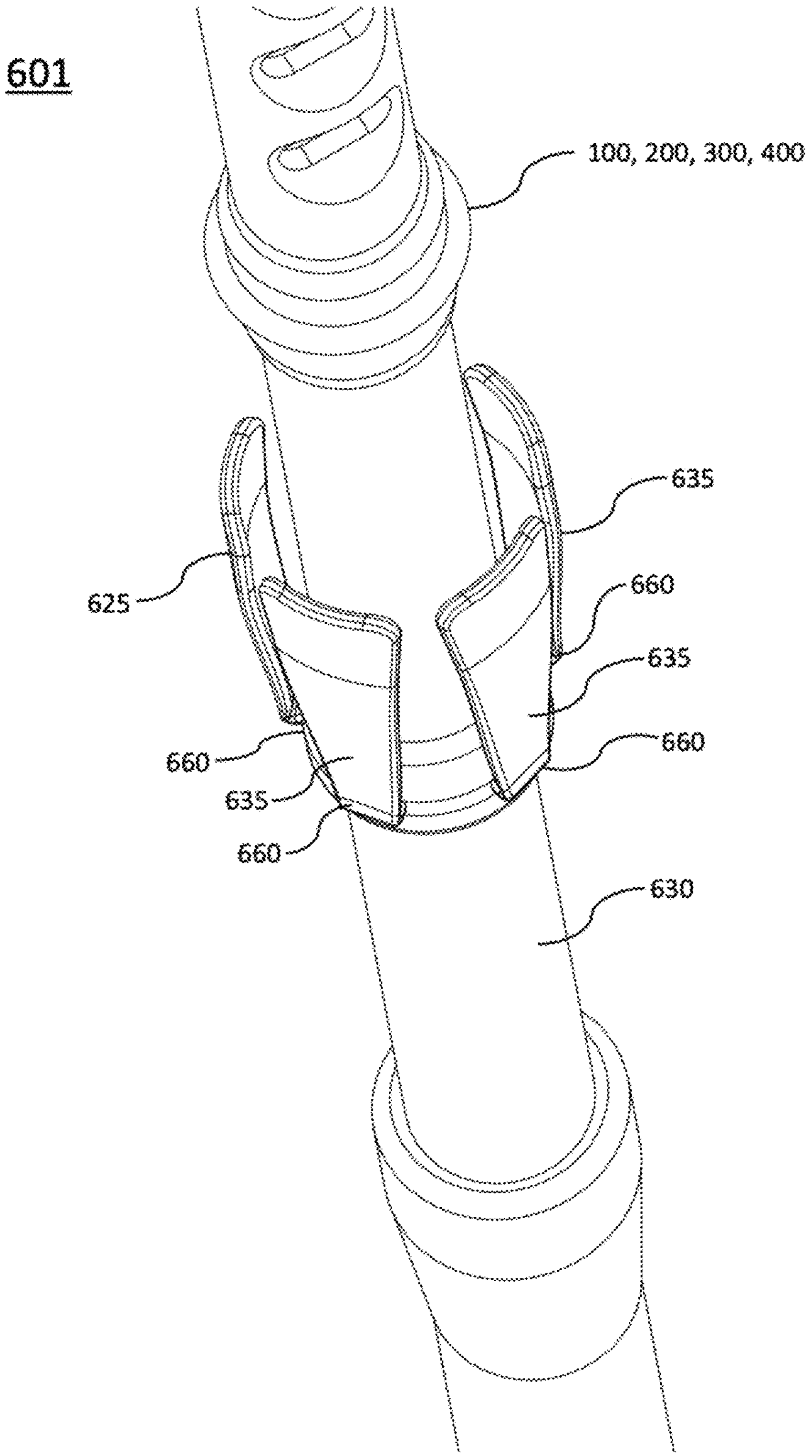
FIG. 6D is a schematic diagram of a side-perspective view of the second positioning mechanism positioned on an exemplary surgical drain in a closed state, in accordance with some embodiments of the present invention.

FIGS. 6A-6D provide various views of second exemplary positioning mechanism 600 for use with a surgical drain. In particular, FIG. 6A provides a schematic diagram of a side-perspective view of second exemplary positioning mechanism 600 for use with a surgical drain in an open state; FIG. 6B provides a schematic diagram of a close-up view of a portion of second positioning mechanism 600 in the open state; FIG. 6C provides a schematic diagram of a front-perspective view of second positioning mechanism 600 in a closed state; and FIG. 6D provides a schematic diagram of a side-perspective view of second positioning mechanism 600 positioned on an exemplary surgical drain in a closed state.

Second positioning mechanism 600 may be configured to function and/or transition from an open state to a closed state in a manner similar to first positioning mechanism 500. Positioning mechanism 600 includes a shaft 635 and five extensions 625 that extend radially out from shaft 610. Shaft 635 may be sized, shaped, and/or configured to define an exterior diameter of an opening 665 as shown in, for example, FIGS. 6A-6C. Opening 665 may be sized, shaped, and/or configured to fit over and/or encircle an outer diameter of one or more components of a surgical drain such as a tube like tube 630 (shown in FIG. 6D) and/or a drainage component like drainage components 100, 200, 300, or 400 that may reside within and/or be affixed to opening 665 for an assembled surgical drain.

Each of extensions 625 are of similar shape and size to one another and have a tapered shape with a minimum width proximate to shaft 635 that gradually expands along its length to a maximum width at an end of each extension 635 positioned furthest away from shaft 635. A smaller width of extension 625 proximate to shaft 635 may allow for easier articulation of extensions 625 when transitioning from an open (see e.g., FIG. 6A) to a closed (see e.g., FIGS. 6C and 6D) configuration when compared with an extension of uniform width because less material has to bend at the narrower, articulating, portion of each extension 625. Additionally, or alternatively, a shape of extensions 625 may achieve easier folding while still being sufficiently visible and/or provide sufficient tactile feedback to a clinician placing a surgical drain within a hollow organ and/or tissue than, for example, an extension that was uniformly narrow along its length.

Each extension 625 is coupled to shaft 635 via a hinge 660 configured to enable folding of each respective extension 635 as it transitions from an open state (shown in FIGS. 6A and 6B) to a closed state (shown in FIGS. 6C and 6D). Hinge 660 may be, for example, a portion of extension 625 that is thinner that a remaining portion of extension 625 (see e.g., FIG. 6B) and/or a component that enables an inflection point for extension 625 so that it may articulate at hinge 660 without deforming a shape or size of extension 625. In some embodiments, hinge 660 may be a living hinge and/or a shape memory material.

Each extension 625 has a curved shape (e.g., a concave curvature) across its width that may be shaped and/or configured to, for example, match or correspond to shape and/or size of shaft 635 and/or another component of an assembled surgical drain, such as a tube 630 of an assembled surgical drain 601 as shown in FIG. 6D, when in a closed shape and reduce an overall cross-sectional area of second positioning mechanism 600 and/or a surgical drain that includes second positioning mechanism 600. As may be seen in FIGS. 6C and 6D, extensions 625 do not overlap with one another when in a closed, or folded, arrangement, which may serve to, for example, provide an positioning mechanism with a sleek profile and no edges extending therefrom when in a closed state, which may enable atraumatic extraction of a surgical drain that includes second positioning mechanism 600 from a hollow organ and/or tissue.

FIGS. 7A-7E provide various views of third exemplary positioning mechanism 700 and, in particular, FIG. 7A provides a front view of a third positioning mechanism 700 in an open state; FIG. 7B. provides a cross-section view of third positioning mechanism 700 in the open state along bisecting line 7B-7B, which is provided in FIG. 7A; FIG. 7C provides a detailed view of a portion of third positioning mechanism 700 shown in cut-out B of FIG. 7B; FIG. 7D provides a top-perspective view of third positioning mechanism 700; and FIG. 7E provides a side view of third positioning mechanism 700. Third positioning mechanism 700 includes a shaft 735 sized and configured to encircle an opening 765 in a manner similar to shaft 510 and/or 635. Third positioning mechanism 700 further includes five extensions 725 that have a regular, or substantially constant, shape and width along their length and are positioned and configured to extend radially outward from shaft 735. Each extension 725 is coupled to and/or extends from shaft 735 via a hinge 760 configured to enable folding of each respective extension 735 as it transitions from an open state to a closed, or folded, state as, for example, described herein. In some embodiments, extensions 725 may not touch and/or overlap with one another when in a closed, or folded, state.

As may be seen in, for example, the cross-section of FIG. 7B and/or the detail view of FIG. 7C, hinge 760 may be configured as a notch in a portion of an extension 725 positioned near shaft 735 and may be configured and/or shaped to allow for the bending, or folding, of extension 725 at hinge 760 so that an extension 725 may articulate at hinge 760 from an open to a closed arrangement without deforming a shape or size of extension 725. Extension 725 have an approximately flat horizontal (i.e., in a plane perpendicular to shaft 735) cross-section shape (as may be seen in FIGS. 7B, 7C, and 7E) that enables extensions 725 to fold up against a component of a surgical drain (e.g., a tube like tube 630 and/or a drainage component like drainage component 100, 200, 300, or 400) when in a closed arrangement and reduce an overall cross-sectional area of third positioning mechanism 700 and/or a surgical drain that includes third positioning mechanism 700, thereby providing a minimized and/or sleek profile with no edges extending therefrom when in a closed state, which may enable atraumatic extraction of a surgical drain that includes third positioning mechanism 700 from a hollow organ and/or tissue via an orifice therein.

FIGS. 8A-8C provide various views of fourth exemplary positioning mechanism 800 for use with a surgical drain, wherein FIG. 8A provides a top view, FIG. 8B provides a top-perspective view, and FIG. 8C provides a side view of fourth positioning mechanism 800. Fourth positioning mechanism 800 is similar to third positioning mechanism 700 in that it includes five large extensions 825 joined to a shaft 835 that encircles and/or defines a circular opening 865 sized, shaped, and configured to accept insertion of a or a component of a surgical drain (not shown). However, unlike third positioning mechanism 700, fourth positioning mechanism 800 includes five additional small extensions 828 positioned between each of the five large extensions 825 in an alternating pattern. Both large and small extensions 825 and 828 are attached to shaft 835 and are configured to articulate at, or near, this attachment point to fold toward shaft 835 and/or a component of a surgical drain (not shown) in which fourth positioning mechanism 800 may reside when positioned within opening 865. In some embodiments, the articulation of large and/or small extensions 825 and/or 827 may be facilitated by a hinge like hinge 525, 660, and/or 760.

FIGS. 9A-9C provide various views of fifth exemplary positioning mechanism 900 for use with a surgical drain as disclosed herein, wherein FIG. 9A provides a top view, FIG. 9B provides a top-perspective view, and FIG. 9C provides a side view of fifth positioning mechanism 900. Fifth positioning mechanism 900 includes five large extensions 925 that are relatively narrower than, for example, extensions 725 or 825. Extensions 925 are attached to a shaft 935 and are configured to articulate at, or near, this attachment point to fold toward shaft 935 in a manner similar to that described herein with regard to positioning mechanisms 500, 600, 700, and/or 800. In some embodiments, the articulation of large and/or small extensions 925 and/or 927 may be facilitated by a hinge like hinge 525, 660, and/or 760.

In most embodiments, the drainage components and positioning mechanisms disclosed herein may be fabricated from a material that is capable of flexibility and/or deformability such silicon or plastic. In some cases, they may be two separate components that are assembled together to make a surgical drain as disclosed herein and, in other embodiments, they may be fabricated together as a single piece. In some embodiments, extensions 520, 625, 725, 825, and 925 may be sized, shaped, arranged, and/or configured to, for example, provide tactile feedback to a clinician inserting a surgical drain including an positioning mechanism like positioning mechanism 500, 600, 700, 800, or 900 into a hollow organ and/or tissue because it may be configured to prevent further advancement of the respective positioning mechanism and/or surgical drain through a orifice in the hollow organ and/or tissue. Additionally, or alternatively, extensions 520, 625, 725, 825, and 925 may be configured to prevent movement of the surgical drain or a drainage component during use within a hollow organ and/or tissue by, for example, providing a stable base for a drainage component like drainage component 100, 200, 300, or 400 when it extends into a cavity of hollow organ and/or tissue during use and/or is positioned against tissue surrounding a surgical incision. For example, when the surgical drains disclosed herein are placed within abdominal tissue (e.g., intestine or perineum), extensions 520, 625, 725, 825, and 925 may be configured to be positioned on an internal abdominal wall (e.g., on the internal side of the rectus muscle) to provide a block, or stop, against accidental or unintentional movement and/or expulsion of the surgical drain from the surgical opening due to, for example, intra-abdominal movement and/or patient movement (e.g., coughing, twisting, or transitioning from sitting to standing). In another example, when the surgical drains disclosed herein are placed within thoracic or lung tissue, extensions 520, 625, 725, 825, and 925 may be configured to be positioned on an internal side of muscular (e.g., pectorals) tissue to provide a block, or stop, against accidental or unintentional movement and/or expulsion of the surgical drain from the surgical opening due to, for example, patient movement (e.g., coughing, twisting, or transitioning from sitting to standing).

Figure 10C:
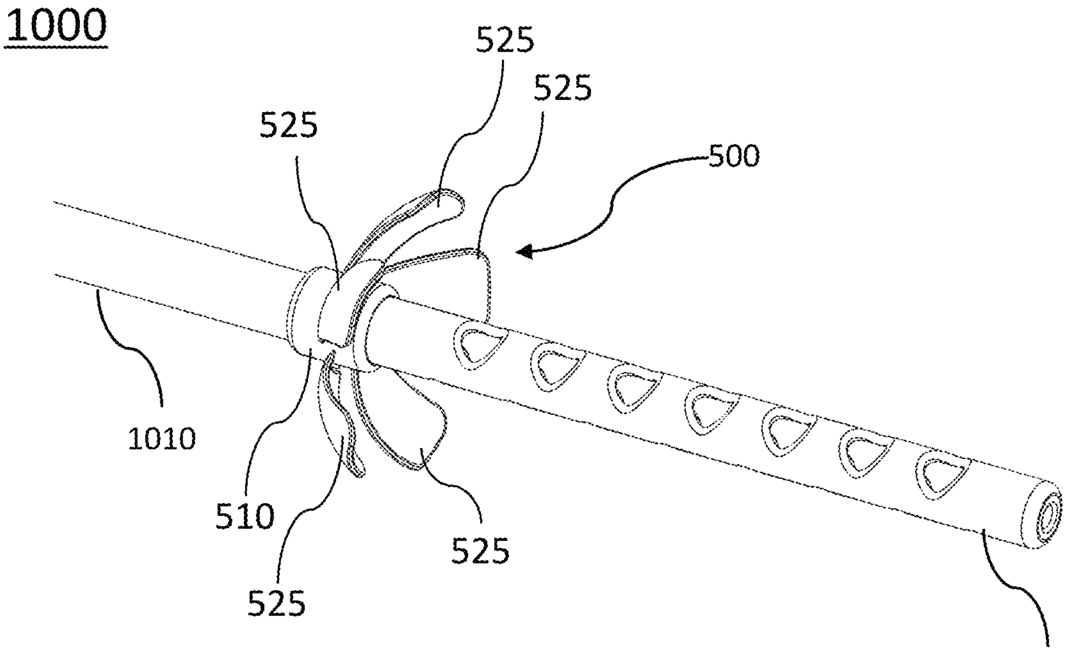
FIG. 10C is a schematic diagram of a first close up view of a portion of the assembled first exemplary surgical drain of FIG. 10B with first positioning mechanism in an open configuration, in accordance with some embodiments of the present invention.
Figure 10D:
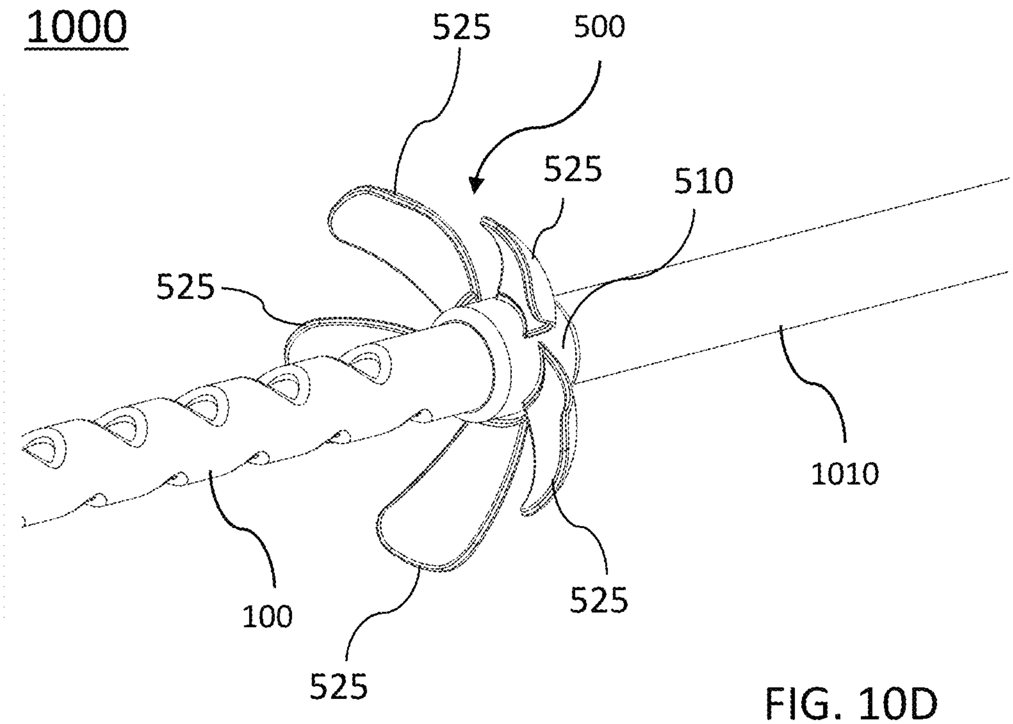
FIG. 10D is a schematic diagram of a second close up view of a portion of the assembled first exemplary surgical drain of FIG. 10B with first positioning mechanism in an open configuration, in accordance with some embodiments of the present invention.

A surgical drain as described herein may comprise a drainage component like drainage component 100, 200, 300, and/or 400, an positioning mechanism like positioning mechanism 500, 600, 700, 800, and/or 900, and a tube. An exploded view of an exemplary surgical drain 1000 that includes a drainage component like drainage component 100, an positioning mechanism like positioning mechanism 500 in an unfolded configuration, and a tube 1010 is provided by FIG. 10A1, which shows how positioning mechanism 500 may be aligned with, and positioned between, drainage component 100 and tube 1010. FIG. 10A2 provides a cross-section view of tube 1010 at bisecting line 10A2-10A2 and shows a sidewall of tube 1010 and a central lumen 1020 that runs along the length of tube 1010. FIG. 10B is a schematic diagram that provides an assembled view of surgical drain 1000 showing how drainage component 100, positioning mechanism 500, and tube 1010 are assembled and affixed (via, for example, heat, vibrational, and/or chemical bonding) together. In most embodiments, drainage component 100, positioning mechanism 500, and tube 1010 are permanently affixed together prior to use. FIGS. 10C and 10D each provide a close up perspective view of positioning mechanism 500 in an open arrangement that illustrates inter alia how shaft 510 fits over a joint or coupling between drainage component 100 and tube 1010 and extensions 520 curve toward drainage component 100 when positioning mechanism is in an unfolded configuration.

Figure 10E:
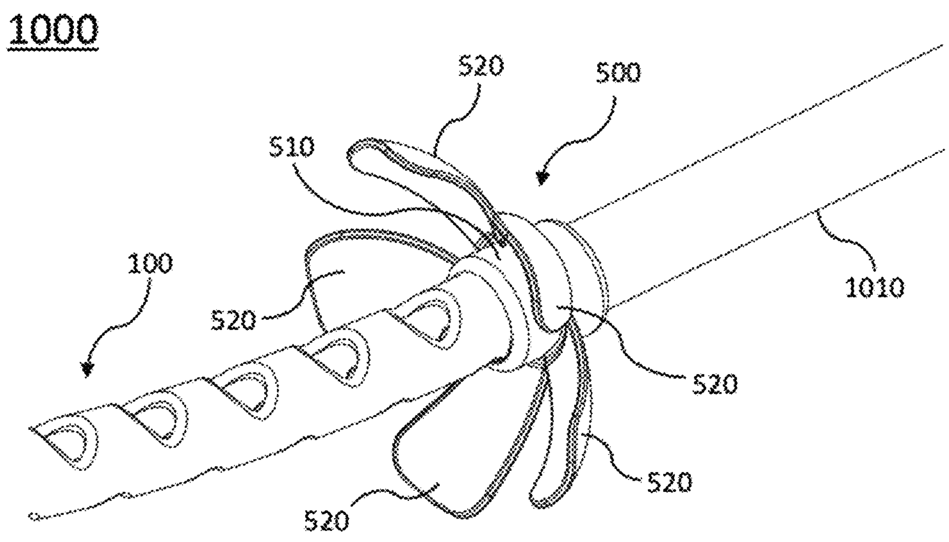
FIG. 10E is a schematic diagram of a third close up view of a portion of the assembled first exemplary surgical drain of FIG. 10B with first positioning mechanism in a partially folded configuration, in accordance with some embodiments of the present invention.
Figure 10F:
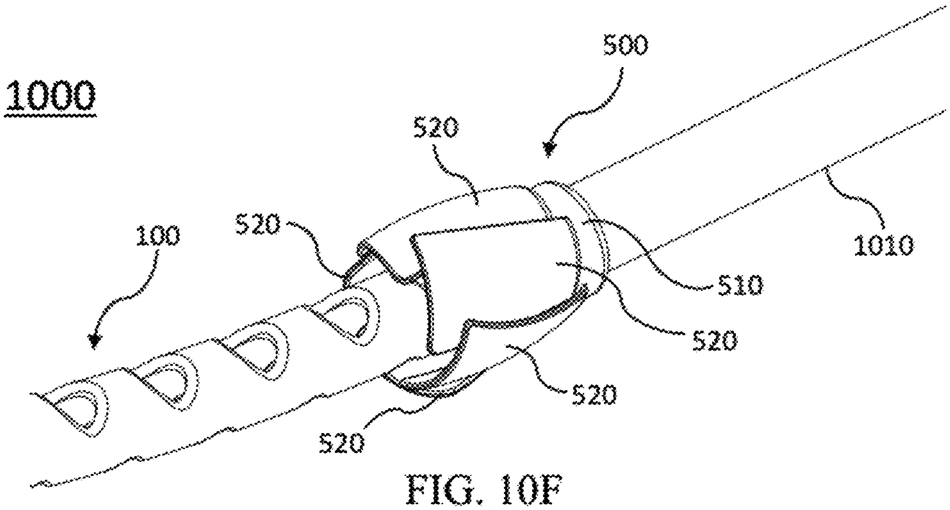
FIG. 10F is a schematic diagram of a fourth close up view of a portion of the assembled first exemplary surgical drain of FIG. 10B with first positioning mechanism in a folded configuration, in accordance with some embodiments of the present invention.

FIGS. 10E and 10F provide close up perspective views of positioning mechanism 500 of tube 1010 as it transitions from an unfolded configuration as shown in FIGS. 10A1-10D to a folded configuration. In particular, FIG. 10E shows positioning mechanism 500 in transition between the unfolded configuration to the folded configuration of FIG. 10F, wherein each extension 520 is partially folded at hinge 525 toward drainage component 100 and FIG. 10F shows a fully folded configuration of positioning mechanism 500, wherein each extension 520 is fully folded at hinge 525 and positioned proximate to drainage component 100 in a manner similar to that shown in FIGS. 5F-5J and discussed herein.

Figure 11A:
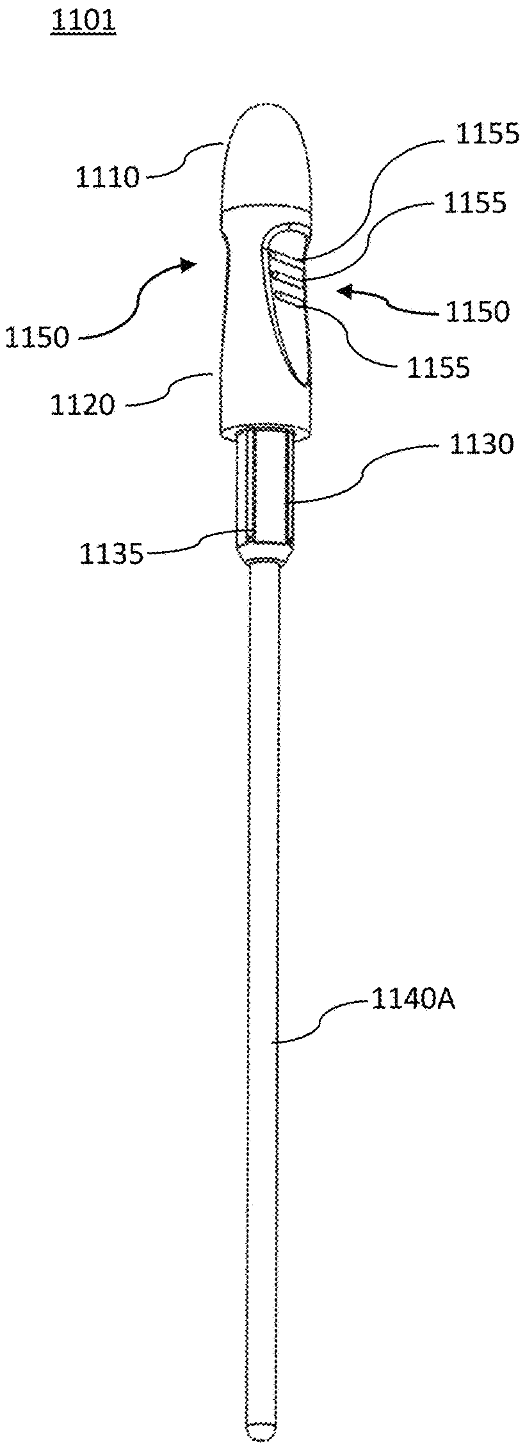
FIG. 11A is a schematic diagram of a top perspective view of a first exemplary stylet that may be used with one or more of the surgical drains disclosed herein, in accordance with some embodiments of the present invention.

FIG. 11A is a schematic diagram of a top perspective view of a first exemplary stylet 1101 that may be used with one or more of the surgical drains disclosed herein, such as surgical drain 1000. Stylet 1101 includes a tip 1110, a base 1120, a stylet coupling 1130 that includes a plurality of optional tube engagement mechanisms 1135, a first stiffening member 1140A, and a grasping feature 1150. In some embodiments, tip 1110, base 1120, stylet coupling 1130, optional tube engagement mechanisms 1135, and/or a grasping feature 1150 may be made from the same material (e.g., silicon or plastic) and/or molded at the same time. In some embodiments, tip 1110, base 1120 (with grasping feature 1120), stylet coupling 1130, and tube engagement mechanisms 1135 may be affixed, glued, and/or over-molded onto an end of first stiffening member 1140A, which may enable use of a first material for first stiffening member 1140A and a second material for tip 1110, base 1120 (with grasping feature 1120), stylet coupling 1130, tube engagement mechanisms 1135. At times, stylet 1101 may be configured and/or manufactured so that a portion of stiffening member extends into stylet coupling 1130 and base 1120 to add stiffness thereto.

Grasping feature 1150 may be configured to enable grasping and/or manipulation by a clinician wearing surgical gloves that may be wet and/or sticky due to blood or other substances present thereon. As shown in FIG. 11A, grasping feature 1150 is instantized as two notches positioned on either side of base 1120 in a symmetrical or asymmetrical manner that include tactile feedback members 1155 in the form of ridges that may assist the clinician when grasping and/or manipulating stylet 1101 and/or a surgical drain using stylet 1101.

Stylet 1101 may be configured to, for example, add stiffness to a surgical drain, such as surgical drain 1000 via insertion of first stiffening member 1140A into a central lumen (e.g., central lumen 1020) of a tube like tube 1010 as shown in, for example, FIGS. 12A-12G. To that end, first stiffening member 1140A may be sized, shaped, and/or configured to fit within a central lumen of a tube of a surgical drain and add stiffness thereto. Often times, stiffening member will be flexible, but less flexible than the tube of the surgical drain. Materials (e.g., plastic, metal, and/or PVC) for stiffening member may be different from the materials used to manufacture tip 1110, base 1120, stylet coupling 1130 and/or a grasping feature 1150.

Stylet coupling 1130 may be a male coupling sized, shaped, and configured to be inserted into a central lumen of a tube of a surgical drain and removably remain therein via, for example, engagement of optional tube engagement mechanisms 1135 with an interior surface of tube 1010. Optional tube engagement mechanisms 1135 may be, for example, ribs, barbs, and/or O-rings configured to engage with an interior surface of the tube and achieve a secure fit therein until stylet 1101 and/or stylet coupling 1130 is removed from the tube via, for example, manual extraction, which may be facilitated by a clinician holding grasping feature 1150 and pulling in a direction opposite that of the drainage component, usually following placement of the surgical drain in the hollow organ and/or tissue, to extract stylet 1101 from the tube so that, for example, the tube may be coupled to a source of suction and/or a fluid collection container. Optional tube engagement mechanisms 1135 may be configured to better control and/or reduce variability in the retention force required to hold stylet 1101 within lumen 1020.

A shape and/or size of tip 1110 may be configured to enable atraumatic insertion of stylet 1101 and/or a surgical drain including stylet 1101 into an orifice (e.g., natural and/or surgical opening) in a hollow organ and/or tissue. When hollow organ and/or tissue is a uterus, tip 1110 may be further configured to atraumatically be inserted into and pushed through a surgical opening in the uterus and an undilated, or minimally dilated (e.g., 0.5-5 cm), cervical canal as, for example, disclosed herein. In particular, first stiffening member 1140A may be configured to assist with manually pushing tip 1110 and the surgical drain's tube through the cervical and vaginal canals so that tip 1110, base 1120, grasping feature 1150, and, in some cases, a portion of the tube proximate to base 1120 extend from the vagina so that that stylet 1101 may be extracted from the tube and the tube may be coupled to, for example, suction and/or a fluid collection container.

Figure 11B:
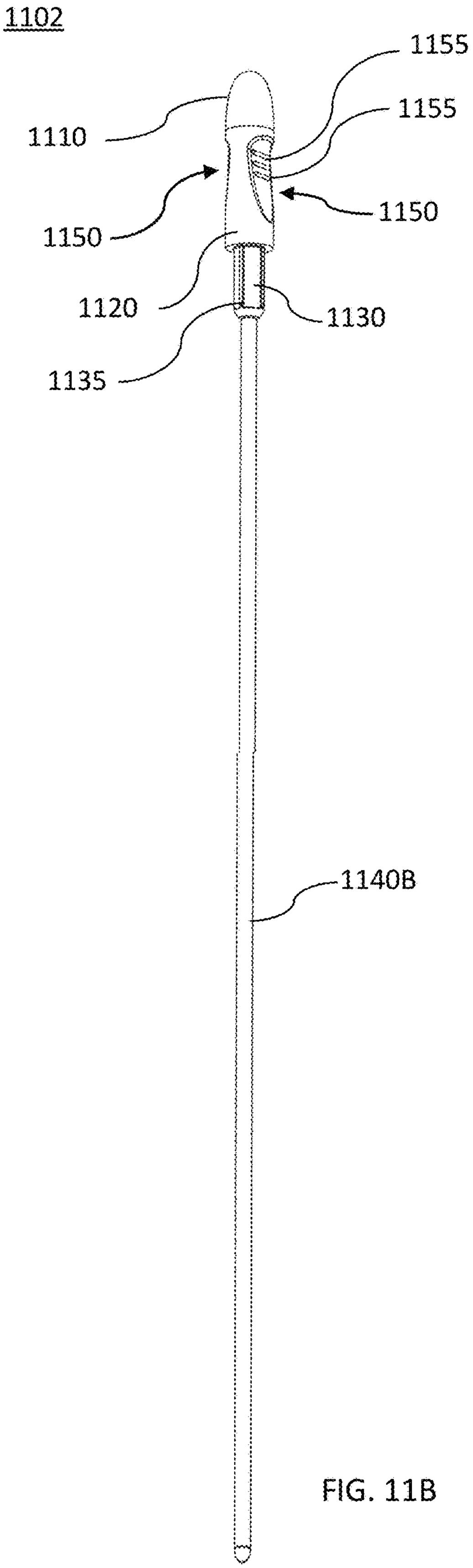
FIG. 11B is a schematic diagram of a top perspective view of a second exemplary stylet that may be used with one or more of the surgical drains disclosed herein, in accordance with some embodiments of the present invention.

In some embodiments, a stiffening member of a stylet may be sized, shaped, and/or configured to extend through tube 1010 and, optionally, a portion of a drainage component like drainage component 100. A drawing of an exemplary stylet 1102 with an elongated stiffening member 1140B is provided by FIG. 11B. Stylet 1102 includes the same components as stylet 1101 with the exception of elongated stiffening member 1140, which is sized and configured to extend through tube 1010 and drainage component 100 as shown in the cross-section of FIG. 12F. Stylet 1102 may be used in situations where a surgical drain is inserted into tissue and/or a hollow organ, wherein the drainage component enters the tissue/hollow organ first (as opposed to tip 1110 first).

Figure 12A:
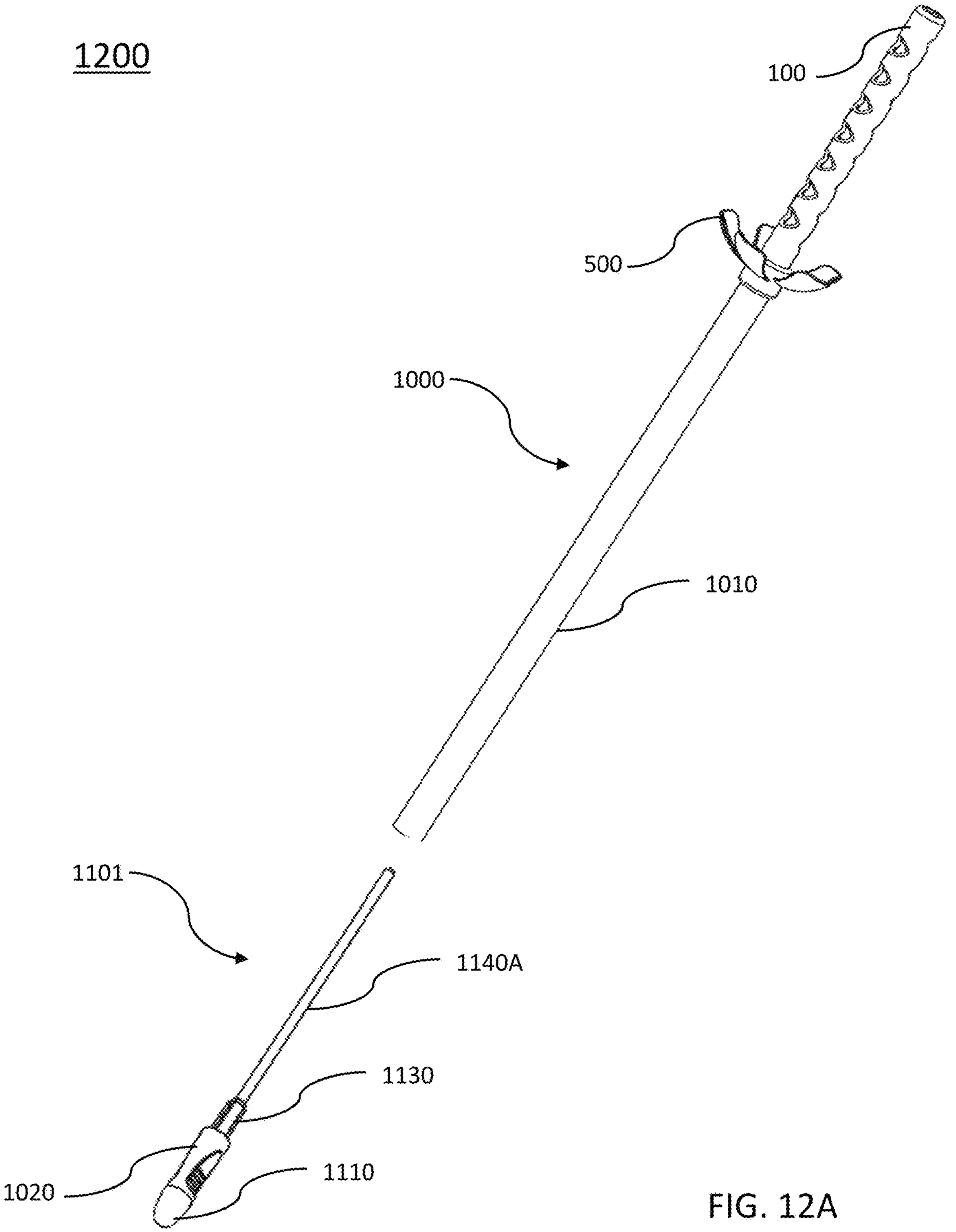
FIG. 12A is a schematic diagram of an exploded view of a surgical drain, in accordance with some embodiments of the present invention.
Figure 12B:
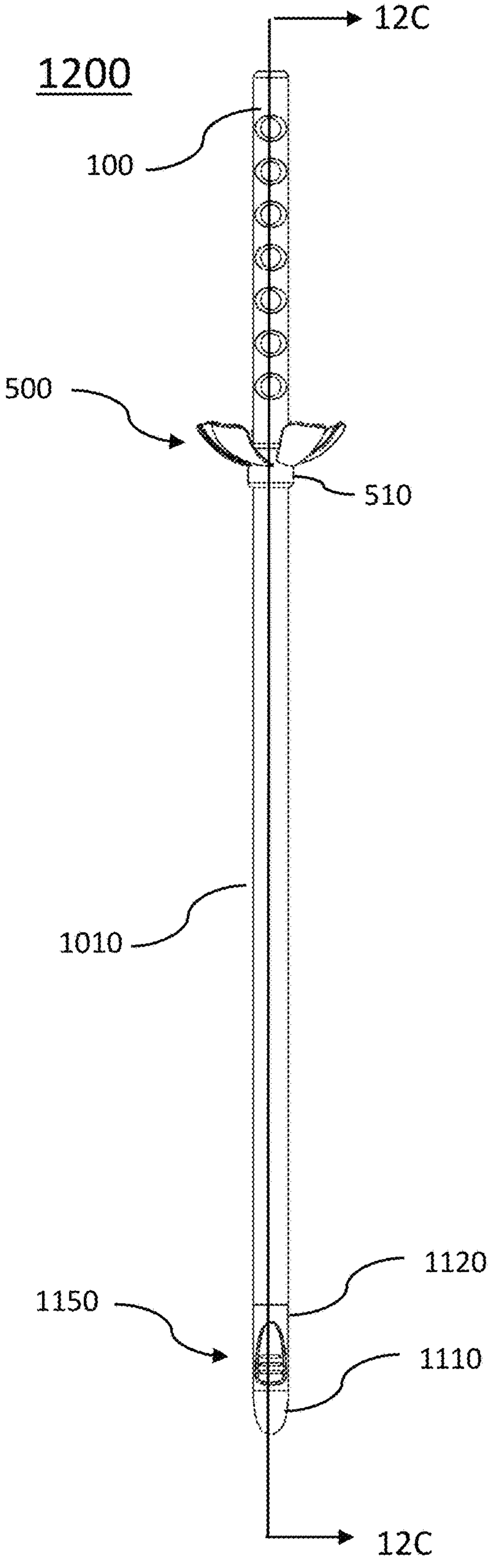
FIG. 12B is a schematic diagram of a top view a surgical drain when assembled as arranged in the exploded view of FIG. 12A, in accordance with some embodiments of the present invention.
Figure 12C:
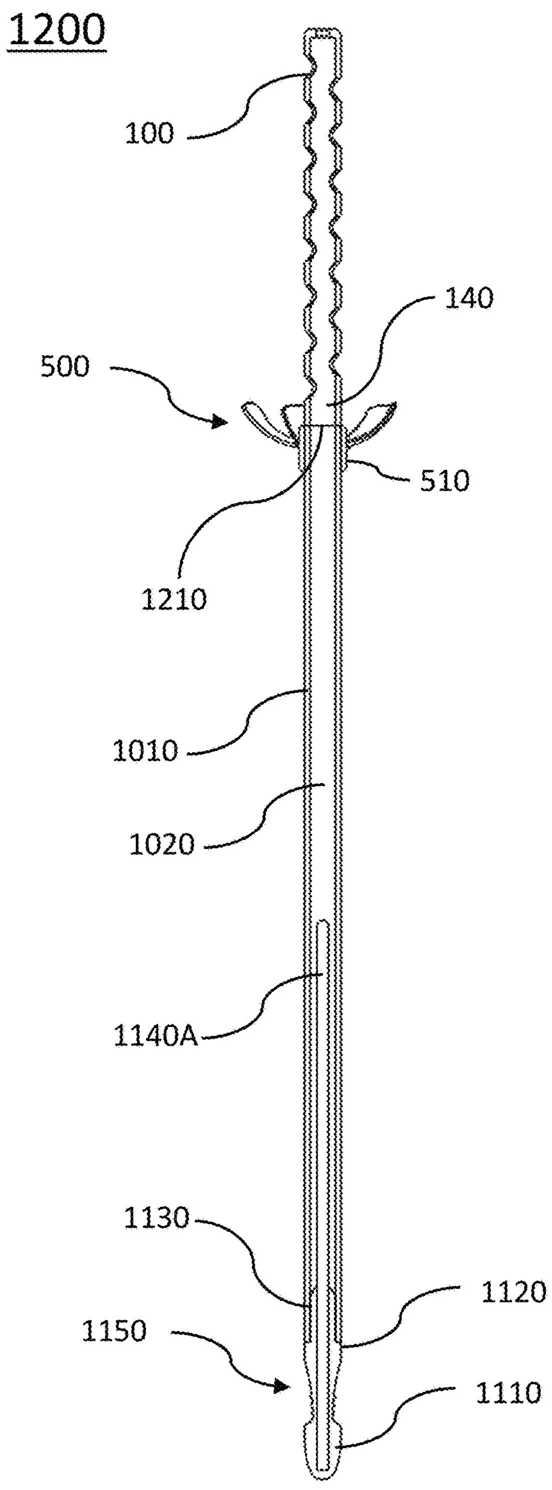
FIG. 12C is a schematic diagram of a cross-section view of the surgical drain of FIG. 12B, in accordance with some embodiments of the present invention.
Figure 12D:
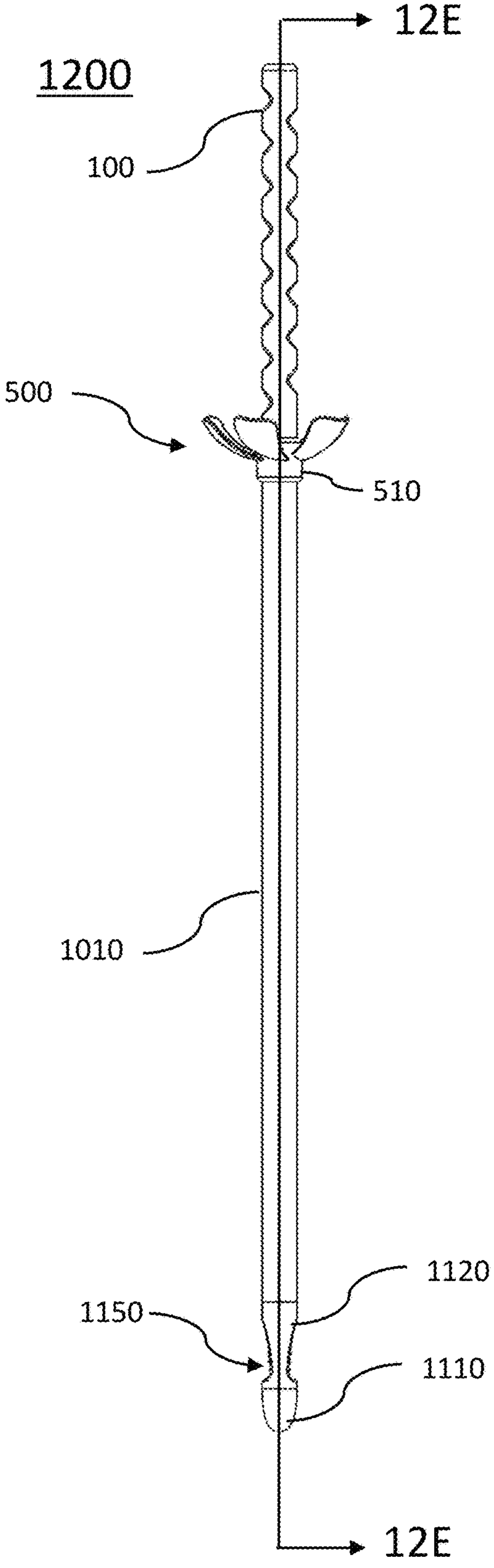
FIG. 12D is a schematic diagram of a side view of the surgical drain of FIG. 12B, in accordance with some embodiments of the present invention.
Figure 12E:
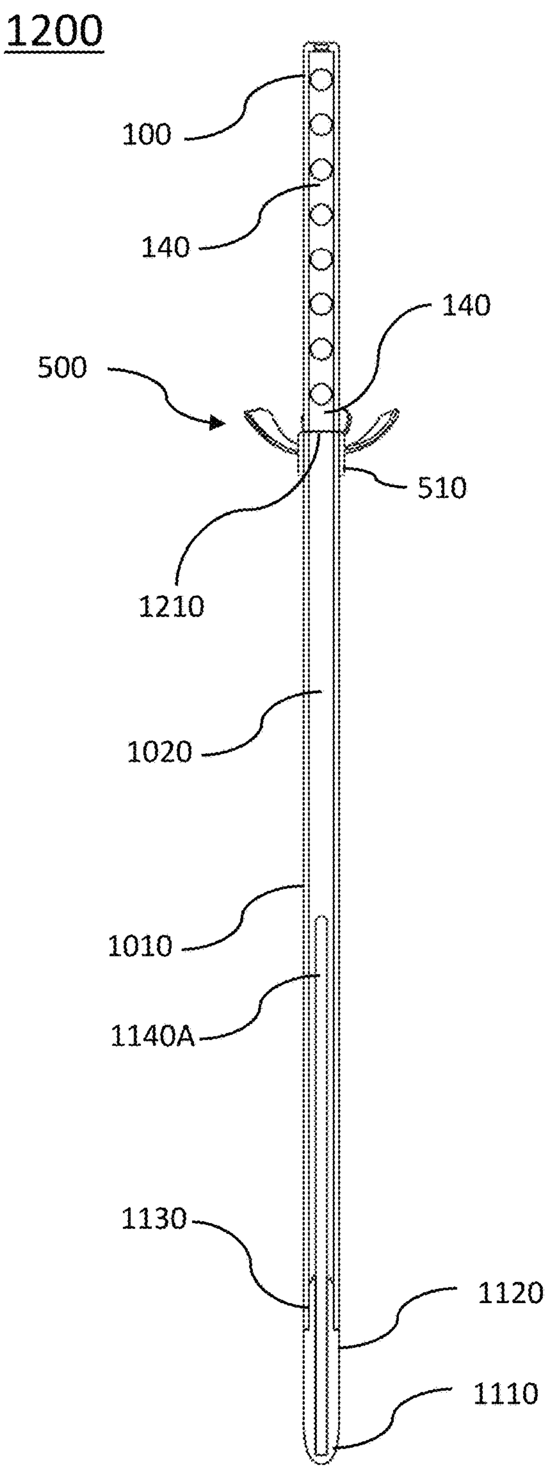
FIG. 12E is a schematic diagram of a cross-section view of the surgical drain of FIG. 12B, in accordance with some embodiments of the present invention.

FIGS. 12A-12E are schematic diagrams that provide various views of a surgical drain 1200 that includes the components of surgical drain 1000 and stylet 1101. In particular, FIG. 12A provides an exploded view of a surgical drain 1200; FIG. 12B provides a top view of surgical drain 1200 that includes a vertical bisecting line A-A superimposed thereon; FIG. 12C provides a cross-section view of surgical drain 1200 along the vertical bisecting line 12C-12C of FIG. 12B; FIG. 12D provides a side view of surgical drain 1200 that includes a vertical bisecting line 12E-12E superimposed thereon; and FIG. 12E provides a cross-section view of surgical drain 1200 along the vertical bisecting line 12E-12E of FIG. 12D. The exploded view of FIG. 12A illustrates how stylet 1101 and, in particular, first stiffening member 1140A may be aligned with tube 1010 (and, in particular, central lumen 1020) of surgical drain 1000 prior to insertion therein and/or following extraction therefrom. FIGS. 12B-12E show stylet 1101 resident in assembled surgical drain 1200 with stiffening member 1040 residing within central lumen 1020 and stylet coupling 1030 engaged within an interior diameter of tube 1010 until fully inserted therein as may be seen in the cross-sections of FIGS. 12C and 12E. When assembled, stylet coupling 1130 and first stiffening member 1140A are positioned within tube 1010 (as shown in, for example, FIGS. 12C and 12E). As may be seen in FIGS. 12C and 12D, grasping feature 1150 may include a notch, which may facilitate grasping and/or holding of base 1120 so that stylet 1101 may be extracted from tube 1010 following placement of surgical drain 1200 in a hollow organ and/or tissue as, for example, described herein. Although FIGS. 12C and 12E show first stiffening member 1140A extending approximately halfway (or less) through lumen 1020, this need not always be the case. For example, in some embodiments first stiffening member 1140A may extend to positioning mechanism 500. Alternatively, first stiffening member 1140A may extend partially, or completely through drainage component lumen 140. FIGS. 12C and 12E also show a junction 1210 between drainage component 100 and tube 1010 and how shaft 510 wraps around junction 1210 so that neither lumen 140 nor lumen 1120 are obstructed.

Figure 12F:
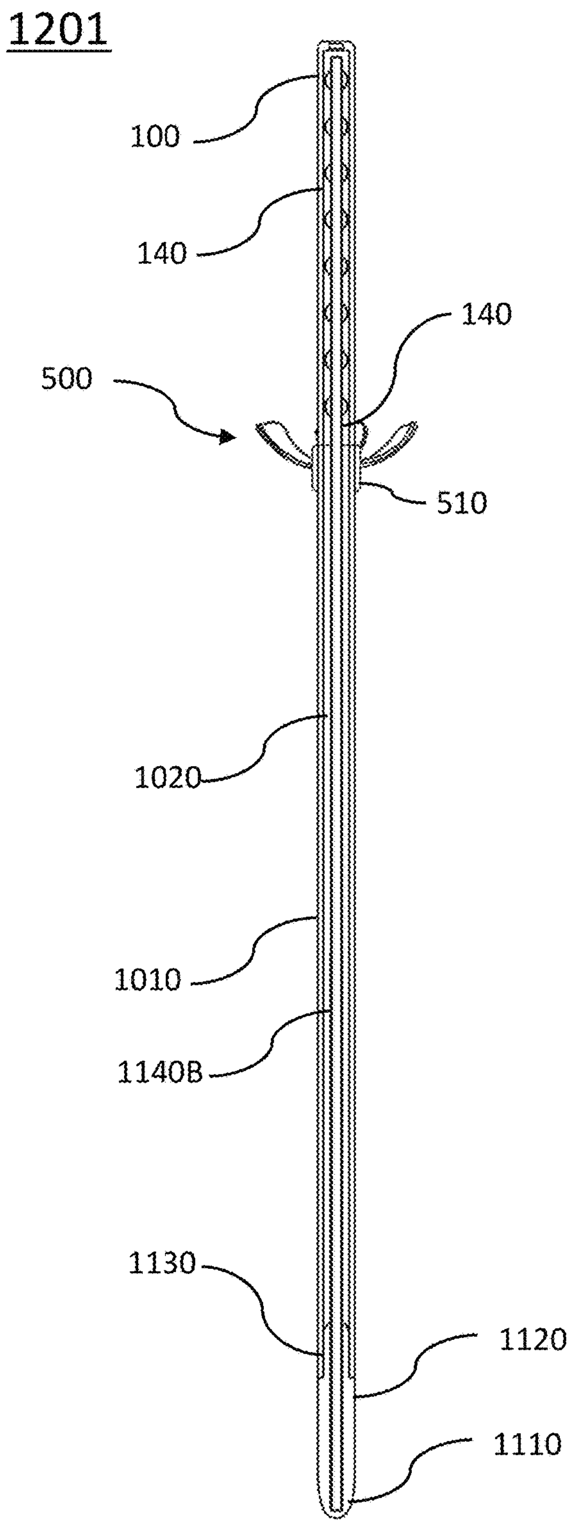
FIG. 12F is a schematic diagram of a cross-section view of a surgical drain with the stylet of FIG. 11B inserted therein, in accordance with some embodiments of the present invention.
Figure 12G:
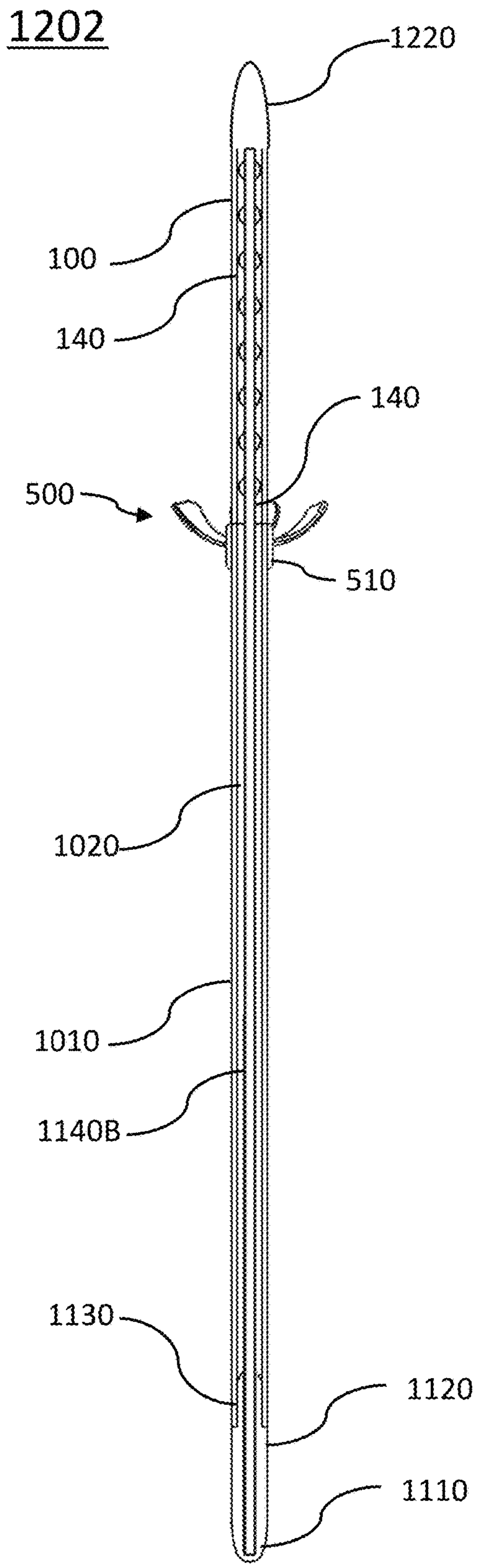
FIG. 12G is a schematic diagram of a cross-section view of a surgical drain with an end cap, in accordance with some embodiments of the present invention.

FIG. 12F is a schematic diagram of a cross-section view of a surgical drain 1201 that includes the components of surgical drain 1000 and stylet 1102. As may be seen in the cross-section of FIG. 12F, second stiffening member 1040B extends through lumen 1020 of tube 1010 and lumen 140 of drainage component 100. Second stiffening member 1040B may add a degree of stiffness along the entire and/or most of surgical drain 1201 that may, for example, enable handling and/or positioning of surgical drain 1201 so that drainage component 100 may be inserted into and/or pushed through tissue and/or a hollow organ without bending or kinking. Surgical drain 1201 may be used, for example, in situations wherein drainage component 100 is inserted into tissue and/or hollow organ first as may occur when, for example, a natural orifice and/or channel (e.g., vagina, endocervical canal, esophagus, etc.) is used to place surgical drain 1201. FIG. 12G is a schematic diagram of a cross-section view of a surgical drain 1202 that includes all the components of surgical drain 1201 and as well as an end cap 1220 that extends from and/or is affixed to an end of drainage component 100 furthest away from tip 1110. End cap 1220 may be sized, shaped, and/or configured to assist with pushing surgical drain 1202 through the vaginal and cervical canals so surgical drain 1202 may be seated within a patient's uterus as shown in, for example, FIGS. 20A-20C and discussed herein.

Figure 13A:
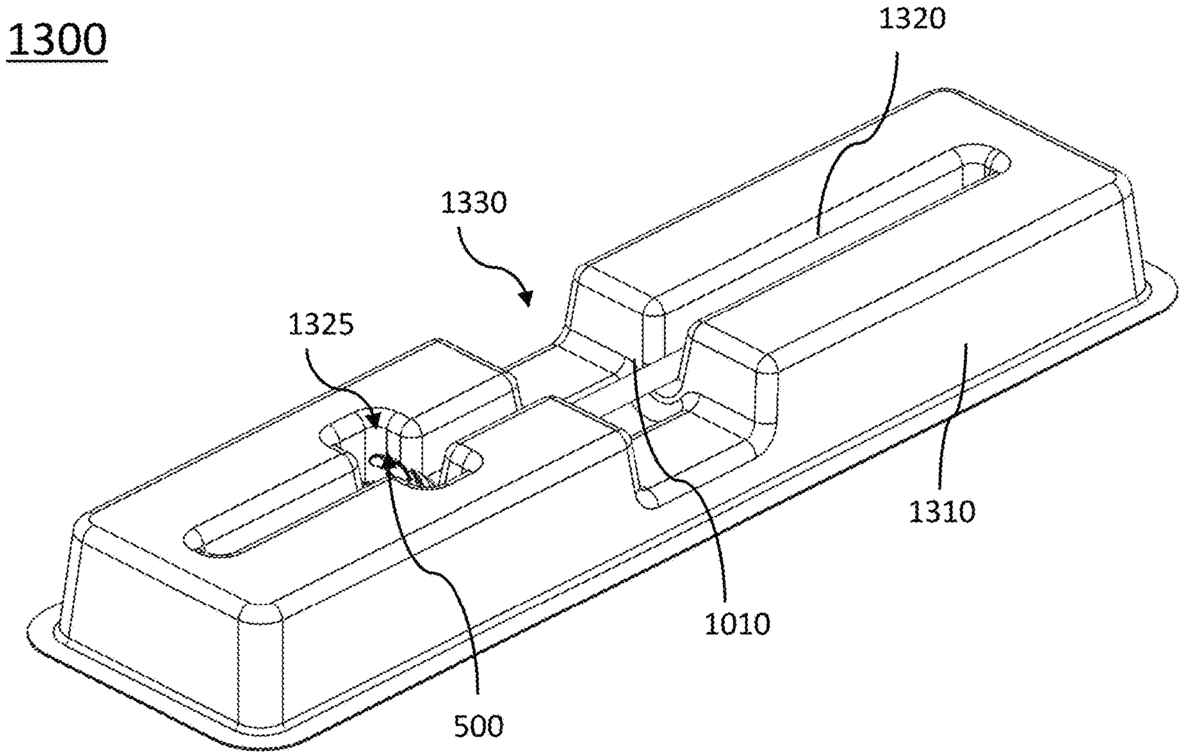
FIG. 13A is a schematic diagram of a top-perspective view of exemplary packaging for the surgical drain of FIG. 10B or 12B with the surgical drain positioned therein, in accordance with some embodiments of the present invention.
Figure 13B:
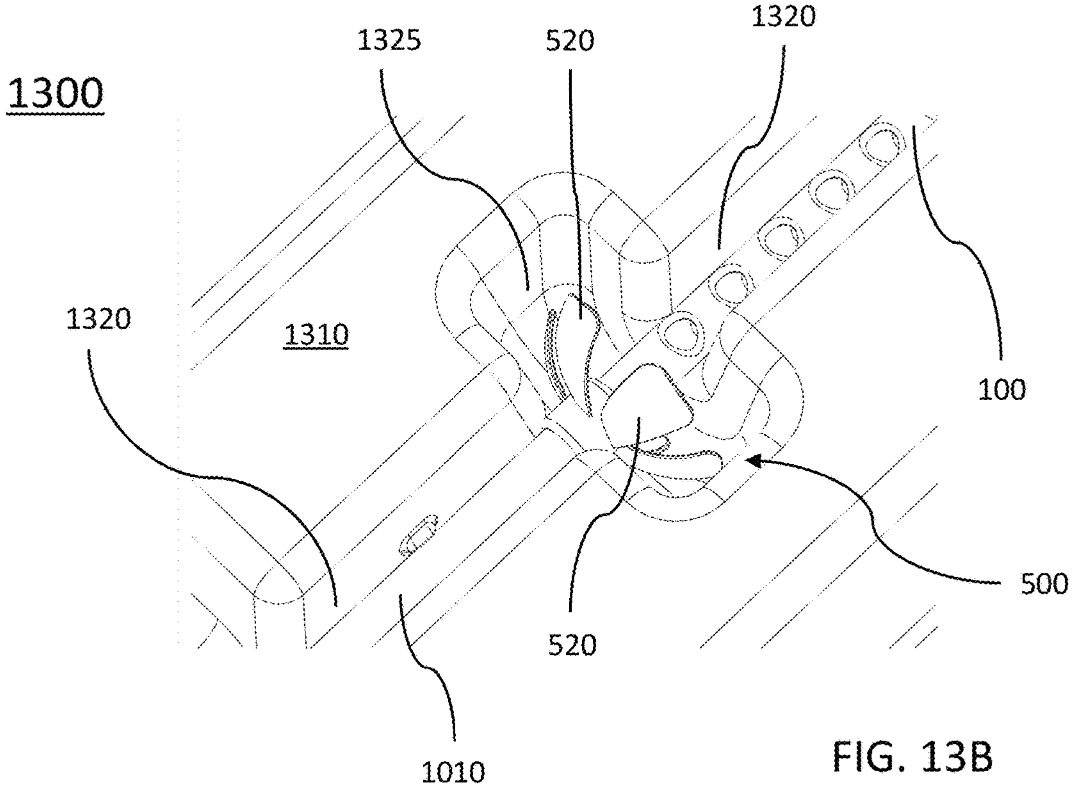
FIG. 13B is a schematic diagram of a top-perspective close-up view of a portion of the packaging of FIG. 13A with the surgical drain of FIG. 10B or 12B positioned therein, in accordance with some embodiments of the present invention.
Figure 13C:
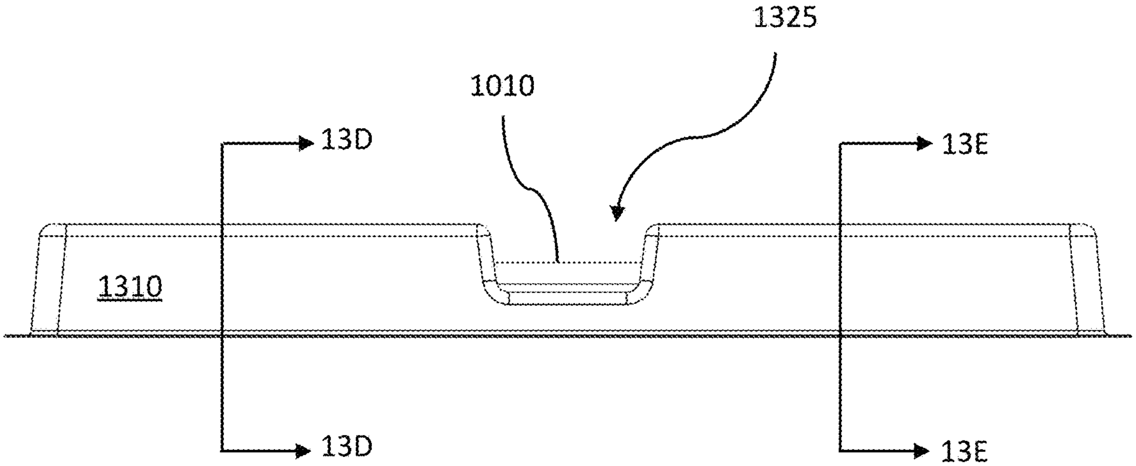
FIG. 13C is a schematic diagram of a side view of the packaging of FIG. 13A 1300 with the surgical drain of FIG. 10B or 12B positioned therein, in accordance with some embodiments of the present invention.
Figure 13D:
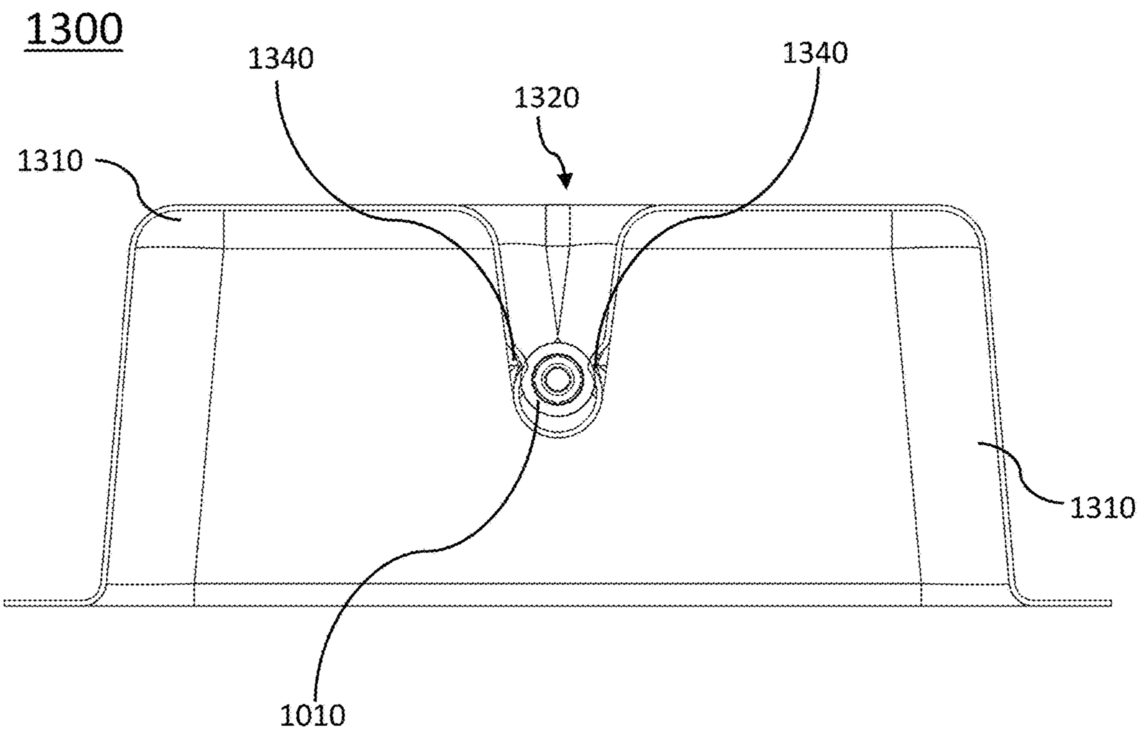
FIG. 13D is a schematic diagram of a first cross-section view of the packaging of FIG. 13A with the surgical drain of FIG. 10B or 12B positioned therein, in accordance with some embodiments of the present invention.
Figure 13E:
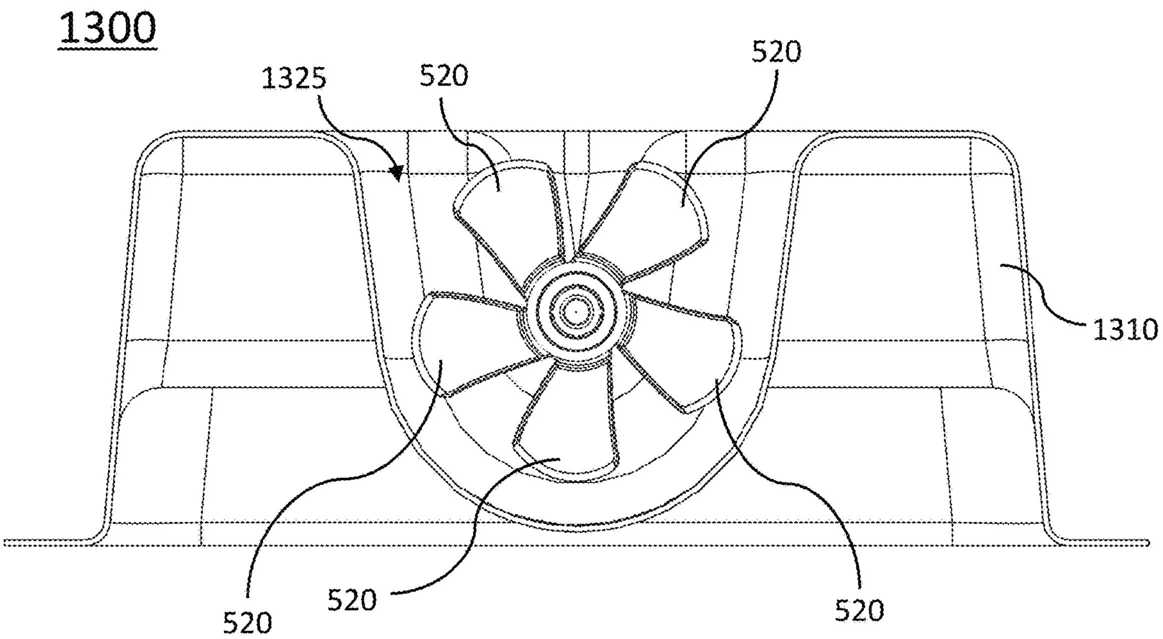
FIG. 13E is a schematic diagram of a second cross-section view of the packaging of FIG. 13A with the surgical drain of FIG. 10B or 12B positioned therein, in accordance with some embodiments of the present invention.

FIGS. 13A-13E are schematic diagrams that provide various views of exemplary packaging 1300 for surgical drain 1000 and/or 1200, wherein FIG. 13A provides a top-perspective view of packaging 1300 with surgical drain 1200 positioned therein, FIG. 13B provides a top-perspective close-up view of a portion of packaging 1300 with surgical drain 1000 or 1200 positioned therein, FIG. 13C provides a side view of packaging 1300 with surgical drain 1000 or 1200 positioned therein that includes a first bisecting line 13D-13D and a second bisecting line 13E-13E positioned thereon, FIG. 13D provides a first cross-section view of packaging 1300 with surgical drain 1000 or 1200 positioned therein taken along bisecting line 13D-13D (shown in FIG. 13C); and FIG. 13E provides a second cross-section view of a packaging 1300 with surgical drain 1000 or 1200 positioned therein along bisecting line 13E-13E of FIG. 13C.

Package 1300 includes a base 1310 with a central channel 1320 configured to accept insertion of tube 1010 and drainage component 100 therein and a cross channel 1325 configured to accept insertion of first positioning mechanism 500 in an unfolded configuration as shown in, for example, FIGS. 13E and 13B. Channel 1325 may be configured to allow extensions 520 to reside in an open, uncompressed, state which may prevent extensions 520 from taking a set, or being trained, to hold a closed or semi-closed state over time as may occur if extensions 520 were arranged in a closed or folded state while being sterilized, shipped, and/or waiting for use in packaging that did not include channel 1325.

Package 1300 also includes an indented feature 1330 positioned in an approximate center of a length of package 1300 and oriented approximately perpendicular to channel 1320 as shown in, for example, FIGS. 13A and 13C. Indented feature 1330 may be configured to expose a portion of tube 1010 so that it may be easily grasped when removing surgical drain 1000 or 1200 from package 1300. In some embodiments, surgical drain 1000 or 1200 may be held in place by one or more retention features (e.g., bumps or raised features) 1340 positioned along channel 1320. Retention features 1340 may be configured to be deformable to, for example, move or yield when surgical drain 1000 or 1200 is inserted into channel 1320 and then move back to an original position to hold surgical drain 1000 or 1200 within channel 1320 once inserted therein as shown in, for example, FIG. 13D. In some embodiments, exemplary package 1300 may be configured to cooperate with a lid or other outer packaging (e.g., a bag, pouch, peel open, and/or sleeve) (not shown) that may serve to protect surgical drain 1000 or 1200 and/or keep it sterile until ready for use. In some embodiments, package 1300 and all contents (e.g., surgical drain 1000 or 1200) may be sterilized by, for example, exposure to gamma irradiation.

Figure 14A:
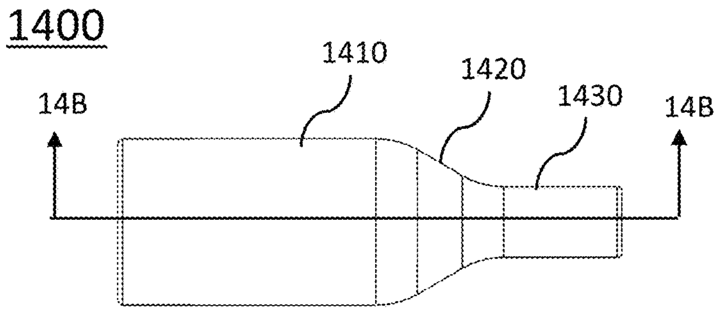
FIG. 14A is a schematic diagram of a top view of a connector, in accordance with some embodiments of the present invention.
Figure 14B:
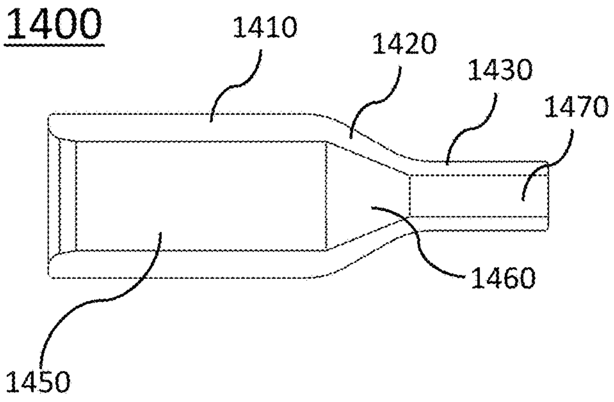
FIG. 14B is a schematic diagram of a cross section view of the connector of FIG. 14A, in accordance with some embodiments of the present invention.
Figure 15:
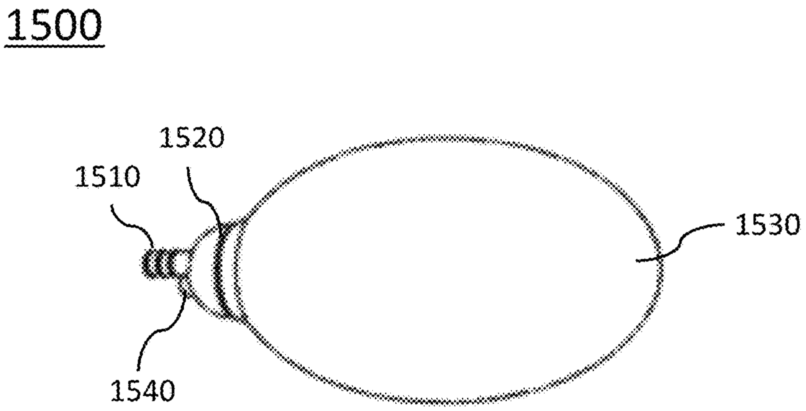
FIG. 15 is a schematic diagram of a side view of a suction reservoir device, in accordance with some embodiments of the present invention.

FIGS. 14A and 14B are schematic diagrams that respectively provide a side view and a cross-section view along bisecting line 14B-14B (shown in FIG. 14A) of a connector 1400. Connector 1400 includes a barrel 1410, a tapered region 1420, an extension 1430, a barrel lumen 1450, a tapered region lumen 1460, and an extension lumen 1470. Connector 1400 may be sized, shaped, and/or configured to couple to an end of tube of a surgical drain, such as tube 1010 (once stylet 1101 has been removed therefrom) as shown in, for example, FIGS. 16A-16E and disclosed herein. More particularly, barrel 1410 may be configured to slide over and engage with an exterior surface of tube 1010 until the end of the tube 1010 abuts (e.g., is stopped by) an interior surface of tapered region so that an end of tube 1010 is positioned within barrel lumen 1450 but does not enter tapered region lumen 1460. Extension lumen 1470 may be sized, shaped, and configured to accept insertion of another device (e.g., a coupling of reservoir device 1500 as shown in FIG. 15 and discussed herein) and extension 1430 may be configured to engage with and/or cover an inserted portion of the device. In many embodiments, barrel lumen 1450, tapered region lumen 1460, and extension lumen 1470 may be sized, shaped, and configured to be in communication (e.g., liquid and/or gas) with lumen 1020 of tube 1010.

FIG. 15 is a schematic diagram of a side view of a suction reservoir device 1500, that, in some embodiments, may be instantized as a Jackson Pratt drain. Suction reservoir device 1500 includes a barbed coupling 1510, a helmet 1520, a reservoir 1530, and a port 1540. Barbed coupling 1510 may include a one-way duckbill valve (not shown) that allows fluid to enter reservoir 1530 from tube 1010 but does not allow fluid from reservoir 1530 to enter tube 1010. Port 1540 may be configured to couple to a device (e.g., an evacuation tube or fluid collection device) configured to evacuate fluid from reservoir 1530 to, for example, measure a volume of fluid and/or prevent build-up or overflowing of fluid within reservoir 1530. When port 1540 is not in use, it may be covered by a plug. Reservoir 1530 may be made from a flexible material and, in some embodiments, suction reservoir device 1500 may be actuated by the squeezing reservoir 1530, which may act to displace air resident within a cavity of reservoir 1530 when port 1540 is open (i.e., not covered) and provides a pathway for the air within reservoir 1530 to escape into the environment. Once air is sufficiently evacuated from reservoir 1530, port 1540 may be plugged, or otherwise sealed, and reservoir 1530 may be released (e.g., a source of the squeezing force may be removed). As reservoir 1530 attempts to equalize the negative pressure caused by pushing the air out (i.e., return to its pre-squeezed shape), suction may be applied to a lumen of barbed coupling 1510, which is in communication with tapered lumen 1460, lumen 1020 of tube 1010, and lumen 140 of drainage component 100 thereby communicating the suction to a hollow organ and/or tissue in which a surgical drain coupled to suction reservoir device 1500 is placed, thereby enabling fluid that may be present within the hollow organ and/or tissue to be drawn into one or more drainage holes 120 of drainage component 100 to be may be evacuated from the hollow organ and/or tissue communication to lumens 140, 1020, 1460 and eventual collection in the cavity of reservoir 1530. In some embodiments, barbed coupling 1510 may not be aligned with a center of helmet 1520 and, instead may be positioned to axially align with a drainage component when coupled to a surgical drain, such as surgical drain 1000 as shown in FIGS. 16A-16D.

Figure 16A:
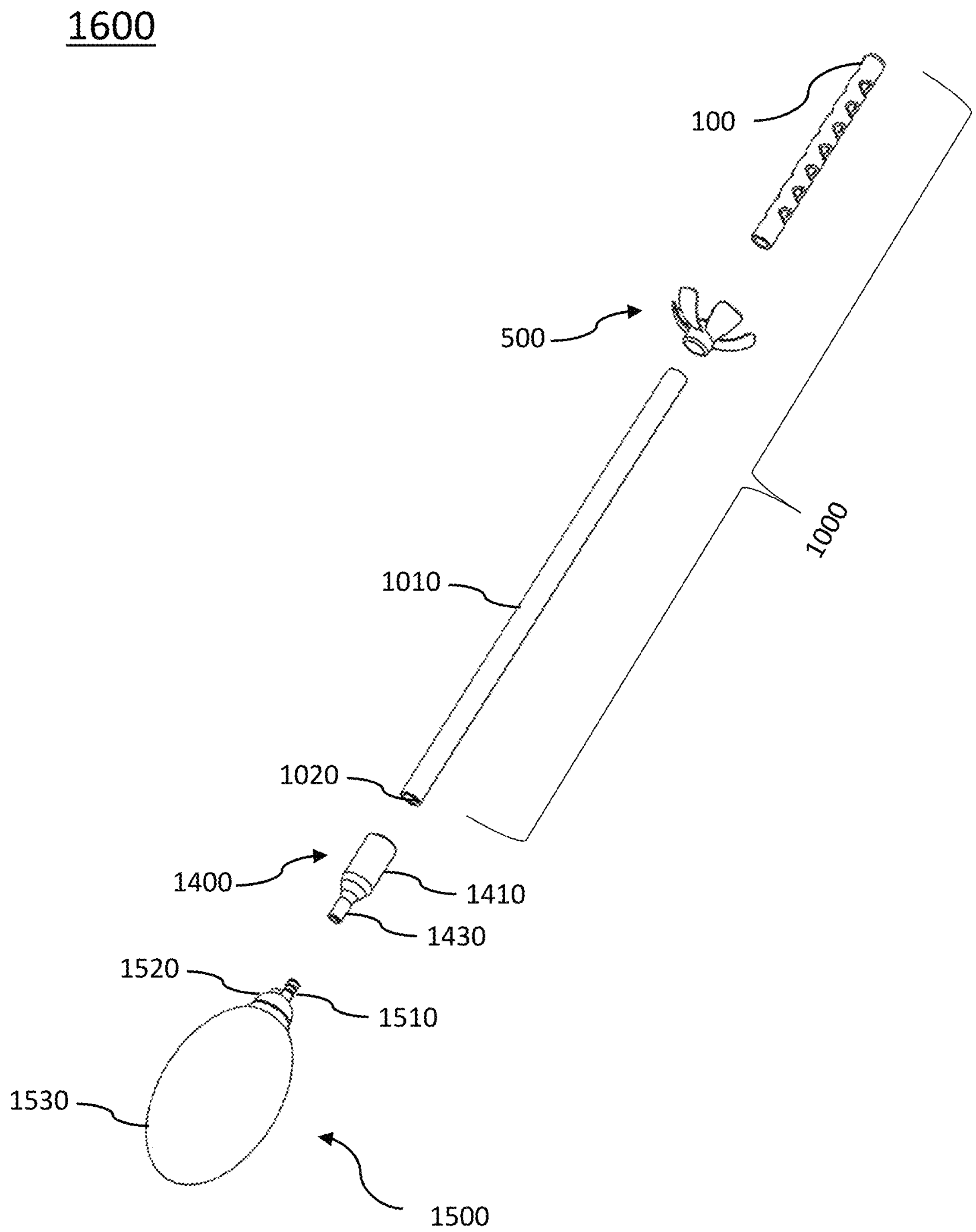
FIG. 16A is a schematic diagram of an exploded view of a surgical drain/suction reservoir device assembly, in accordance with some embodiments of the present invention.
Figure 16B:
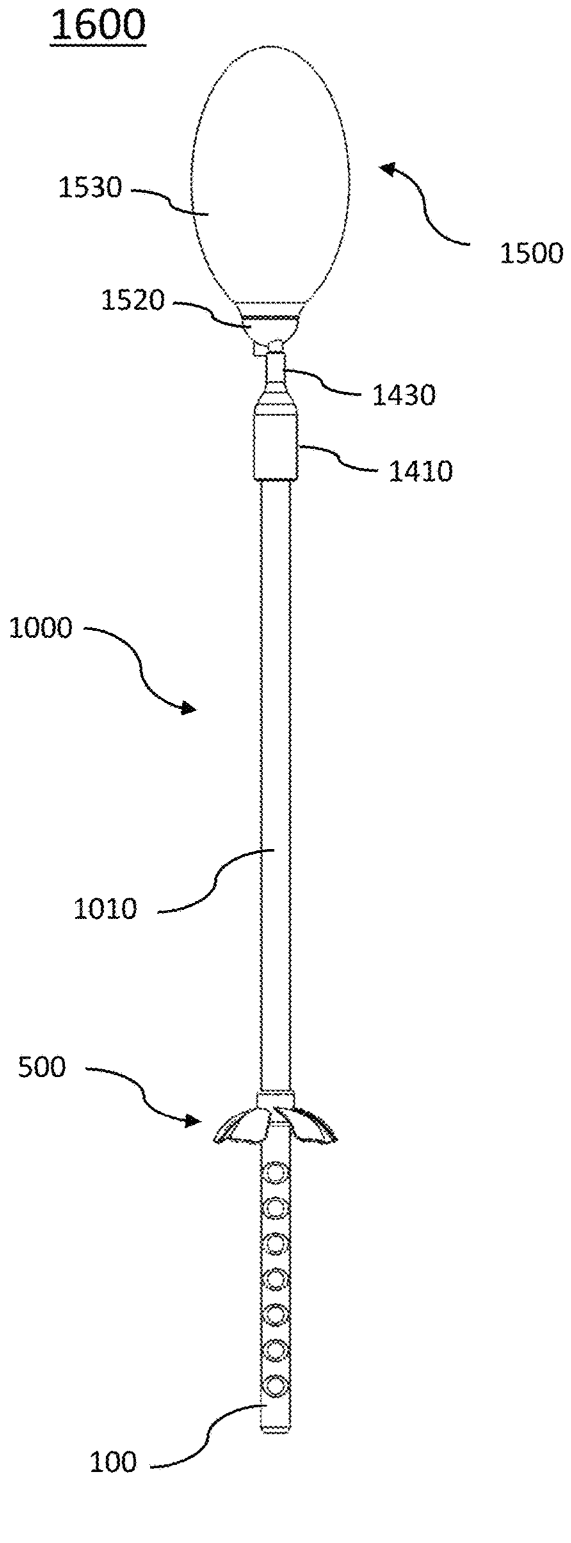
FIG. 16B is a schematic diagram of a top view of a drain/suction reservoir device assembly assembled as shown in FIG. 16A, in accordance with some embodiments of the present invention.
Figure 16C:
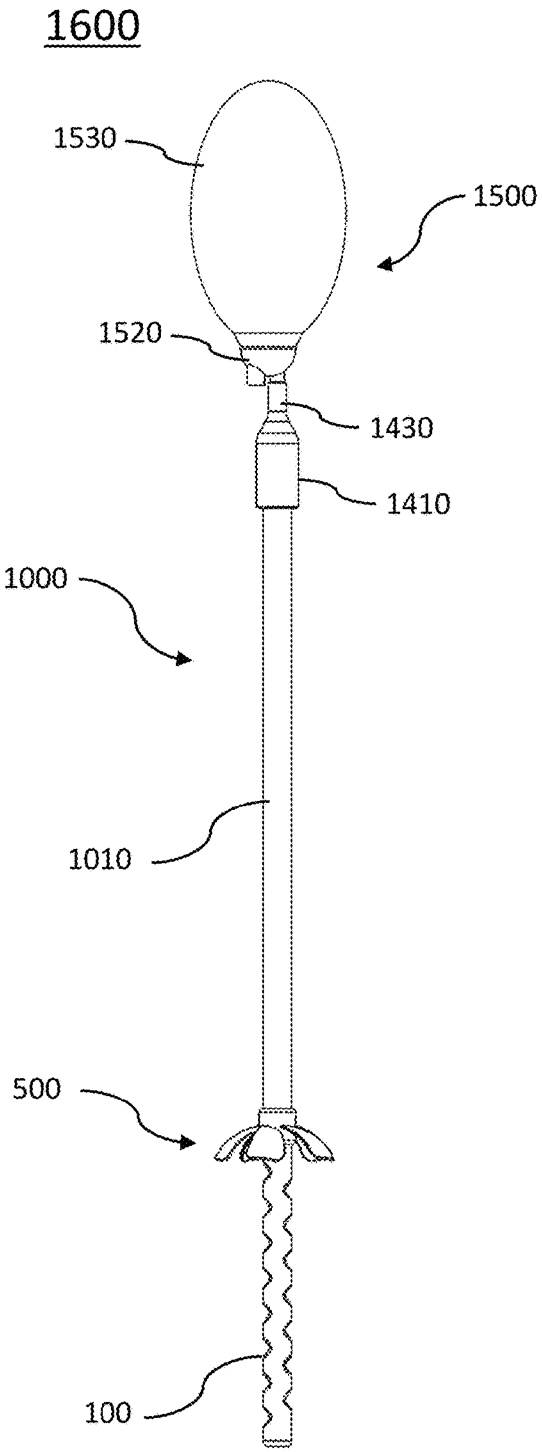
FIG. 16C is a schematic diagram of a side view of the drain/suction reservoir device assembly of FIG. 16B, in accordance with some embodiments of the present invention.
Figure 16D:
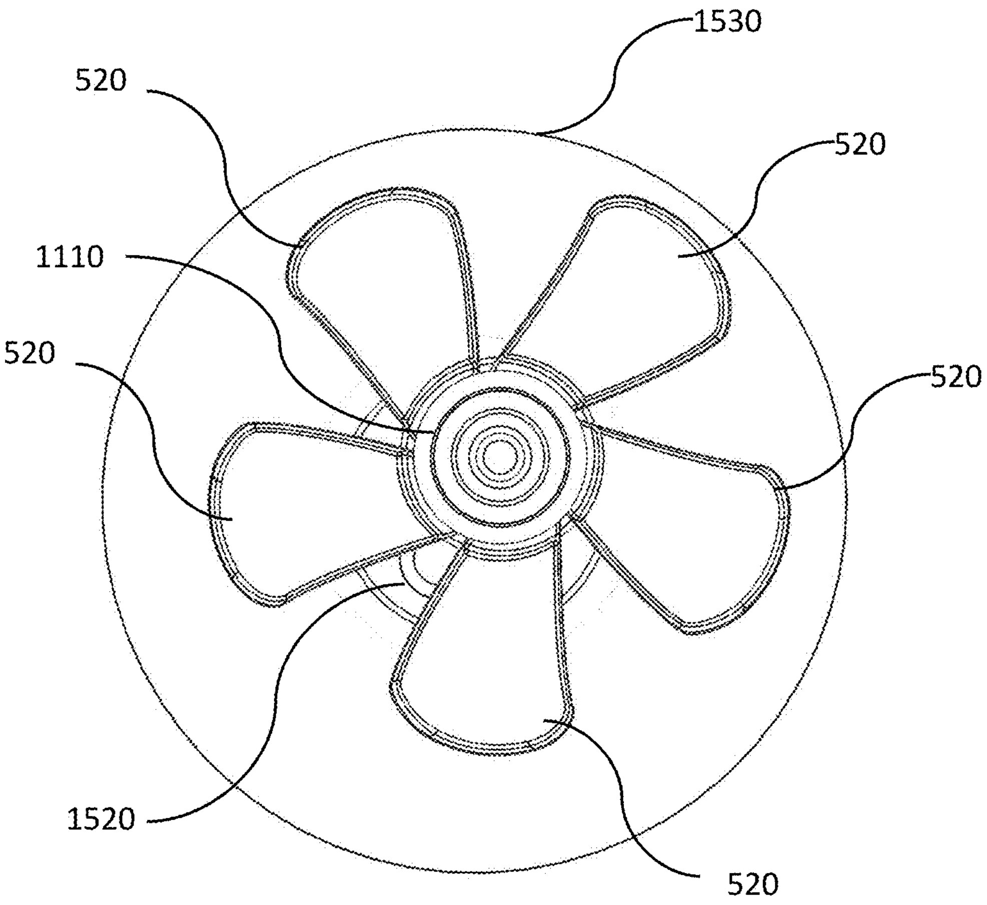
FIG. 16D is a schematic diagram of a rear view of the drain/suction reservoir device assembly of FIG. 16B, in accordance with some embodiments of the present invention.

FIG. 16A is a schematic diagram of an exploded view of a surgical drain/suction reservoir device assembly 1600 that includes surgical drain 1000, connector 1400, and suction reservoir device 1500 that shows how drainage component 100, positioning mechanism 500, tube 1010, lumen 1020, connector 1400, and barbed coupling 1510 may be arranged prior into an assembly of surgical drain 1000, connector 1400, and suction reservoir device 1500 into assembly 1600 as shown in FIGS. 16B, 16C, and 16D, which provide a top, side, and rear view, respectively, of assembly 1600 and, among other things, illustrate how barrel 1410 slides over and engages with an end of tube 1010 to connect connector 1400 to tube 1010. FIGS. 16B and 16C also show assembly 1600 after barbed coupling 1510 has been inserted and seated within extension lumen 1470 as defined by extension 1430 to generate assembly 1600. As may be seen in the top, side, and front views of FIGS. 16B, 16C, and 16D, respectively, barbed coupling 1510 may be axially aligned with drainage component 100 and is therefor, off-center with regard to, for example, bulb 1530.

Figure 17:
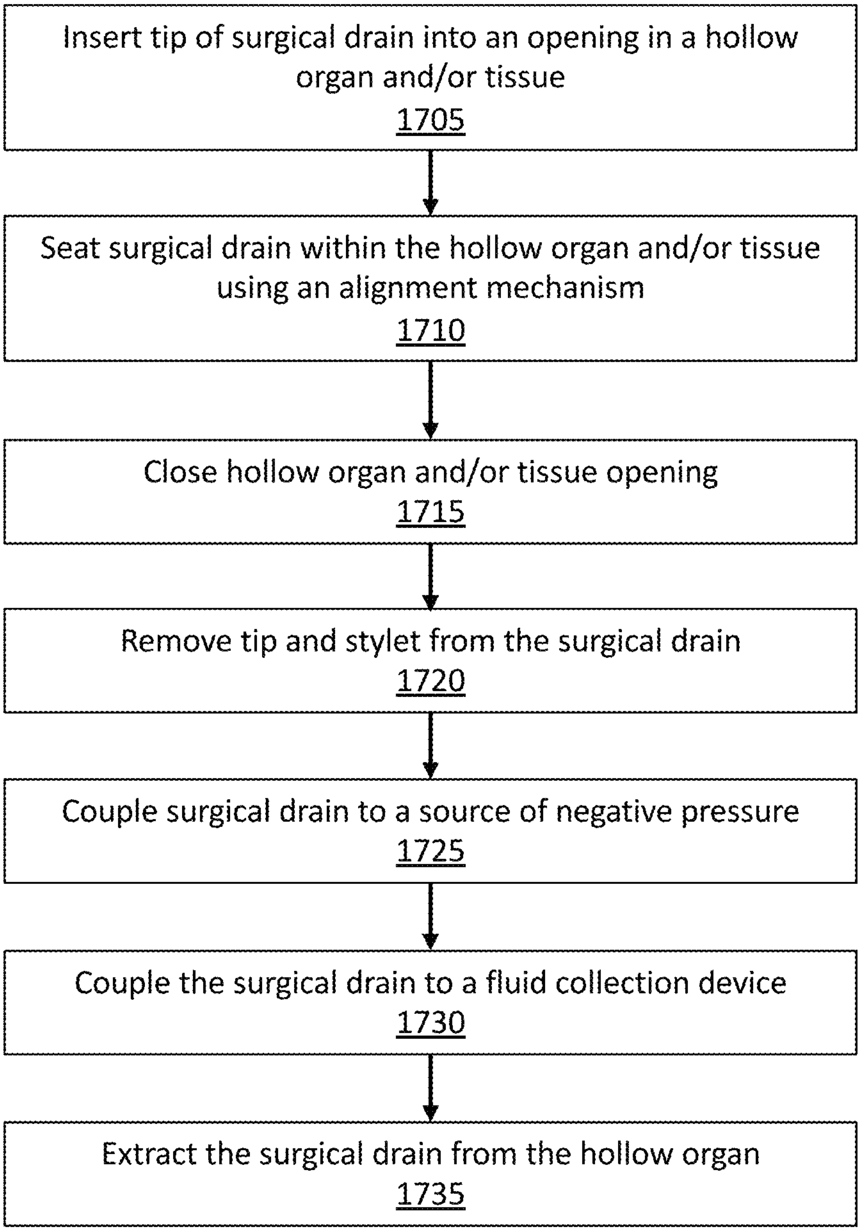
FIG. 17 provides a flowchart of a method for positioning a surgical drain within a hollow organ and/or tissue, using the surgical drain to drain and/or contract the hollow organ and/or tissue, and extract the surgical drain from the hollow organ and/or tissue, in accordance with some embodiments of the present invention.

FIG. 17 provides a flowchart of a method for positioning a surgical drain (e.g., surgical drain 1000 or 1200) or an assembly including a surgical drain (e.g., assembly 1600) within a hollow organ, such as a uterus, stomach, or bladder, and/or tissue such as lung or abdominal tissue (e.g., small intestine, large intestine, abdominal cavity, etc.), using the surgical drain to, for example, drain fluid (e.g., blood, urine, etc.) and/or blood clots from the hollow organ and/or tissue and/or contract a size, or volume, of the hollow organ and/or tissue and apply suction tamponade thereto. Initially, a tip (e.g., tip 1110) or end of a surgical drain (e.g., surgical drain 1000 or 1200) may be inserted into an opening (e.g., a naturally occurring orifice or surgical opening) within the hollow organ and/or tissue of a patient (step 1705). Next, in step 1710, the surgical drain may be seated within the hollow organ and/or tissue by, for example, positioning the drainage component within a cavity of the hollow organ and/or tissue and feeding a tube (e.g., tube 1010) to a position outside the patient's body. The surgical drain may be aligned, seated, and/or arranged within the hollow organ and/or tissue using a stylet (e.g., stylet 1101) and/or a stiffening member (e.g., first stiffening member 1140A) thereof, which may be configured to add sufficient stiffness to the surgical drain and/or a component thereof (e.g., tube 1010) to enable controlled insertion of the surgical drain into the hollow organ and/or tissue as it may be pushed through the hollow organ and/or tissue opening, hollow organ cavity, additional tissue (e.g., cervix, endocervical canal, esophagus, urethra, etc.), and/or surgical opening to be properly seated within the hollow organ and/or tissue without kinking or deforming the surgical drain. Additionally, or alternatively, the surgical drain may be aligned, seated, and/or arranged within the hollow organ and/or tissue using an positioning mechanism such as positioning mechanism 500, which may be configured to provide tactile feedback to a clinician who is placing the surgical drain within the hollow organ and/or tissue so that, for example, the clinician can feel when the drain is in a desired position and/or may prevent the surgical drain from being pushed too far into the patient's anatomy.

Optionally, when the surgical drain is inserted in step 1705 via a surgical opening in the hollow organ and/or tissue, the surgical opening may be closed (step 1715) once surgical drain is properly seated within the hollow organ and/or tissue following execution of step 1710. In some embodiments, a drainage component of the surgical drain and/or the surgical drain may be configured so that it is not positioned proximate to the surgical opening when properly seated (step 1710) to, for example, reduce a risk that the surgical drain or drainage component interferes with and/or obstructs the incision closing process and/or is caught via, for example, sutures, in the incision closing process.

In step 1720, a tip (e.g., tip 1010) and optional stylet 1101 may be removed from a lumen (e.g., lumen 1020) of the surgical drain thereby opening the lumen of the surgical drain. Then, an end of the surgical drain exposed by removal of the tip may be coupled to a source of negative pressure such as a vacuum pump and/or suction reservoir device (e.g., suction reservoir device 1500) so that negative pressure may be applied to the surgical drain, which communicates the negative pressure to the hollow organ and/or tissue via, for example, one or more drainage holes (e.g., holes 120) that may serve to apply the negative pressure to a cavity of the hollow organ and/or tissue to, for example, evacuate fluids from the hollow organ and/or tissue and/or contract a size and/or volume of the hollow organ and/or tissue, which may limit blood flowing from vessels within the hollow organ and/or tissue.

Optionally, in step 1725, an end the surgical drain not positioned within the hollow organ and/or tissue (e.g., an end of tube not proximate to the drainage component) may be coupled to, for example, a source of suction, such as a vacuum pump and/or a suction reservoir device such as suction reservoir device 1500. The amount of suction applied to the surgical drain may be within a range of 50-150 mmHg. When the surgical drain is coupled to suction reservoir device 1500, the suction may be actuated by the squeezing reservoir 1530 with port 1540 open so that air originally present within reservoir 1530 is pushed out into the environment. Then, port 1540 may be plugged, or otherwise sealed, and reservoir 1530 may be released (e.g., a source of the squeezing force may be removed) and, as reservoir 1530 attempts to return to its pre-squeezed shape, a gentle suction may be applied to a lumen of barbed coupling 1510, which is in communication with tapered lumen 1460, lumen 1020 of tube 1010, and lumen 140 of drainage component 100 thereby communicating suction to a hollow organ and/or tissue in which a surgical drain coupled to suction reservoir device may be placed so that fluid may be evacuated from the hollow organ and/or tissue via entry into one or more drainage holes 120 and communication to lumens 140, 1020, 1460 and eventual collection in the cavity of reservoir 1530. In these embodiments, fluid and/or material that collects in reservoir 1530 may be drained therefrom via port 1540.

Additionally, or alternatively, in step 1730, the end of the surgical drain exposed by removal of the tip may be coupled to a collection device (e.g., gauze, absorbent pad, bag, and/or graduated cylinder) so that, for example, a quantity of fluid extracted from the hollow organ and/or tissue may be measured and/or observed to, for example, determine a volume of fluid extracted from the hollow organ and/or tissue and/or whether or not blood clots are present in the fluid/material evacuated from the hollow organ and/or tissue, and, if so, a volume and/or size of the blood clots collected in the fluid collection device. This information may be used by a clinician to determine, for example, whether a hemorrhage has developed and/or is present, a severity of potential blood loss for the patient, and/or whether or not bleeding has slowed to a degree that enables safe extraction of the surgical drain from the hollow organ and/or tissue.

In step 1735, the surgical drain may be extracted from the hollow organ and/or tissue by, for example, pulling on a portion of the surgical drain positioned outside the hollow organ and/or tissue until the entire surgical drain is removed from the patient's body. Upon initiation extraction, the positioning mechanism may fold into a closed or partially folded configuration as shown in, for example, FIGS. 5F-5J and 6C and 6D and disclosed herein so that the exterior diameter of the surgical drain may be reduced, and the surgical drain may be atraumatically extracted from the patient's hollow organ and/or tissue and, in some cases, surrounding tissue and/or tissue proximate to the hollow organ and/or tissue (e.g., cervical canal, vaginal canal, esophagus, urethra, abdominal wall, muscle tissue, etc.).

Figure 18A:
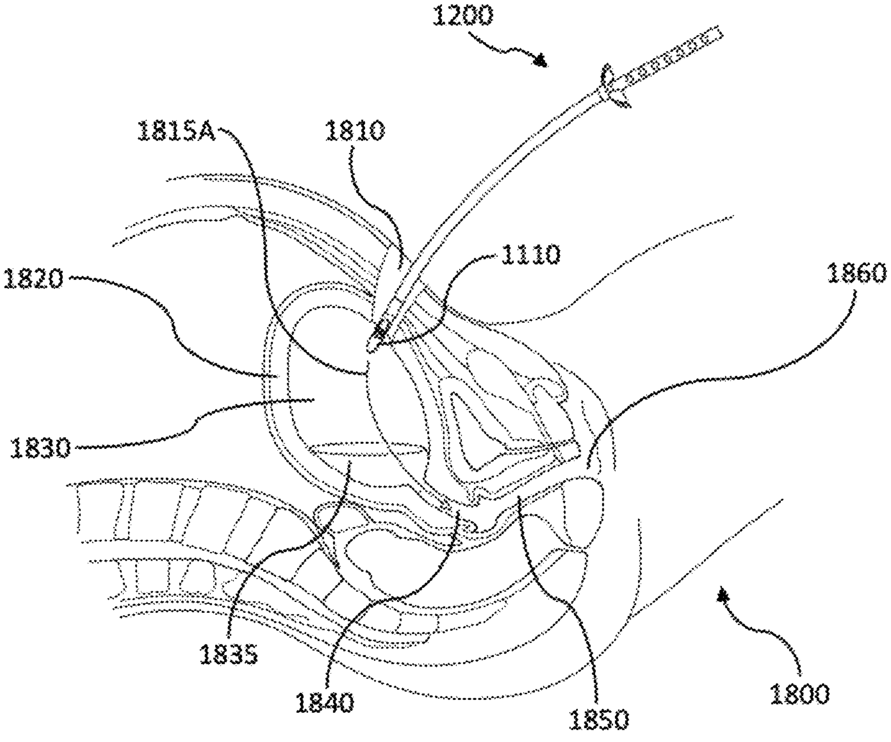
FIG. 18A is a schematic diagram of a mid-sagittal plane cross-section of an exemplary patient during a first stage of a surgical drain insertion process, wherein a tip and a portion of a tube of a surgical drain is inserted into a hysterotomy of the patient, in accordance with some embodiments of the present invention.

FIGS. 18A-18K are schematic diagrams of a process (e.g., process 1700) of using a surgical drain, like surgical drain 1200, within from a patient's 1800 hollow organ and/or tissue, in this instance, a uterus following surgical delivery of a fetus (i.e., via caesarean section) to drain the uterine cavity and apply suction tamponade to the uterus, thereby contracting the uterus and closing one or more open bleeding blood vessels that may be resultant from delivery of the fetus. The schematic diagrams of FIGS. 18A-18K are mid-sagittal plane cross-sections of patient 1800 that show the patient's uterus 1820, uterine cavity 1830, cervix, or cervical canal, 1840, vaginal canal 1850, and introitus, or vaginal opening, 1860. FIG. 18A provides an example of how step 1705 may be executed and shows an initial step of a surgical drain 1200 insertion/seating process that includes aligning tip 1110 and base 1120 with a hysterotomy 1810 within patient 1800 so that tip 1110 may be inserted into uterine cavity 1830 and fed caudally through uterine cavity 1830 along a first trajectory 1815A, which is represented by a curved, arrowed, line superimposed upon FIG. 18A. First trajectory 1815A directs tip 1110 and the remainder of surgical drain 1200 through hysterotomy 1810 and into uterine cavity 1830 toward cervical canal 1840. As is to be expected following childbirth, patient's uterus 1820 is in an enlarged state and cervix 1840 is non-dilated, or minimally dilated (e.g., 0.3-5 cm). In addition, fluids (e.g., blood) have collected in uterine cavity 1830 in a pool 1835 positioned at a lower (as oriented in FIG. 18A) portion of uterine cavity 1830. Pool 1835 may be positioned in a lower portion, or segment, of uterine cavity 1830 due to gravitational forces exerted thereon.

Figure 18B:
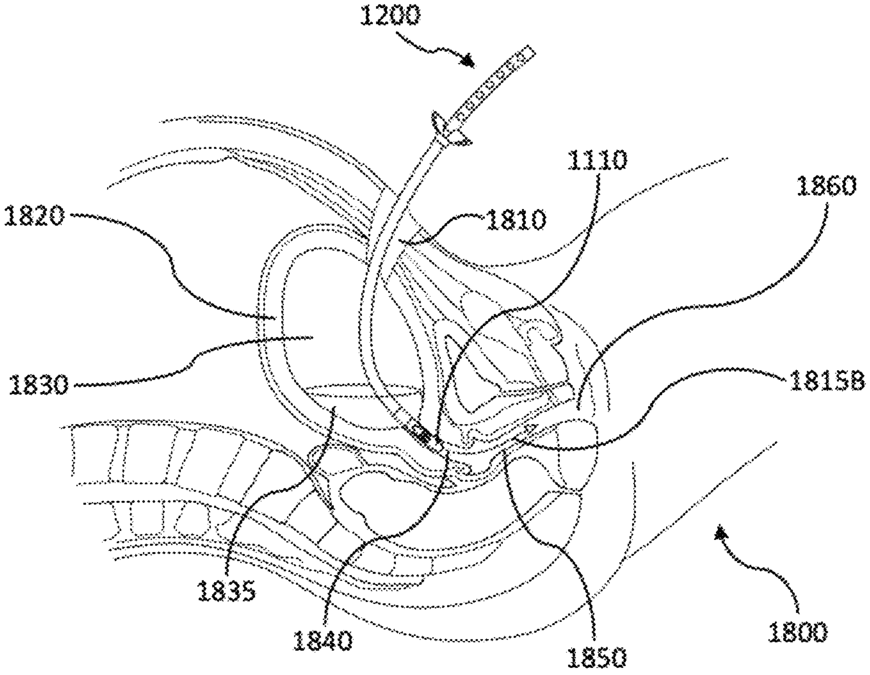
FIG. 18B is a schematic diagram of a mid-sagittal plane cross-section of the patient of FIG. 18A during a second stage of the surgical drain insertion process, wherein the tip of the surgical drain of FIG. 18A is inserted into the patient's internal cervical os and a portion of a tube of a surgical drain is positioned within a uterine cavity of the patient, in accordance with some embodiments of the present invention.
Figure 18C:
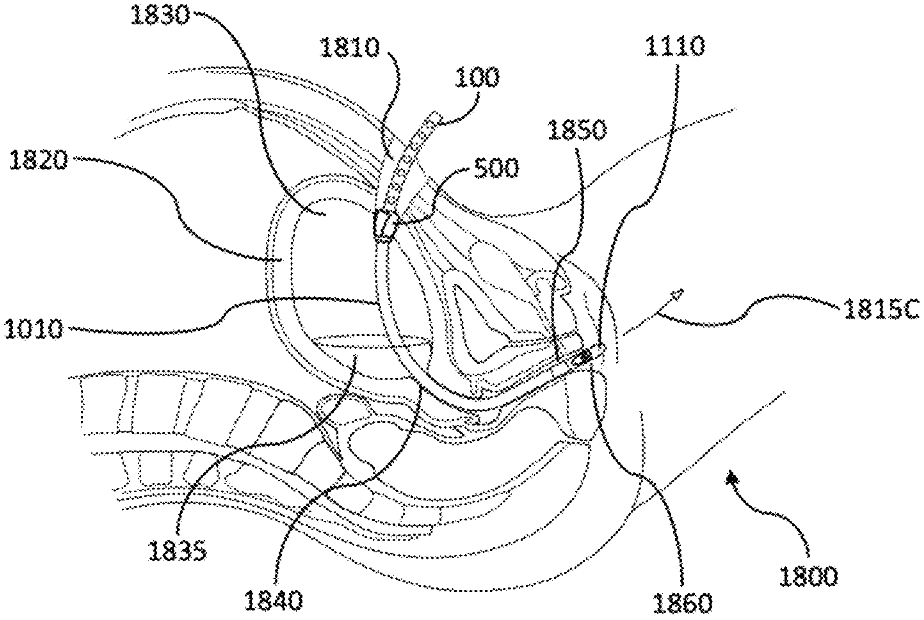
FIG. 18C is a schematic diagram of a mid-sagittal plane cross-section of the patient of FIG. 18A during a third stage of the surgical drain insertion process, wherein the tip of the surgical drain of FIG. 18A is positioned proximate to the patient's introitus, the tube is positioned within the patient's uterine cavity, a positioning mechanism of the surgical drain is folded as it passes through the hysterotomy, and a drainage component is partially resident within the hysterotomy, in accordance with some embodiments of the present invention.
Figure 18D:
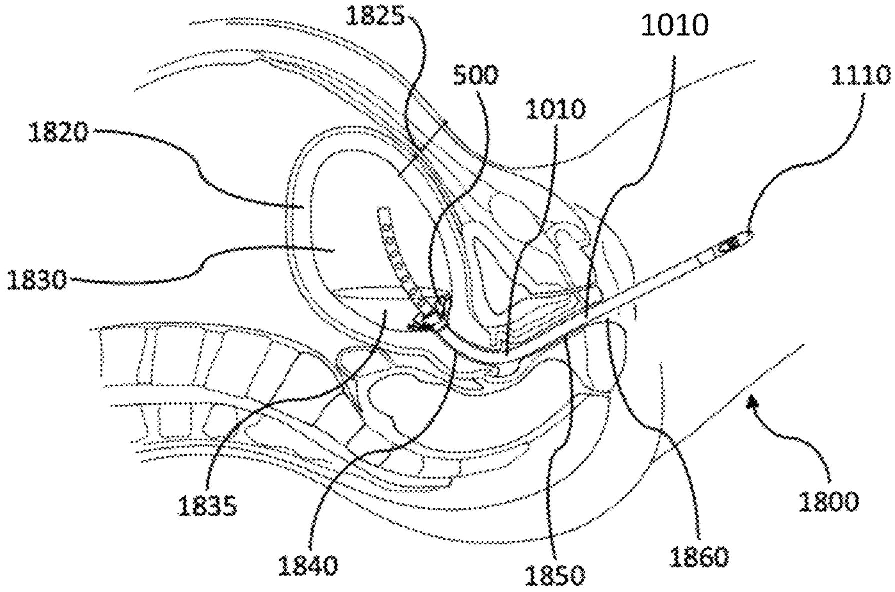
FIG. 18D is a schematic diagram of a mid-sagittal plane cross-section of the patient of FIG. 18A wherein the surgical drain of FIG. 18A is properly positioned within the patient's anatomy, wherein the tip has exited the patient's introitus, the tube is positioned within the patient's cervical canal and vaginal canal, the positioning mechanism is positioned proximate to the patient's internal cervical os while in an open, or unfolded, configuration, and the drainage extends into the patient's uterine cavity, in accordance with some embodiments of the present invention.
Figure 18E:
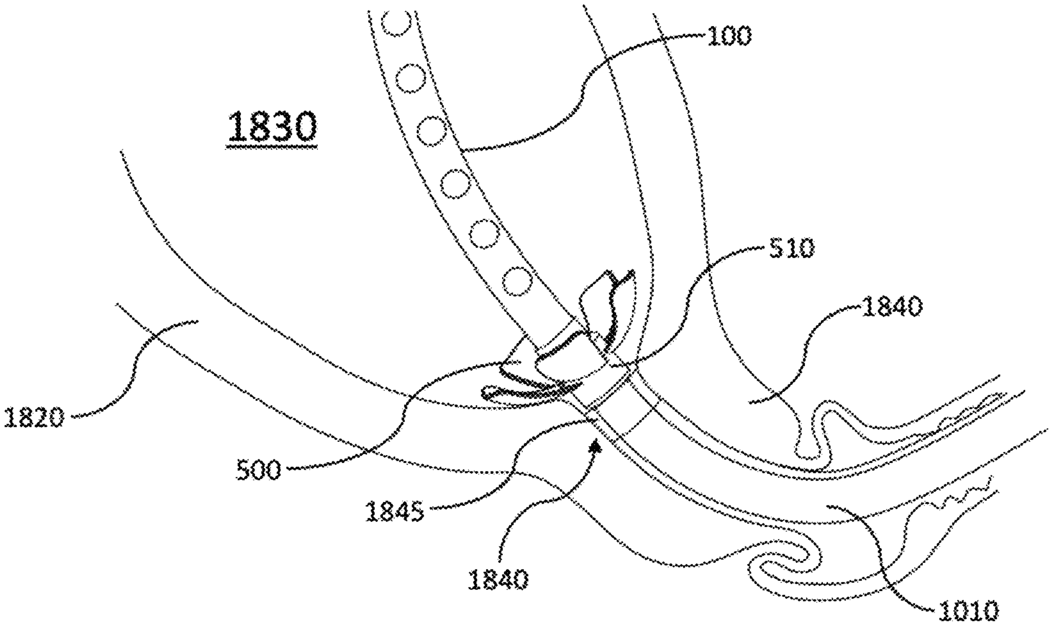
FIG. 18E is a schematic diagram of a close up view of a portion of schematic diagram of FIG. 18D, in accordance with some embodiments of the present invention.

FIGS. 18B-18E provide an example of how step 1710 of process 1700 may be executed. FIG. 18B depicts a second stage of the surgical drain insertion process/seating wherein tip 1110 travels through uterine cavity 1830, is inserted into an internal cervical os of the patient's cervical canal 1840 and has progressed through cervical canal 1840 to the external cervical os along first trajectory 1815A, wherein positioning mechanism 500 is still in an open state and is positioned outside patent's 1800 body. FIG. 18B also shows a second trajectory 1815B for surgical drain 1200 to travel through vaginal canal 1850 during a third stage of the surgical drain as shown in FIG. 18C. FIG. 18C depicts a third stage of the surgical drain insertion process, wherein tip 1110 is pushed through vaginal canal 1850 along second trajectory 1815B until tip 1110 begins to extend from introitus 1860 as shown. As tip 1110 travels toward introitus 1860, a portion tube 1010 proximate to positioning mechanism 500 is within uterine cavity 1830 and the extensions (extensions 520) of positioning mechanism 500 have transitioned to a closed state as they are pushed through hysterotomy 1810 as shown in FIG. 18C. FIG. 18C also shows a third trajectory 1815C that indicates a path for tip 1110 as it exits introitus 1860. Once through hysterotomy 1810 along third trajectory 1815C, positioning mechanism 500 may be fully seated and properly positioned within uterine cavity 1830 so that shaft 510 of positioning mechanism 500 is seated within an internal cervical os 1845 as shown in a close-up view of FIG. 18E and extensions 520 are arranged in an open state proximate to internal cervical os 1845. Extensions 520 positioned proximate to internal cervical os 1845 as shown may prevent further insertion of tube 1010 and/or drainage component 100 into the patient's anatomy and, as such, may provide feedback to a clinician inserting surgical drain 1200 into uterus 1820 that tube 1010 is fully inserted and drainage component 100 is properly positioned within uterine cavity 1830. When surgical drain 1200 if fully seated within patient 1800, tip 1110 and a portion of tube 1010 is positioned outside introitus 1860 between patient's 1800 legs as shown in FIG. 18D.

Figure 18F:
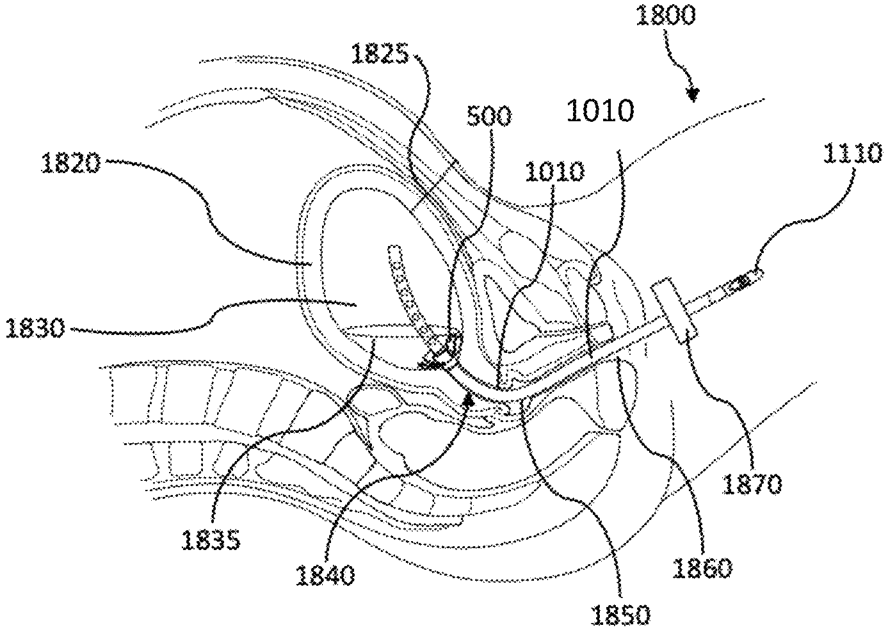
FIG. 18F is a schematic diagram of a mid-sagittal plane cross-section of the patient of FIG. 18A showing the surgical drain in position as shown in FIG. 18D with a portion of the tube taped to the patient's leg, in accordance with some embodiments of the present invention.

When surgical drain 1200 is properly seated within uterine cavity 1830, cervical canal 1840, and vaginal canal 1850, hysterotomy 1810 may be closed to form a closed hysterotomy 1825 as shown in, for example, FIG. 18D and described above with regard to step 1715, a portion of tube 1010 extending from introitus 1860 may be optionally secured to the patient's body as seen in, for example, FIG. 18F, wherein tube 1010 is secured to patient's 1800 leg via a piece of tape 1870 or other catheter/tube anchor such as a strap or housing. Surgical drain 1200 and/or drainage component 100 may be configured and/or positioned within uterine cavity 1830 so that it is out of the way when closing hysterotomy 1810 so that, for example, it is not accidentally engaged with and/or attached to one of the sutures or attachment mechanisms used to close hysterotomy 1810.

Alignment, insertion, and/or seating of surgical drain (and, in particular, shaft 510) into internal os 1845 of patient 1800 as shown in FIGS. 18A-18F may be facilitated by stylet 1101 and, in particular, first stiffening member 1140A, that may serve to provide sufficient stiffness to tube 1010 so that it may manipulated by a clinician and pushed through cervical and vaginal canals 1840 and 1850 without kinking, bunching, twisting, and/or bending as tip 1110 exits introitus 1860. Additionally, or alternatively, positioning mechanism 500 may assist a clinician with placement of tip 1110, tube 1010, and/or positioning mechanism 500 and may, for example, provide tactile feedback to a clinician when shaft 510 has entered internal os 1845 via, for example, providing pushback and/or requiring an increase in pressure to continue pushing surgical drain 1200 into patient's 1800 anatomy, which may act as an indication to the clinician to stop pushing surgical drain 1200 further into the patient.

Figure 18G:
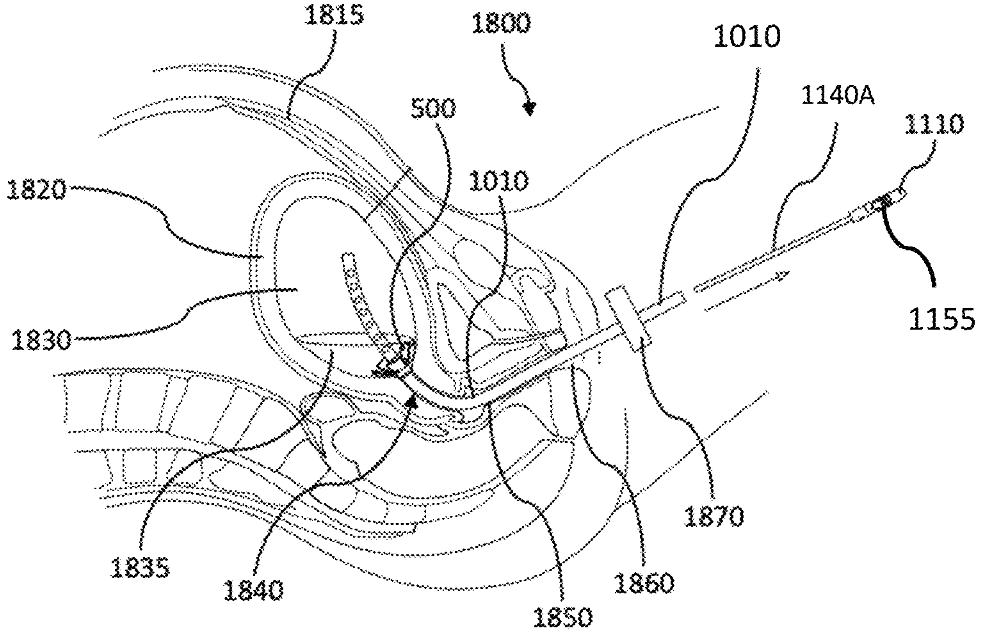
FIG. 18G is a schematic diagram of a mid-sagittal plane cross-section of the patient of FIG. 18A showing the surgical drain in position as shown in FIG. 18F and a stylet of the surgical drain being removed from the tube, in accordance with some embodiments of the present invention.

Once surgical drain 1200 is in position within uterine cavity 1830 as shown in, for example, FIG. 18F, the clinician (not shown) may grasp, hold, and pull grasping feature 1150 away from tube 1010 so stylet 1101 is removed from tube 1010 as shown in FIG. 18G and explained herein with regard to step 1720. Then, the open end of tube 1010 (i.e., the end from which stylet has been removed) may be coupled to a source of suction 1880 via a suction coupling 1885. Source of suction 1880 may be, for example, a vacuum pump or wall suction and suction coupling 1885 may be any device or combination of devices configured to couple to and form a seal (airtight or otherwise) with tube 1010. Alternatively, the open end of tube 1010 may be coupled to connector 1400 and reservoir device 1500 as shown in, for example, FIGS. 16A-16D.

Figure 18H:
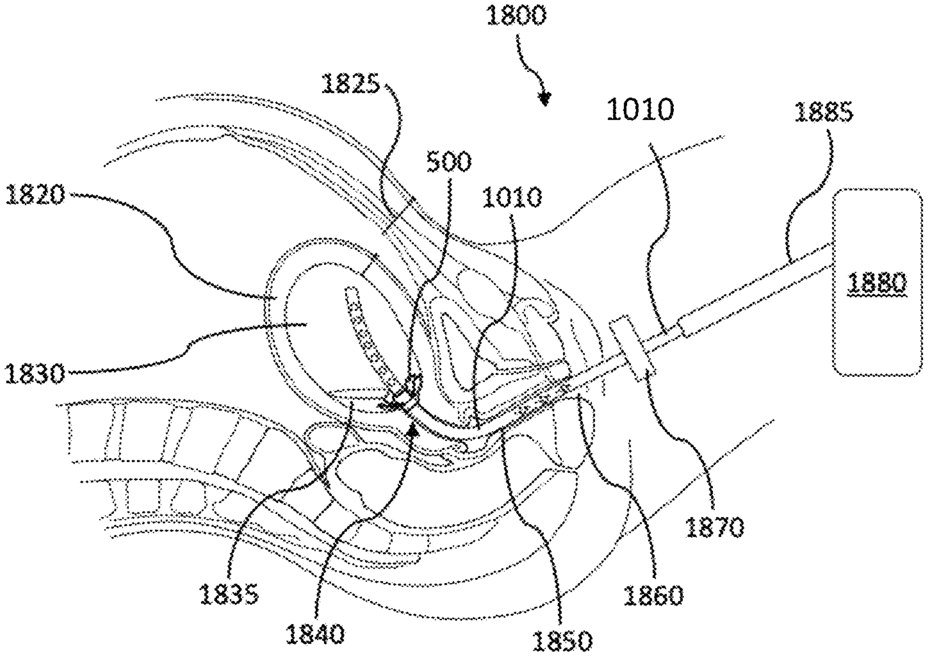
FIG. 18H is a schematic diagram of a mid-sagittal plane cross-section of the patient of FIG. 18A showing the surgical drain in position as shown in FIG. 18G with the stylet removed from the tube and the open end of the tube being attached to a source of suction, or negative pressure, in accordance with some embodiments of the present invention.
Figure 18I:
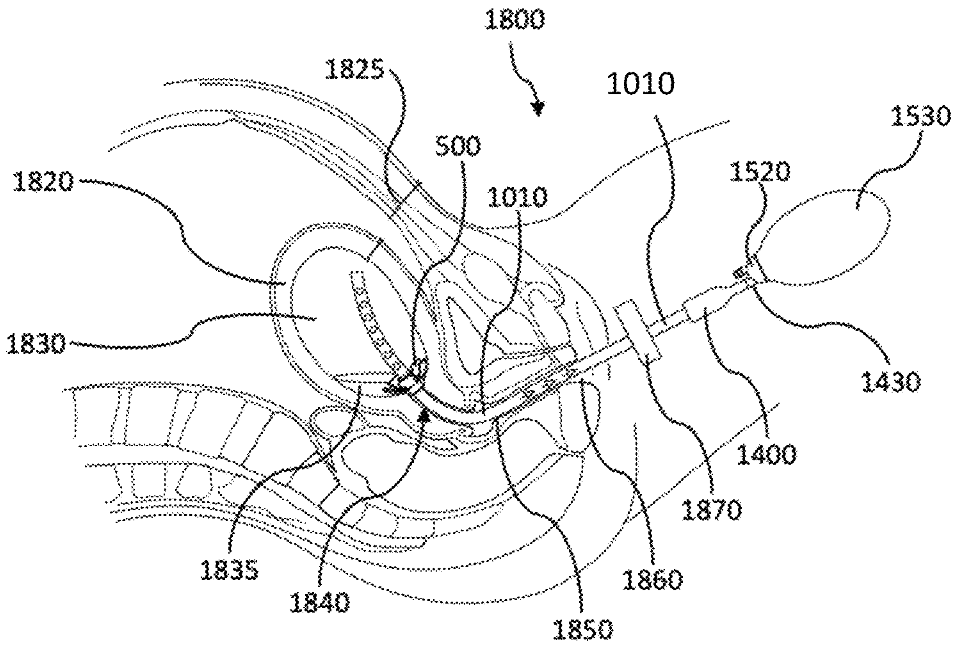
FIG. 18I is a schematic diagram of a mid-sagittal plane cross-section of the patient of FIG. 18A showing the surgical drain in position as shown in FIG. 18G with the stylet removed from the tube and the open end of the tube being attached to the suction reservoir device of FIG. 15, in accordance with some embodiments of the present invention.

When the open end of tube 1010 is coupled to suction source 1880 or reservoir device 1500 (via, e.g., execution of step 1730), suction may be applied to tube 1010, which may be communicated to drainage component 100 to pull gas and liquid into one or more drainage holes of drainage component 100 so that it may be evacuated from uterine cavity 1830, which may act to reduce a volume fluid/blood of pool 1835 as shown in FIGS. 18H and 18I. In some embodiments, a volume of fluid extracted from uterine cavity 1830 may be measured to, for example, determine how much blood patient 1800 has lost and/or whether patient needs further intervention to, for example, reduce bleeding and/or replace lost blood. Additionally, or alternatively, suction applied to tube 1010 that is communicated to drainage component 100 may act to contract uterus 1820 via a suction uterine tamponade mechanism of action, thereby decreasing a volume of uterine cavity 1830 as shown in FIGS. 18J and 18K and closing open or bleeding blood vessels in the uterine wall contributing to the volume of blood present in pool 1835.

Figure 18J:
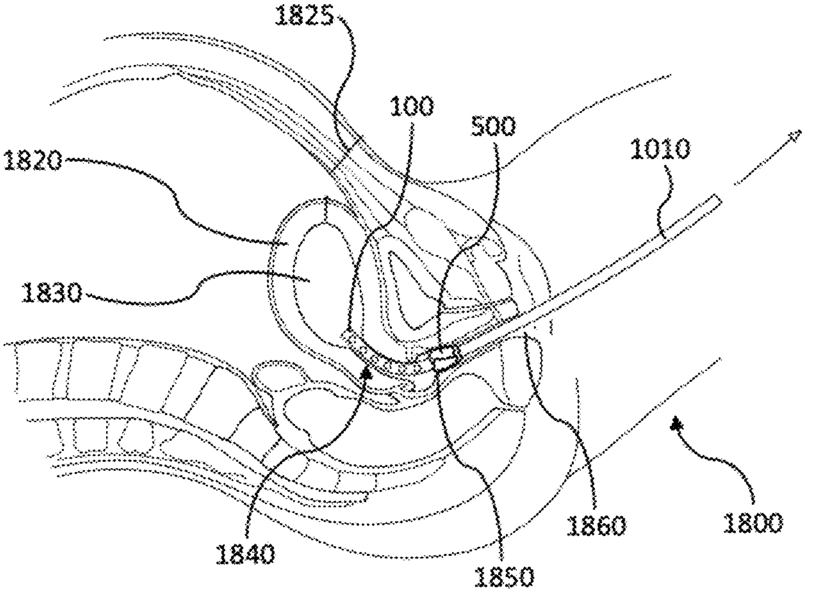
FIG. 18J is a schematic diagram of a mid-sagittal plane cross-section of the patient of FIG. 18A showing the surgical drain when partially removed from the patient's anatomy with the positioning mechanism of FIG. 5A in a folded configuration as it is drawn through the patient's cervix, in accordance with some embodiments of the present invention.
Figure 18K:
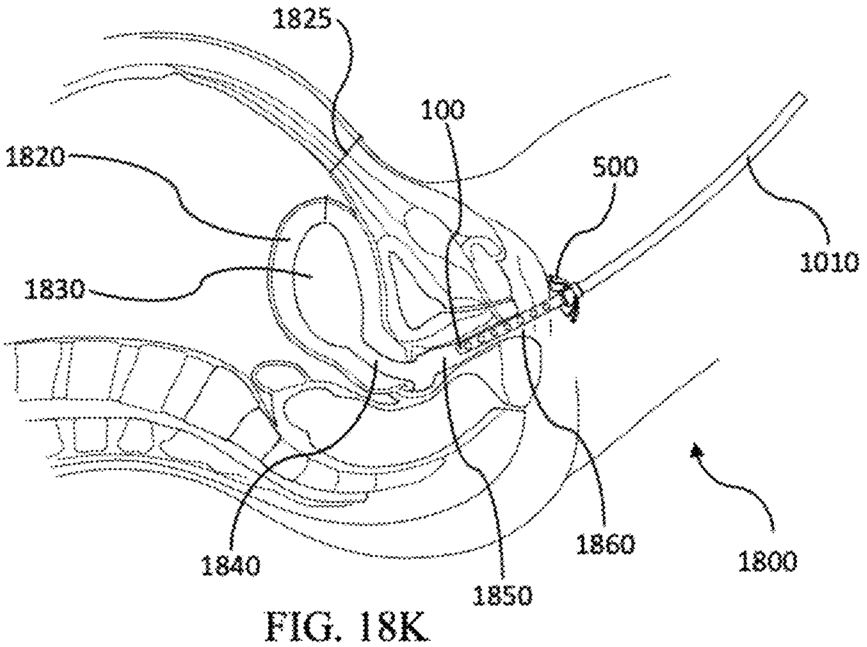
FIG. 18K is a schematic diagram of a mid-sagittal plane cross-section of the patient of FIG. 18A showing the surgical drain when the tube and positioning mechanism are fully removed from the patient's anatomy with the positioning mechanism of FIG. 5A in an unfolded configuration, in accordance with some embodiments of the present invention.

Once use of surgical drain 1200 is no longer necessary, as may be the case when no more, or a reduced amount, of blood and/or fluid is being drained from uterine cavity 1830, surgical drain 1200 may be extracted from patient 1800 (via, for example, execution of step 1735) by pulling on tube 1010 so that extensions 520 of positioning mechanism 500 fold into a folded configuration as shown in FIG. 18J to minimize its cross-sectional profile while being pulled through cervical canal 1840 and vaginal canal 1850 until surgical drain 1200 is fully extracted from patient 1800 as shown in FIG. 18K and drainage of uterine cavity 1830 concludes.

Figure 19:
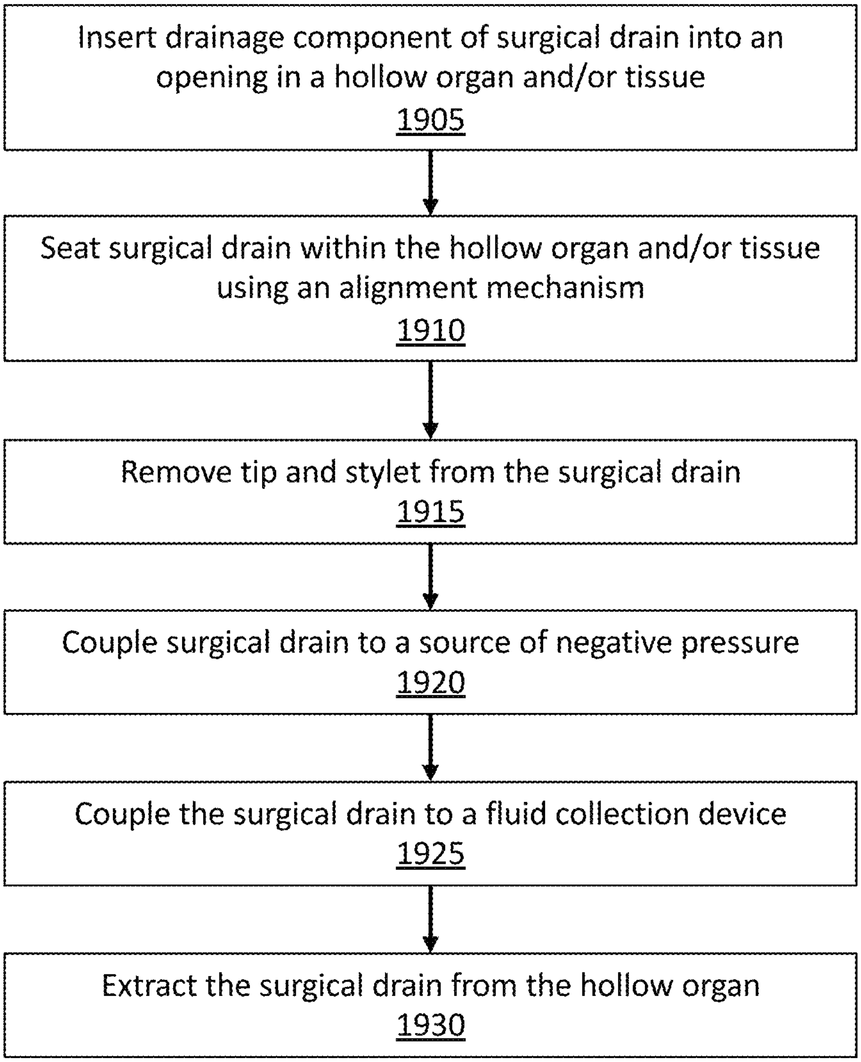
FIG. 19 provides a flowchart of a method for positioning a surgical drain within a hollow organ and/or tissue, using the surgical drain to drain and/or contract the hollow organ and/or tissue, and extract the surgical drain from the hollow organ and/or tissue that does not necessarily require insertion of the surgical drain via a surgical opening, in accordance with some embodiments of the present invention.

FIG. 19 provides a flowchart of a method for positioning a surgical drain (e.g., surgical drain 1201) or an assembly including a surgical drain (e.g., assembly 1600) within a hollow organ, such as a uterus, stomach, or bladder, and/or tissue such as lung or abdominal tissue (e.g., small intestine, large intestine, abdominal cavity, etc.), using the surgical drain to, for example, drain fluid (e.g., blood, urine, etc.) and/or blood clots from the hollow organ and/or tissue and/or contract a size, or volume, of the hollow organ and/or tissue and apply suction tamponade thereto. Initially, a drainage component (e.g., drainage component 100) or a drainage end of a surgical drain (e.g., surgical drain 1000 or 1200) may be inserted into an opening (e.g., a naturally occurring orifice or surgical opening) within the hollow organ and/or tissue of a patient (step 1905). In some instances, extensions of a positioning mechanism of the surgical drain (e.g., positioning mechanism 500, 600, 700, 800, and/or 900) may fold (e.g., backwards) or invert to, for example, reduce an overall circumference and/or profile of the positioning mechanism as the surgical drain is pushed through the patient's tissue.

Next, the surgical drain may be seated within the hollow organ and/or tissue by, for example, feeding or advancing the drainage component through tissue and/or an opening in tissue (e.g., vagina, cervical canal, etc.) until it is positioned within a cavity of the hollow organ and/or tissue and a tube (e.g., tube 1010) is positioned outside the patient's body. The surgical drain may be aligned, seated, and/or arranged within the hollow organ and/or tissue using a stylet (e.g., stylet 1102) and/or a stiffening member (e.g., second stiffening member 1140B) thereof, which may be configured to add sufficient stiffness to the surgical drain and/or a component thereof (e.g., drainage component 100 and/or tube 1010) to enable controlled insertion of the surgical drain into the hollow organ and/or tissue as it may be pushed through the hollow organ and/or tissue opening, additional tissue (e.g., cervix, endocervical canal, esophagus, urethra, etc.), hollow organ cavity, and/or surgical opening to be properly seated within the hollow organ and/or tissue without kinking or deforming the surgical drain or a component thereof. Additionally, or alternatively, the surgical drain may be aligned, seated, and/or arranged within the hollow organ and/or tissue using an positioning mechanism such as positioning mechanism 500, which may be configured to provide tactile feedback to a clinician who is placing the surgical drain within the hollow organ and/or tissue so that, for example, the clinician can feel when the drain is in a desired position and/or may prevent the surgical drain from being pushed too far into the patient's anatomy. In some embodiments, when, for example, the drainage component of the surgical drain is inserted into a uterus, the cervix may be dilated (e.g., 1-10 cm) to accommodate passage of the drainage component and/or positioning mechanism therethrough.

In step 1915, a tip (e.g., tip 1010) and optional second stylet 1102 may be removed from a lumen (e.g., lumen 1020) of the surgical drain thereby opening the lumen of the surgical drain. Then, an end of the surgical drain exposed by removal of the tip may be coupled to a source of negative pressure such as a vacuum pump and/or suction reservoir device (e.g., suction reservoir device 1500) so that negative pressure may be applied to the surgical drain, which communicates the negative pressure to the hollow organ and/or tissue via, for example, one or more drainage holes (e.g., holes 120) that may serve to apply the negative pressure to a cavity of the hollow organ and/or tissue to, for example, evacuate fluids from the hollow organ and/or tissue and/or contract a size and/or volume of the hollow organ and/or tissue, which may limit blood flowing from vessels within the hollow organ and/or tissue.

Optionally, in step 1920, an end the surgical drain not positioned within the hollow organ and/or tissue (e.g., an end of tube not proximate to the drainage component) may be coupled to, for example, a source of suction, such as a vacuum pump and/or a suction reservoir device such as suction reservoir device 1500. In some embodiments, step 1920 may be executed in a manner similar to execution of step 1725.

Additionally, or alternatively, in step 1925, the end of the surgical drain exposed by removal of the tip may be coupled to a collection device (e.g., gauze, absorbent pad, bag, and/or graduated cylinder) so that, for example, a quantity of fluid extracted from the hollow organ and/or tissue may be measured and/or observed to, for example, determine a volume of fluid extracted from the hollow organ and/or tissue and/or whether or not blood clots are present in the fluid/material evacuated from the hollow organ and/or tissue, and, if so, a volume and/or size of the blood clots collected in the fluid collection device. This information may be used by a clinician to determine, for example, whether a hemorrhage has developed and/or is present, a severity of potential blood loss for the patient, and/or whether or not bleeding has slowed to a degree that enables safe extraction of the surgical drain from the hollow organ and/or tissue.

In step 1930, the surgical drain may be extracted from the hollow organ and/or tissue by, for example, pulling on a portion of the surgical drain positioned outside the hollow organ and/or tissue until the entire surgical drain is removed from the patient's body. Upon initiation extraction, the positioning mechanism may fold into a closed or partially folded configuration as shown in, for example, FIGS. 5F-5J and 6C and 6D and disclosed herein so that the exterior diameter of the surgical drain may be reduced, and the surgical drain may be atraumatically extracted from the patient's hollow organ and/or tissue and, in some cases, surrounding tissue and/or tissue proximate to the hollow organ and/or tissue (e.g., cervical canal, vaginal canal, esophagus, urethra, abdominal wall, muscle tissue, etc.).

Figure 20A:
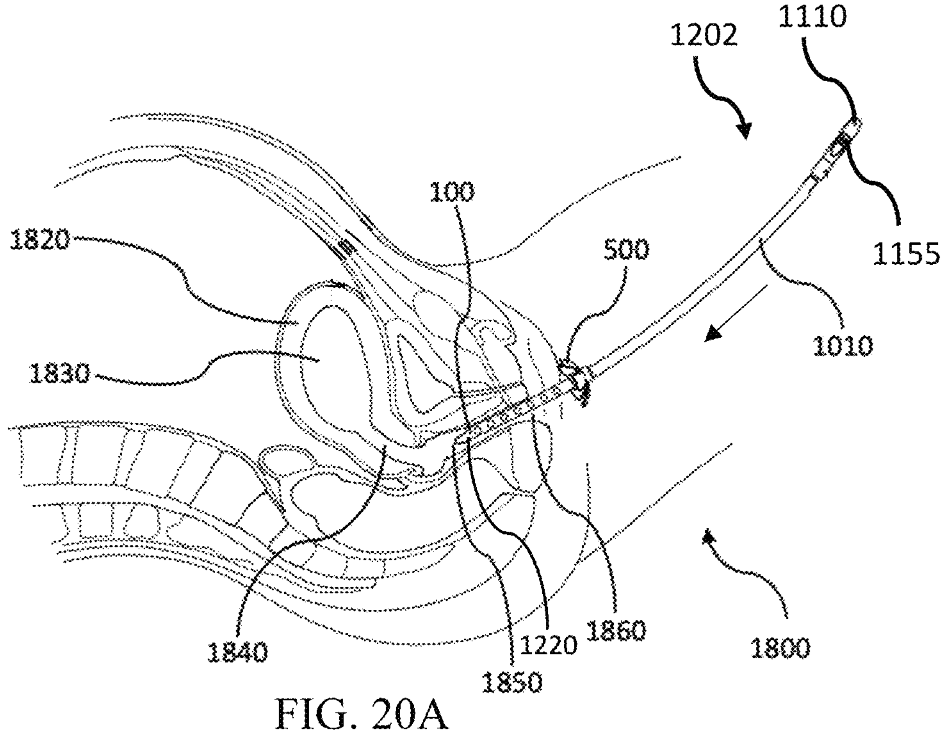
FIG. 20A is a schematic diagram of a mid-sagittal plane cross-section of an exemplary patient during a first stage of a surgical drain insertion process, wherein a drainage component of the surgical drain is inserted into the introitus and pushed into the vaginal canal and the alignment mechanism of FIG. 5A is positioned outside the patient's anatomy and is in an unfolded configuration, in accordance with some embodiments of the present invention.
Figure 20B:
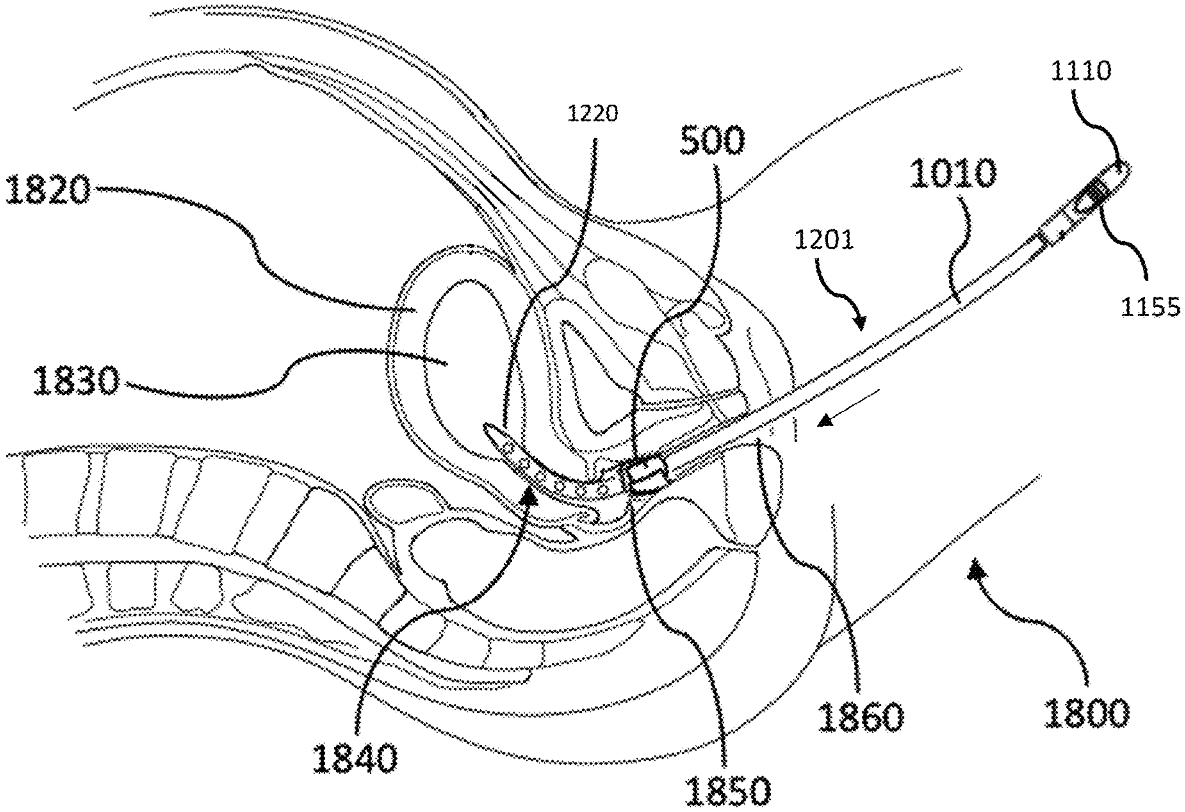
FIG. 20B is a schematic diagram of a mid-sagittal plane cross-section of the patient of FIG. 20A during a second stage of the surgical drain insertion process, wherein a drainage component of the surgical drain has traveled through the patient's cervical opening and the alignment mechanism is in a folded configuration, in accordance with some embodiments of the present invention.
Figure 20C:
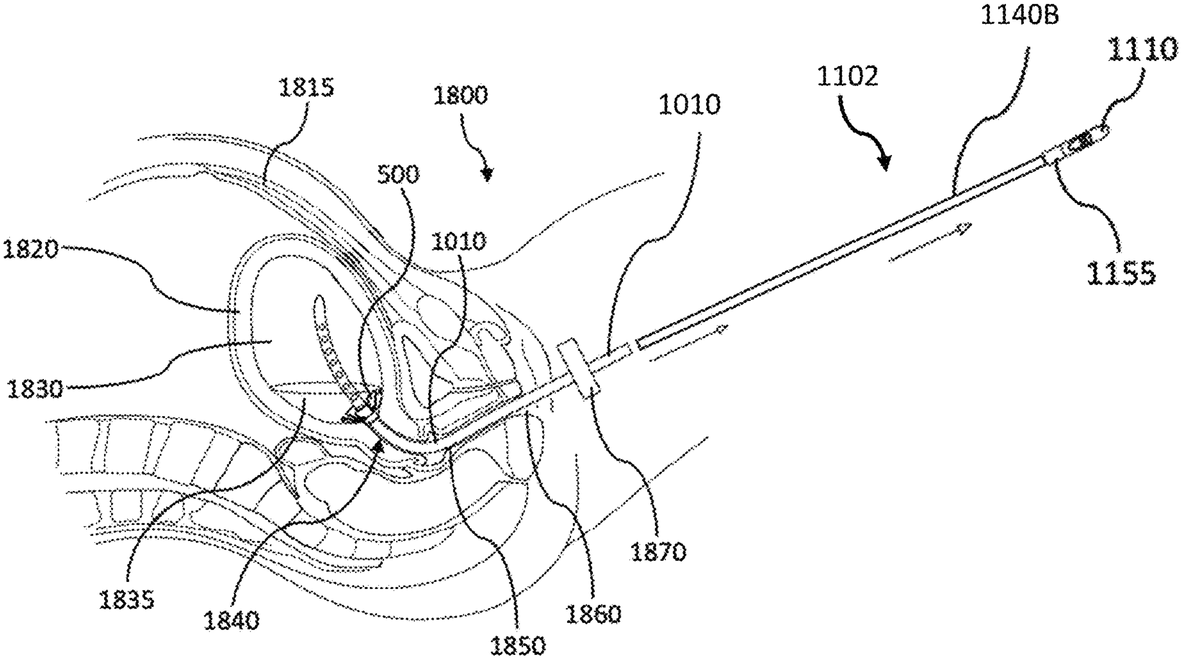
FIG. 20C is a schematic diagram of a mid-sagittal plane cross-section of the patient of FIG. 20A when the surgical drain is seated within the patient's uterine cavity and a stylet of the surgical drain is extracted from a tube of the surgical drain, in accordance with some embodiments of the present invention.

FIGS. 20A-20C are schematic diagrams of a process (e.g., process 1900) of using a surgical drain, like surgical drain 1201, within a patient's 1800 hollow organ and/or tissue, in this instance, a uterus to drain the uterine cavity and apply suction tamponade to the uterus, thereby contracting the uterus and closing one or more open bleeding blood vessels that may be resultant from delivery of the fetus. Once in position, surgical drain 1201 may be used and/or extracted in a manner similar to that shown in FIGS. 18H, 18I, 18J, and/or 18K and as discussed herein. Surgical drain 1201 is placed within the patient's uterus via the vaginal route and a surgical opening is not required. The schematic diagrams of FIGS. 20A-20C are mid-sagittal plane cross-sections of patient 1800 that show the patient's uterus 1820, uterine cavity 1830, cervix, or cervical canal, 1840, vaginal canal 1850, and introitus, or vaginal opening, 1860.

FIG. 20A provides an example of how step 1905 may be executed and shows an initial step of a surgical drain 1201 insertion/seating process that includes aligning drainage component 100 with vaginal opening 1860 so that it may be inserted into, and pushed through, vaginal canal 1850 (see FIG. 20A), the patient's external cervical os and cervical canal 1840 (see FIG. 20B) until drainage component 100 is fully pushed through cervical canal and positioning mechanism 500 is positioned at the base of uterus 1820 proximate to cervical canal 1840 as shown in FIG. 20C. Often times, cervix 1840 may be dilated (e.g., 1-10 cm or 2 cm) prior to insertion and passage of the drainage component 100 and/or positioning mechanism 500 therethrough.

Alignment, insertion, and/or seating of surgical drain 1201 (and, in particular, shaft 510) into internal os 1845 of patient 1800 as shown in FIGS. 20A-20C may be facilitated by stylet 1102 and, in particular, second stiffening member 1140B, that may serve to provide sufficient stiffness to drainage component 100 and tube 1010 so that it may manipulated by a clinician and pushed through cervical and vaginal canals 1840 and 1850 without kinking, bunching, twisting, and/or bending. Additionally, or alternatively, positioning mechanism 500 may assist a clinician with placement of surgical drain 1201 by, for example, providing tactile feedback to a clinician when shaft 510 has entered internal os 1845 via, for example, providing pushback and/or requiring an increase in pressure to continue pushing surgical drain 1201 into patient's 1800 anatomy, which may act as an indication to the clinician to stop pushing surgical drain 1201 further into the patient.

When surgical drain 1201 is properly seated within uterine cavity 1830, cervical canal 1840, and vaginal canal 1850 as shown in FIG. 20C, a portion of tube 1010 extending from introitus 1860 may be optionally secured to the patient's body as via, for example, a piece of tape 1870 affixed to the patient's leg or other catheter/tube anchor such as a strap or housing.

Once surgical drain 1201 is in position within uterine cavity 1830 as shown in, for example, FIG. 20C, the clinician (not shown) may grasp, hold, and pull grasping feature 1150 away from tube 1010 so stylet 1102 is removed from tube 1010 as shown in FIG. 20C and explained herein with regard to step 1915. Then, the open end of tube 1010 (i.e., the end from which stylet has been removed) may be coupled to a source of suction such as source of suction 1880 via a suction coupling such as suction coupling 1885 in a manner similar to that shown in FIG. 18H and/or 18I and discussed herein with regard to step 1920. Additionally, or alternatively, open end of tube 1010 may be coupled to a reservoir device like reservoir device 1500 and/or an absorbent material (e.g., gauze pad) via, for example, execution of step 1925.

When the open end of tube 1010 is coupled to suction source 1880 or reservoir device 1500 (via, e.g., execution of step 1920), suction may be applied to tube 1010, which may be communicated to drainage component 100 to pull gas and liquid into one or more drainage holes of drainage component 100 so that it may be evacuated from uterine cavity 1830, which may act to reduce a volume fluid/blood of pool 1835. In some embodiments, a volume of fluid extracted from uterine cavity 1830 may be measured to, for example, determine how much blood patient 1800 has lost and/or whether patient needs further intervention to, for example, reduce bleeding and/or replace lost blood. Additionally, or alternatively, suction applied to tube 1010 that is communicated to drainage component 100 may act to contract uterus 1820 via a suction uterine tamponade mechanism of action, thereby decreasing a volume of uterine cavity 1830 as shown in FIGS. 18J and 18K and closing open or bleeding blood vessels in the uterine wall contributing to the volume of blood present in pool 1835.

Once use of surgical drain 1201 is no longer necessary, as may be the case when no more, or a reduced amount, of blood and/or fluid is being drained from uterine cavity 1830, surgical drain 1201 may be extracted from patient 1800 (via, for example, execution of step 1930) by pulling on tube 1010 so that extensions 520 of positioning mechanism 500 fold into a folded configuration as shown in FIG. 18J to minimize its cross-sectional profile while being pulled through cervical canal 1840 and vaginal canal 1850 until surgical drain 1201 is fully extracted from patient 1800 as shown in FIG. 18K and drainage of uterine cavity 1830 concludes.

Although FIGS. 18A-18K and 20A-20C show use of a surgical drain with positioning mechanism 500, this need not always be the case and the surgical drains disclosed herein may be used with any of the positioning mechanisms disclosed herein. For example, surgical drain 1200 and/or 1201 may include positioning mechanism 600, 700, 800, and/or 900 instead of, or in addition to, positioning mechanism 500 when, for example, processes 1700 and/or 1900 and/or the processes of FIGS. 18A-18K and 20A-20C are executed.

The invention claimed is:

1. A method for evacuating fluid from a uterus of a patient following pelvic surgery, the method comprising:

placing a surgical drain with a positioning mechanism in the patient's body so that a drainage component of the surgical drain extends into a uterine cavity of the patient, the positioning mechanism sits in the uterine cavity, and a portion of a tube of the surgical drain extends through a cervical canal and a vaginal canal of the patient, wherein the drainage component includes a drain lumen in communication with a tube lumen of the tube, the drainage component includes at least one opening configured to allow fluid to enter the drainage lumen to be evacuated from the uterus via the tube lumen, and the positioning mechanism includes a plurality of extensions, each extension separately, and approximately orthogonally, extending from a shaft that encircles a portion of an exterior surface of the tube, wherein each extension is not joined to an adjacent extension of the plurality, does not touch an adjacent extension of the plurality when the positioning mechanism is in an open configuration, and is configured to move independently of an adjacent extension of the plurality, and wherein one or more extensions of the plurality of extensions have a curved shape along their width with a concave curvature configured to correspond to a diameter of the tube so that the one or more extensions may fold closely to the tube when in a folded configuration.

2. The method of claim 1, wherein a portion of the tube extends through an introitus of the patient, the method further comprising:

extracting the drainage component from the uterine cavity by pulling on the portion of the tube extends through the introitus of the patient, wherein the plurality of extensions are configured to fold when pulled through the cervix as the drainage component is removed from the uterine cavity.

3. The method of claim 1, wherein the surgical drain includes a stylet configured to add stiffness to the surgical drain as it is placed in the uterine cavity, the method further comprising:

removing the stylet from the surgical drain thereby opening an end of the tube extending through an introitus of the patient; and coupling the end of the tube to a source of suction.

4. The method of claim 1, wherein the positioning mechanism sits proximate to an internal cervical os of the patient.

5. A method for applying suction tamponade to a uterus of a patient following pelvic surgery, the method comprising:

placing a surgical drain with a positioning mechanism in the patient's body so that a drainage component of the surgical drain extends into a uterine cavity of the patient, the positioning mechanism sits in the uterine cavity, and a portion of a tube of the surgical drain extends through a cervical canal and a vaginal canal of the patient, wherein the drainage component includes a drain lumen in communication with a tube lumen of the tube, the drainage component includes at least one opening configured to allow fluid to enter the drainage lumen to be evacuated from the uterus via the tube lumen, and the positioning mechanism includes a plurality of extensions, wherein each extension separately and approximately orthogonally extends from a shaft that encircles a portion of an exterior surface of the tube, does not touch an adjacent extension of the plurality when the positioning mechanism is in an open configuration, and is configured to move independently of an adjacent extension of the plurality, and wherein one or more extensions of the plurality of extensions have a curved shape along their width with a concave curvature configured to correspond to a diameter of the tube so that the one or more extensions may fold closely to the tube when in a folded configuration;

coupling the first end of the tube to a source of suction; and applying an amount of negative pressure to the tube using the source of suction, the amount of negative pressure being sufficient to contract the patient's uterus, wherein the negative pressure is communicated to the uterine cavity via the tube lumen, drain lumen, and the at least one opening.

6. The method of claim 5, wherein a portion of the tube extends through an introitus of the patient, the method further comprising:

extracting the drainage component from the uterine cavity by pulling on the portion of the tube that extends through the introitus of the patient, wherein the plurality of extensions are configured to fold when pulled through the cervix as the drainage component is removed from the uterine cavity.

7. The method of claim 5, wherein the surgical drain includes a stylet configured to add stiffness to the surgical drain as it is placed in the uterine cavity, the method further comprising:

removing the stylet from the surgical drain thereby opening an end of the tube extending through an introitus of the patient; and coupling the end of the tube to a source of suction.

8. The method of claim 5, wherein the positioning mechanism sits proximate to an internal cervical os of the patient.

* * * * *